(12) United States Patent
Aquila et al.

(10) Patent No.: US 8,461,170 B2
(45) Date of Patent: Jun. 11, 2013

(54) CHEMICAL COMPOUNDS

(75) Inventors: Brian Aquila, Waltham, MA (US);
Victor Kamhi, Waltham, MA (US); Bo Peng, Waltham, MA (US); Timothy Pontz, Waltham, MA (US); Jamal Carlos Saeh, Waltham, MA (US); Kumar Thakur, Waltham, MA (US); Bin Yang, Waltham, MA (US)

(73) Assignee: Astrazeneca AB, Sodertalje (SE)

( * ) Notice: Subject to any disclaimer, the term of this patent is extended or adjusted under 35 U.S.C. 154(b) by 31 days.

(21) Appl. No.: 13/196,189

(22) Filed: Aug. 2, 2011

(65) Prior Publication Data
US 2012/0028924 A1    Feb. 2, 2012

Related U.S. Application Data

(60) Provisional application No. 61/369,917, filed on Aug. 2, 2010, provisional application No. 61/372,055, filed on Aug. 9, 2010, provisional application No. 61/390,944, filed on Oct. 7, 2010.

(51) Int. Cl.
*A01N 43/54*     (2006.01)
*A61K 31/505*    (2006.01)

(52) U.S. Cl.
USPC ............ 514/275; 544/330; 544/333; 544/334

(58) Field of Classification Search
USPC ............................ 514/275; 544/330, 333, 334
See application file for complete search history.

(56) References Cited

U.S. PATENT DOCUMENTS
2008/0300242 A1   12/2008   Kuntz et al.

FOREIGN PATENT DOCUMENTS
| WO | 2007/149427 A2 | 12/2007 |
| WO | WO 2007/149427 | * 12/2007 |
| WO | 2009/024824 A1 | 2/2009 |
| WO | 2010/049731 A1 | 5/2010 |

OTHER PUBLICATIONS

Alam et al. 'Synthesis and SAR of Aminopyrimidines as Novel c-Jun N-terminal Kinase (JNK) Inhibitors' Bioorganic & Medicinal Chemistry Letters (2007); vol. 17; pp. 3463-3467; XP022097804.
Emmitte et al. 'Discovery and Optimization of Imidazo[1,2-a]pyridine Inhibitors of Insulin-like Growth Factor-1 Receptor (IGF-1R)'Bioorganic & Medicinal Chemistry Letters (2009); vol. 19; pp. 1004-1008; XP025893617.
Galkin et al. 'Identification of NVP-TAE684, A Potent, Selective, and Efficacious Inhibitor of NPM-ALK' Proceedings of the National Academy of Sciences of the United States of America (2007); vol. 104; No. 1; pp. 270-275; XP002661293.
Huang et al. 'Synthesis and Biological Study of 2-amino-4-aryl-5-chloropyrimidine Analogues as Inhibitors of VEGFR-2 and Cyclin Dependent Kinase 1 (CDK1)' Bioorganic & Medicinal Chemistry Letters (2007); vol. 17; pp. 2179-2183; XP022009228.
International Search Report for PCT/GB2011/051465, mailed Feb. 23, 2012.
Luth 'Syntheses of 4-(indole-3-yl)quinazolines—A New Class of Epidermal Growth Factor Receptor Tyrosine Kinase Inhibitors' European Journal of Medicinal Chemistry (2008); vol. 43; pp. 1478-1488; XP022795993.
Written Opinion for PCT/GB2011/051465, mailed Feb. 23, 2012.

* cited by examiner

*Primary Examiner* — Yong Chu
*Assistant Examiner* — Valerie Rodriguez-Garcia
(74) *Attorney, Agent, or Firm* — Astrazeneca AB

(57) ABSTRACT

The present invention relates to compounds of Formula (I) and/or Formula (Ia):

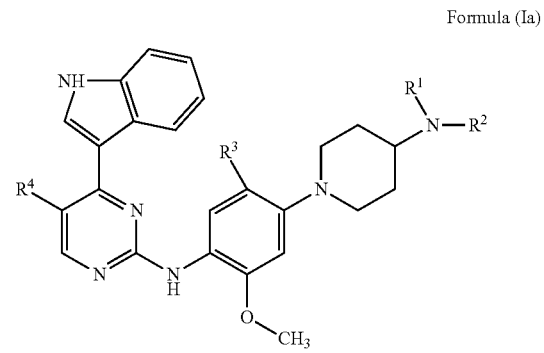

Formula (Ia)

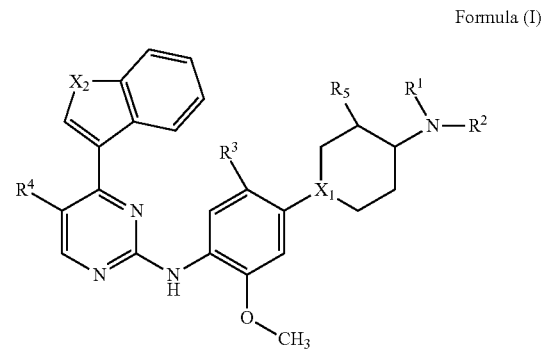

Formula (I)

and to their salts, pharmaceutical compositions, methods of use, and methods for their preparation. These compounds inhibit ALK kinase activity, and thus may be used for the treatment of cancer.

2 Claims, No Drawings

CHEMICAL COMPOUNDS

RELATED APPLICATIONS

This application claims priority to U.S. provisional patent application Ser. No. 61/369,917, filed Aug. 2, 2010; to U.S. provisional patent application Ser. No. 61/372,055, filed Aug. 9, 2010; and to U.S. provisional patent application Ser. No. 61/390,944, filed Oct. 7, 2010, the entire disclosure of each of which is incorporated herein by reference.

FIELD OF THE INVENTION

The present invention relates to novel compounds, and to their pharmaceutical compositions. In addition, the present invention relates to therapeutic methods for the treatment and prevention of cancers and to the use of these compounds in the manufacture of medicaments for the treatment and prevention of cancer.

BACKGROUND OF THE INVENTION

Anaplastic lymphoma kinase (ALK) is a 200 kd receptor tyrosine kinase encoded by the ALK gene on chromosome 2p23. ALK belongs to the insulin receptor superfamily. Normal expression of ALK is tightly controlled and limited to the testis, ganglion cells of the intestine and neural tissues. The function is not well understood as ALK null mice exhibit a normal phenotype, however recent data suggests that ALK is involved in neuronal cell differentiation and regeneration, synapse formation and muscle cell migration.

ALK was first identified in a chromosomal translocation associated with some anaplastic large cell lymphomas (ALCL). Approximately 50-60% of cases are associated with the t(2;2)(p23;q35) chromosomal translocation which generates a hybrid gene consisting of the intracellular domain of the ALK tyrosine kinase receptor juxtaposed with nucleophosmin (NPM), a nucleolar protein involved in shuttling ribonucleoproteins. The resulting fusion protein, NPM-ALK has constitutive kinase activity and transforms a variety of immortalized cell lines in vitro and supports tumor formation in vivo by controlling key cellular processes such as cell cycle progression, survival, cell migration and cell shaping (Chiarle et al., Nature Reviews Cancer, 8:11-23, 2008). Similarly, expression of NPM-ALK driven by a CD4 promoter in transgenic mice resulted in the development of aggressive lymphoma of multiple origins. Several signaling pathways have been implicated in the pathogenesis of NPM-ALK positive ALCLs. NPM-ALK has been shown to activate several members of the signal transducer and activator of transcription (STAT) family, including STAT3 and STAT5 as well as phospholipase C-γ and the PI3-kinase/AKT pathway. Other ALK fusions partners have been reported in ALCL in addition to CD30-negative diffuse large cell lymphoma, albeit with lower frequency.

Translocations linking ALK to multiple fusion partners were subsequently identified in inflammatory myofibroblastic tumors, esophageal squamous cell carcinomas, neuroblastoma and, more recently, in non small cell lung cancer (NSCLC) (Soda et al, Nature 448:561-566, 2007). In NSCLC, a novel translocation was initially identified in which a small inversion within chromosome 2p results in formation of a fusion gene comprising portions of the echinoderm microtubule-associated protein-like 4 (EML4) and ALK genes. Expression of this fusion protein in mouse 3T3 fibroblasts results in generation of transformed foci in culture and tumors in mice. The frequency of the EML4-ALK fusion was first reported to be 6.7% in NSCLC in Japanese patients. The presence of EML4-ALK fusions has been confirmed in a number of subsequent studies and other fusion partners have also been reported or proposed in NSCLC (Rikova et al., Cell 131:1190-1203, 2007; Perner et al., Neoplasia 10:298-302, 2008). Most recently, EML4-ALK fusions have been reported in breast and colorectal patient tumor samples (Lin et al., Mol. Cancer Res. 7:1466-1476, 2009). Germline and somatic mutations have also been observed in neuroblastoma and gain/amplification of ALK has been associated with aggressive clinical phenotype and death (Janoueix-Lerosey et al. Nature 455:967-970, 2008, Mosse et al., Nature 455:930-935, 2008).

Selective ALK inhibitors have been shown to induce cell cycle arrest and apoptosis in vitro ALCL, NSCLC and neuroblastoma cell lines harboring ALK rearrangements, mutation or amplification in vitro and cause tumor growth inhibition or regression in ALK-positive tumor xenograft models (Christensen et al., Mol Cancer Ther. 6:3314-3322, 2007; McDermott et al., Cancer Res. 68:3389-3395, 2008; Koivunen et al., Clin Cancer Res. 14:4275-4283, 2008). Significant growth inhibition or cell death has also been observed in some cancer cell lines containing an EML4-ALK fusion following EML4 and ALK silencing by small interfering RNA (Lin et al., Mol. Cancer Res. 7:1466-1476, 2009). ALK inhibtiors therefore represent a potential treatment for patients whose tumors contain ALK abberations.

SUMMARY OF THE INVENTION

The present invention relates to compounds of Formula (I):

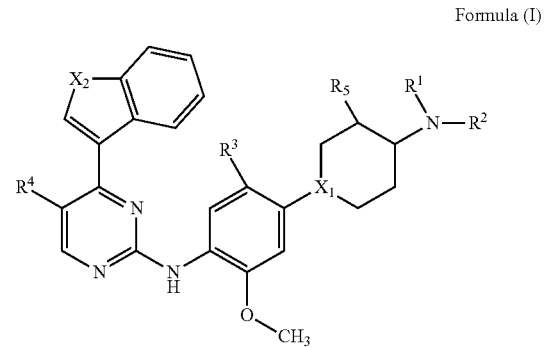

Formula (I)

and/or to pharmaceutically acceptable salts thereof.

Compounds of Formula (I) and/or Formula (Ia) possess beneficial efficacious, metabolic, pharmacokinetic, and/or pharmacodynamic properties. Compounds of Formula (I) and/or Formula (Ia) are useful for their ability to inhibit ALK kinase activity and are also useful in the treatment of diseases or medical conditions mediated alone or in part by the ALK tyrosine kinase. Compounds of Formula (I) and/or Formula (Ia) may be used in the treatment of proliferative and hyperproliferative diseases/conditions driven by ALK. Examples of proliferative and hyperproliferative diseases/conditions which may be driven by ALK include cancers such as: carcinoma; hematopoietic tumours of lymphoid lineage; hematopoietic tumors of myeloid lineage; tumors of mesenchymal origin;and other tumors, such as including melanoma, seminoma, tetratocarcinoma, neuroblastoma, and glioma.

In particular, compounds of Formula (I) and/or Formula (Ia) may be used for the treatment of non small cell lung cancer, breast cancer, neuroblastoma, anaplastic large cell lymphoma, esophageal squamous cell carcinoma, and inflammatory myofibroblastic tumors. In some embodiments, compounds of Formula (I) and/or Formula (Ia) may be used for the treatment of non small cell lung cancer. In some embodiments, compounds of Formula (I) and/or Formula (Ia) may be used for the treatment of breast cancer. In some embodiments, compounds of Formula (I) and/or Formula (Ia) may be used for the treatment of neuroblastoma. In some embodiments, compounds of Formula (I) and/or Formula (Ia) may be used for the treatment of anaplastic large cell lymphoma. In some embodiments, compounds of Formula (I) and/or Formula (Ia) may be used for the treatment of esophageal squamous cell carcinoma. In some embodiments, compounds of Formula (I) and/or Formula (Ia) may be used for the treatment of inflammatory myofibroblastic tumors.

The invention also relates to processes for the manufacture of compounds of Formula (I) and/or Formula (Ia), to pharmaceutical compositions containing them and to their use in the manufacture of medicaments for use in the production of an anti-cancer effect in warm-blooded animals such as man. Also in accordance with the present invention there are provided methods of using said compounds, and/or pharmaceutically acceptable salts thereof, for the treatment of cancer.

DETAILED DESCRIPTION OF THE INVENTION

I. Definitions

"ALKYL": As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only. In one aspect, "alkyl" may be "$C_{1-6}$alkyl." In another aspect, "alkyl" and "$C_{1-6}$alkyl" may be "$C_{1-4}$alkyl." In another aspect, "alkyl," "$C_{1-6}$alkyl," and "$C_{1-4}$alkyl" may be "$C_{1-3}$alkyl." In another aspect, "alkyl," "$C_{1-6}$alkyl," and "$C_{1-4}$alkyl," and "$C_{1-3}$alkyl" may be methyl. In another aspect, "alkyl," "$C_{1-6}$alkyl," and "$C_{1-4}$alkyl," and "$C_{1-3}$alkyl" may be gem-dimethyl.

"$C_{1-4}$ALKYL": As used herein the term "$C_{1-4}$alkyl" refers to both straight and branched chain saturated hydrocarbon radicals having one, two, three, or four carbon atoms. In some embodiments, "$C_{1-4}$alkyl" is "$C_1$alkyl". In some embodiments, "$C_{1-4}$alkyl" is "$C_2$alkyl". In some embodiments, "$C_{1-4}$alkyl" is "$C_3$alkyl". In some embodiments, "$C_{1-4}$alkyl" is "$C_4$alkyl".

"$C_{1-6}$ALKYL": As used herein the term "$C_{1-6}$alkyl" refers to both straight and branched chain saturated hydrocarbon radicals having one, two, three, four, five, or six carbon atoms. In some embodiments, "$C_{1-6}$alkyl" is "$C_1$alkyl". In some embodiments, "$C_{1-6}$alkyl" is "$C_2$alkyl". In some embodiments, "$C_{1-6}$alkyl" is "$C_3$alkyl". In some embodiments, "$C_{1-6}$alkyl" is "$C_4$alkyl". In some embodiments, "$C_{1-6}$alkyl" is "$C_5$alkyl". In some embodiments, "$C_{1-6}$alkyl" is "$C_6$alkyl".

"3- TO 6-MEMBERED CARBOCYCLYL": As used herein, the term "3- to 6-membered carbocyclyl" refers to a saturated, partially saturated, or unsaturated monocyclic carbon ring containing 3 to 6 ring atoms, of which one or more —$CH_2$— groups may be optionally replaced with a corresponding number of —C(O)— groups. Illustrative examples of "3- to 6-membered carbocyclyl" include cyclopropyl, cyclobutyl, cyclopentyl, oxocyclopentyl, cyclopentenyl, cyclohexyl, and phenyl.

"3- TO 5-MEMBERED CARBOCYCLYL": In one aspect, "carbocyclyl" and "3- to 6-membered carbocyclyl" may be "3- to 5-membered carbocyclyl." The term "3- to 5-

"C3-6CYCLOALKYL": In one aspect, "3- to 6-membered carbocyclyl" may be "$C_{3-6}$cycloalkyl." The term "$C_{3-6}$cycloalkyl" is intended to mean a saturated 3 to 6 membered monocyclic carbon ring. "$C_{3-6}$cycloalkyl" includes cyclopropyl, cyclobutyl, cyclopentyl and cyclohexyl, for example.

"EFFECTIVE AMOUNT": As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

In particular, an effective amount of a compound of Formula (I) and/or Formula (Ia) for use in the treatment of cancer is an amount sufficient to symptomatically relieve in a warm-blooded animal such as man, the symptoms of cancer and myeloproliferative diseases, to slow the progression of cancer and myeloproliferative diseases, or to reduce in patients with symptoms of cancer and myeloproliferative diseases the risk of getting worse.

"HALO": As used herein, the term "halo" refers to fluoro, chloro, bromo and iodo. In one aspect, the term "halo" may refer to fluoro, chloro, and bromo. In another aspect, the term "halo" may refer to fluoro and chloro. In still another aspect, the term "halo" may refer to fluoro. In still another aspect, the term "halo" may refer to chloro. In still another aspect, the term "halo" may refer to bromo.

"4- to 7-Membered Heterocyclic Ring":

The term "4- to 7-membered heterocyclic ring" as used in the phrase "$R^1$ and $R^2$ together with the nitrogen to which they are attached form a 4- to 7-membered heterocyclic ring" refers to a saturated or partially saturated monocyclic ring containing 4 to 7 ring atoms, of which one ring atom is the nitrogen indicated by the arrow below in Formula (I) and/or Formula (Ia):

Formula (Ia)

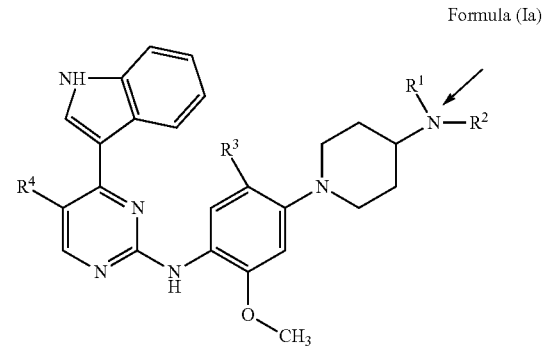

Formula (I)

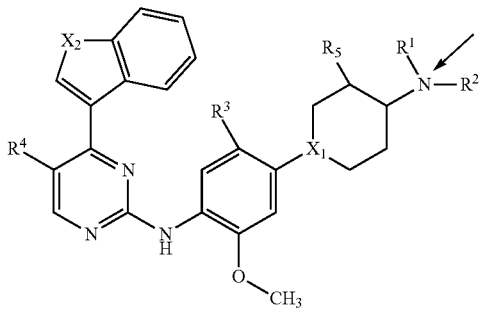

The ring may include, in addition to the indicated nitrogen, one or more heteroatoms selected from nitrogen, sulfur, and oxygen. One or more —CH$_2$— groups may be optionally replaced by a corresponding number of —C(O)— groups. Ring sulfur atoms may be optionally oxidized to form S-oxides. Illustrative examples of "4- to 7-membered heterocyclic ring" include azetidinyl, 1,4-diazepan-1-imidazolin-1-yl, imidazolidin-1-yl, pyrazolidin-1-yl, homopiperazin-1-yl, morpholino, 1,4-oxazepan-4-yl, piperazin-1-yl, piperidin-1-yl, pyrrolidin-1-yl, and thiomorpholino.

"4- TO 6-MEMBERED HETEROCYCLIC RING": In one aspect, "4- to 7-membered heterocyclic ring" may be "4- to 6-membered heterocyclic ring." The term "4- to 6-membered heterocyclic ring" refers to a saturated or partially saturated monocyclic ring containing 4 to 6 ring atoms, of which one ring atom is the nitrogen indicated by the arrow below in Formula (I) and/or Formula (Ia):

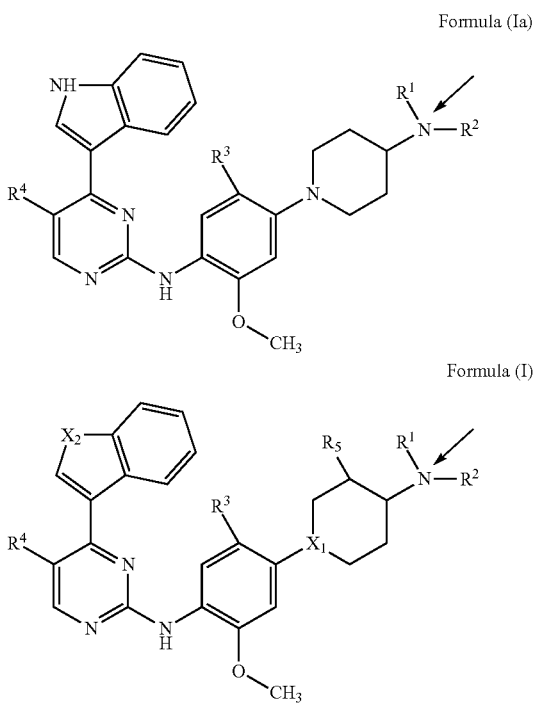

Formula (Ia)

Formula (I)

The ring may include, in addition to the indicated nitrogen, one or more heteroatoms selected from nitrogen, sulfur, and oxygen. One or more —CH$_2$— groups may be optionally replaced by a corresponding number of —C(O)— groups. Ring sulfur atoms may be optionally oxidized to form S-oxides. Illustrative examples of "4- to 6-membered heterocyclic ring" include azetidinyl, imidazolin-1-yl, imidazolidin-1-yl, pyrazolidin-1-yl, morpholino, piperazin-1-yl, piperidin-1-yl, pyrrolidin-1-yl, and thiomorpholino.

Where a particular R group (e.g. $R^1$, $R^{20}$, etc.) is present in a compound of Formula (I) and/or Formula (Ia) more than once, it is intended that each selection for that R group is independent at each occurrence of any selection at any other occurrence. For example, a group designated "—N(R)$_2$" would be intended to encompass: 1) those —N(R)$_2$ groups in which both R substituents are the same, such as those in which both R substituents are, for example, C$_{1-6}$alkyl; and 2) those —N(R)$_2$ groups in which each R substituent is different, such as those in which one R substituent is, for example, H, and the other R substituent is, for example, carbocyclyl.

Unless specifically stated, the bonding atom of a group may be any suitable atom of that group; for example, propyl includes prop-1-yl and prop-2-yl.

"4- TO 7-MEMBERED HETEROCYCLYL": The term "4- to 7-membered heterocyclyl" refers to a saturated, partially saturated, or unsaturated monocyclic ring containing 4 to 7 ring atoms, of which at least one ring atom is selected from nitrogen, sulfur, and oxygen, and of which a —CH$_2$— group may be optionally replaced by a —C(O)— group. Unless otherwise specified, "4- to 7-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "4- to 7-membered heterocyclyl" include azetidin-1-yl, 1,4-diazepanyl, dioxidotetrahydrothiophenyl, 2,4-dioxoimidazolidinyl, 3,5-dioxopiperidinyl, furanyl, homopiperazin-1-yl, imidazolyl, isothiazolyl, isoxazolyl, morpholinyl, 1,4-oxazepanyl, oxazolyl, oxetanyl, oxoimidazolidinyl, 3-oxo-1-piperazinyl, 2-oxopyrrolidinyl, 2-oxotetrahydrofuranyl, oxo-1,3-thiazolidinyl, piperazinyl, piperidyl, 2H-pyranyl, pyrazolyl, pyridinyl, pyrrolyl, pyrrolidinyl, pyrimidinyl, pyrazinyl, pyrazolyl, pyridazinyl, tetrahydrofuranyl, tetrahydropyranyl, thiazolyl, 1,3,4-thiadiazolyl, thiazolidinyl, thiomorpholinyl, thiophenyl, 4H-1,2,4-triazolyl, and pyridine-N-oxidyl.

"4- TO 6-MEMBERED HETEROCYCLYL": In one aspect, "4- to 7-membered heterocyclyl" may be "4- to 6-membered heterocyclyl." The term "4- to 6-membered heterocyclyl" refers to a saturated, partially saturated, or unsaturated, monocyclic ring containing 4 to 6 ring atoms, of which at least one ring atom is selected from nitrogen, sulfur, and oxygen, and of which a —CH$_2$— group may be optionally replaced by a —C(O)— group. Unless otherwise specified, "4- to 6-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "4- to 6-membered heterocyclyl" include azetidin-1-yl, dioxidotetrahydrothiophenyl, 2,4-dioxoimidazolidinyl, 3,5-dioxopiperidinyl, furanyl, imidazolyl, isothiazolyl, isoxazolyl, morpholinyl, oxazolyl, oxetanyl, oxoimidazolidinyl, 3-oxo-1-piperazinyl, 2-oxopyrrolidinyl, 2-oxotetrahydrofuranyl, oxo-1,3-thiazolidinyl, piperazinyl, piperidyl, 2H-pyranyl, pyrazolyl, pyridinyl, pyrrolyl, pyrrolidinyl, pyrimidinyl, pyrazinyl, pyrazolyl, pyridazinyl, tetrahydrofuranyl, tetrahydropyranyl, thiazolyl, 1,3,4-thiadiazolyl, thiazolidinyl, thiomorpholinyl, thiophenyl, 4H-1,2,4-triazolyl, and pyridine-N-oxidyl.

"4- OR 5-MEMBERED HETEROCYCLYL": In one aspect, "4- to 7-membered heterocyclyl" and "4- to 6-membered heterocyclyl" may be "4- or 5-membered heterocyclyl." The term "4- or 5-membered heterocyclyl" is intended to refer to a saturated, partially saturated, or unsaturated monocyclic ring containing 4 or 5 ring atoms, of which at least one ring atom is selected from nitrogen, sulfur, and oxygen. Unless otherwise specified, "4- or 5-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "4- or 5-membered heteroaryl" include azetidinyl, furanyl, imidazolyl, isothiazolyl, isoxazole, oxetanyl, oxazolyl, pyrazolyl, pyrrolidinyl, pyrrolyl, tetrahydrofuranyl, 1,3,4-thiadiazolyl, thiazolidinyl, thiazolyl, thiophenyl, and 4H-1,2,4-triazolyl.

"4-MEMBERED HETEROCYCLYL": In one aspect, "4- to 7-membered heterocyclyl" and "4- to 6-membered heterocyclyl" may be "4-membered heterocyclyl." The term "4-membered heterocyclyl" is intended to refer to a saturated, partially saturated, or unsaturated monocyclic ring containing 4 ring atoms, of which at least one ring atom is selected from nitrogen, sulfur, and oxygen. Unless otherwise specified, "4-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "4-membered heterocyclyl" include azetidinyl and oxetanyl.

"LEAVING GROUP": As used herein, the phrase "leaving group" is intended to refer to groups readily displaceable by a nucleophile such as an amine nucleophile, and alcohol nucleophile, or a thiol nucleophile. Examples of suitable leaving groups include halo, such as chloro and bromo, and sulfonyloxy group, such as methanesulfonyloxy and toluene-4-sulfonyloxy.

"OPTIONALLY SUBSTITUTED": As used herein, the phrase "optionally substituted," indicates that substitution is optional and therefore it is possible for the designated group to be either substituted or unsubstituted. In the event a substitution is desired, any number of hydrogens on the designated group may be replaced with a selection from the indicated substituents, provided that the normal valency of the atoms on a particular substituent is not exceeded, and that the substitution results in a stable compound.

In one aspect, when a particular group is designated as being optionally substituted with "one or more" substituents, the particular group may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

"PHARMACEUTICALLY ACCEPTABLE": As used herein, the term "pharmaceutically acceptable" refers to those compounds, materials, compositions, and/or dosage forms which are, within the scope of sound medical judgment, suitable for use in contact with the tissues of human beings and animals without excessive/undue toxicity, irritation, allergic response, or other problem or complication, commensurate with a reasonable benefit/risk ratio.

"PHARMACEUTICALLY ACCEPTABLE SALT(S)": As used herein, the term "pharmaceutically acceptable salt" refers to those salts which are, within the scope of sound medical judgment, suitable for use in contact with the tissues of human beings and animals without excessive/undue toxicity, irritation, allergic response, or other problem or complication, commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, pp. 1-19, which is incorporated herein by reference.

Compounds of Formula (I) and/or Formula (Ia) may form stable pharmaceutically acceptable acid or base salts, and in such cases administration of a compound as a salt may be appropriate.

Examples of acid addition salts include acetate, adipate, ascorbate, benzoate, benzenesulfonate, besylate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, malonate, methanesulfonate, meglumine, mesylate, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. In some embodiments, the acid addition salt is acetate. In some embodiments, the acid addition salt is besylate. In some embodiments, the acid addition salt is citrate. In some embodiments, the acid addition salt is fumarate. In some embodiments, the acid addition salt is hydrochloride. In some embodiments, the acid addition salt is mesylate. In some embodiments, the acid addition salt is phosphate. In some embodiments, the acid addition salt is malonate. In some embodiments, the acid addition salt is succinate. In some embodiments, the acid addition salt is sulfate. In some embodiments, the acid addition salt is tartrate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

Salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

"PROTECTING GROUP": As used herein, the term "protecting group" is intended to refer to those groups used to prevent selected reactive groups (such as carboxy, amino, hydroxy, and mercapto groups) from undergoing undesired reactions.

Illustrative examples of suitable protecting groups for a hydroxy group include, but are not limited to, an acyl group; alkanoyl groups such as acetyl; aroyl groups, such as benzoyl; silyl groups, such as trimethylsilyl; and arylmethyl groups, such as benzyl. The deprotection conditions for the above hydroxy protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

Illustrative examples of suitable protecting groups for an amino group include, but are not limited to, acyl groups; alkanoyl groups such as acetyl; alkoxycarbonyl groups, such as methoxycarbonyl, ethoxycarbonyl, and t-butoxycarbonyl; arylmethoxycarbonyl groups, such as benzyloxycarbonyl; and aroyl groups, such benzoyl. The deprotection conditions for the above amino protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron trichloride). A suitable alternative protecting group for a primary amino group is, for example, a phthaloyl group, which may be removed by treatment with an alkylamine, for example dimethylaminopropylamine or 2-hydroxyethylamine, or with hydrazine. Another suitable protecting group for an amine is, for example, a cyclic ether such as tetrahydrofuran, which may be removed by treatment with a suitable acid such as trifluoroacetic acid.

The protecting groups may be removed at any convenient stage in the synthesis using conventional techniques well known in the chemical art, or they may be removed during a later reaction step or work-up.

With reference to substituent $R^1$ for illustrative purposes, the following substituent definitions have the indicated structures:

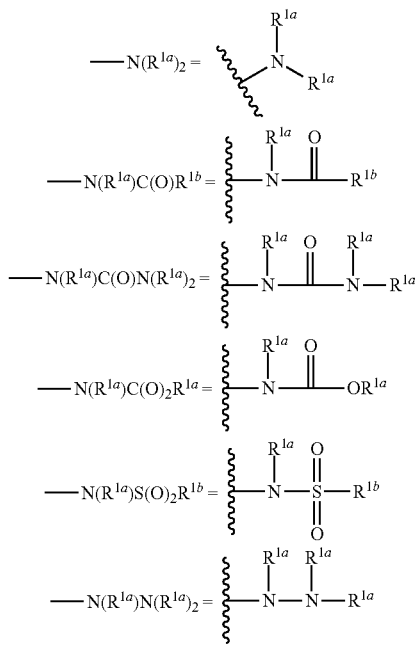

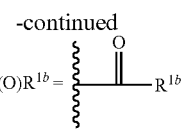
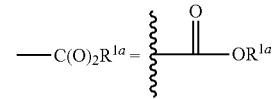
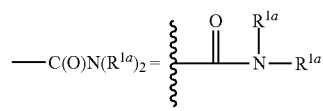
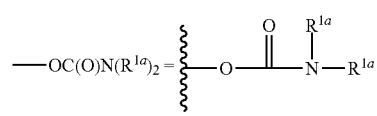
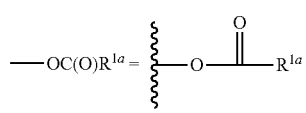
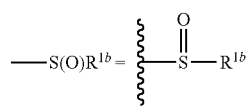
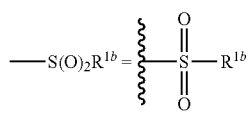
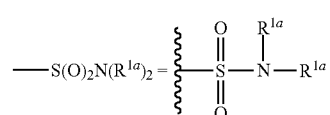
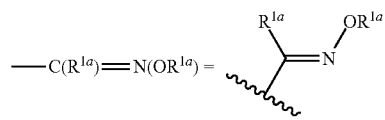
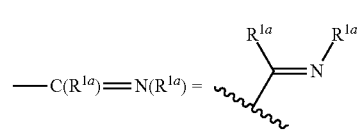

Compounds discussed herein in many instances were named and/or checked with ACD/Name by ACD/Labs®.

"TREAT", "TREATING" or "TREATMENT": The terms "treat", "treating" or "treatment" include administering a therapeutically effective amount of a compound sufficient to redudce or eliminate at least one symptom of the state, disease or disorder, e.g., ALK-related conditions and diseases, e.g., cancer.

II. Compounds of the Present Invention

Compounds provided by the present invention include those described generally above, and are further illustrated by all classes, subclasses and species of each of these compounds disclosed herein.

The present invention relates to compounds of Formula (I):

Formula (I)

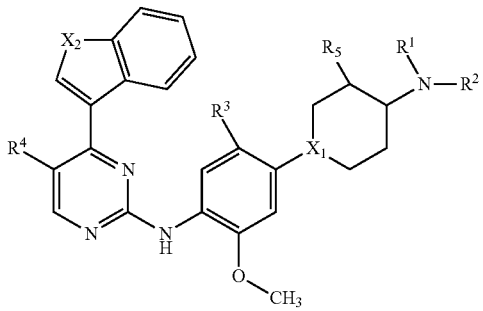

and/or to pharmaceutically acceptable salts thereof, wherein:
$X_1$ is selected from

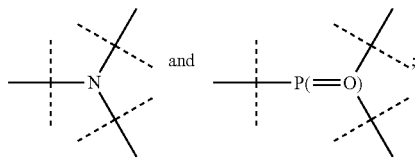

$X_2$ is selected from —NH— and —N($C_{1-4}$alkyl)-;
$R^1$ is selected from H and $C_{1-4}$alkyl, wherein said $C_{1-4}$alkyl is optionally substituted with one or more hydroxy;
$R^2$ is selected from H, $C_{1-4}$alkyl, $C_{3-6}$cycloalkyl, and 4- to 7-membered heterocyclyl, wherein said $C_{1-4}$alkyl is optionally substituted with one or more hydroxy;
or $R^1$ and $R^2$ together with the nitrogen to which they are attached form a 4- to 7-membered heterocyclic ring, wherein said 4- to 7-membered heterocyclic ring is optionally substituted on carbon with one or more $R^{20}$, and wherein if said 4- to 7-membered heterocyclic ring contains an —NH— moiety, that nitrogen is optionally substituted with $R^{20*}$;
$R^3$ is selected from H, halo, and methyl;
$R^4$ is selected from halo, —CN, methyl, and trifluoromethyl;
$R^5$ is selected from H, halo, and $C_{1-4}$ alkyl;
$R^{20}$ in each occurrence is selected from halo and $C_{1-6}$alkyl;
$R^{20*}$ is selected from $C_{1-6}$alkyl, 3- to 6-membered carbocyclyl, —S(O)$R^{20b}$, and —S(O)$_2R^{20b}$; and
$R^{20b}$ in each occurrence is independently selected from $C_{1-6}$alkyl and 3- to 6-membered carbocyclyl.

In certain embodiments, the present invention provides a compound of formula (I):

Formula (I)

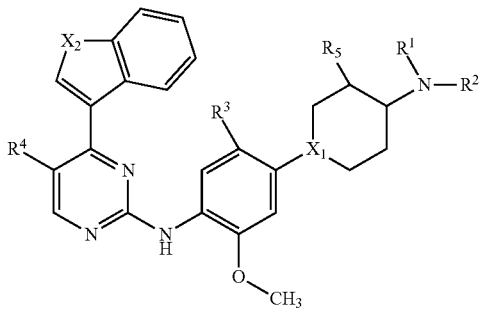

and/or a pharmaceutically acceptable salt thereof, wherein:
$X_1$ is selected from

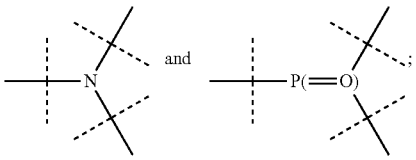

$X_2$ is selected from —NH— and —N($C_{1-4}$ alkyl)-;
$R^1$ is selected from H and $C_{1-2}$alkyl, wherein said $C_{1-2}$alkyl is optionally substituted with one or more hydroxy;
$R^2$ is selected from H, $C_{1-2}$alkyl, $C_3$cycloalkyl, and 4-membered heterocyclyl, wherein said $C_{1-2}$alkyl is optionally substituted with one or more hydroxy;
or $R^1$ and $R^2$ together with the nitrogen to which they are attached form a 5- to 6-membered heterocyclic ring, wherein said 5- to 6-membered heterocyclic ring is optionally substituted on carbon with one or more $R^{20}$, and wherein if said 5- to 6-membered heterocyclic ring contains an —NH— moiety, that nitrogen is optionally substituted with $R^{20*}$;
$R^3$ is selected from H, halo, and methyl;
$R^4$ is selected from halo, —CN, methyl, and trifluoromethyl;
$R^5$ is selected from H, halo, and $C_{1-2}$ alkyl;
$R^{20}$ in each occurrence is selected from halo and methyl;
$R^{20*}$ is selected from $C_{1-3}$alkyl and —S(O)$_2R^{20b}$; and
$R^{20b}$ is methyl.

In certain embodiments, the present invention provides a compound of formula (Ia):

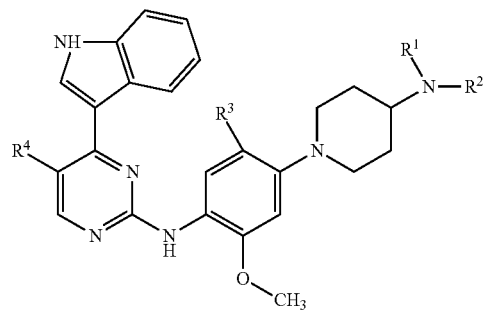

Formula (Ia)

and/or to pharmaceutically acceptable salts thereof, wherein:
$R^1$ is selected from H and $C_{1-4}$alkyl, wherein said $C_{1-4}$alkyl is optionally substituted with one or more hydroxy;
$R^2$ is selected from H, $C_{1-4}$alkyl, $C_{3-6}$cycloalkyl, and 4- to 7-membered heterocyclyl, wherein said $C_{1-4}$alkyl is optionally substituted with one or more hydroxy;
or $R^1$ and $R^2$ together with the nitrogen to which they are attached form a 4- to 7-membered heterocyclic ring, wherein said 4- to 7-membered heterocyclic ring is optionally substituted on carbon with one or more $R^{20}$, and wherein if said 4- to 7-membered heterocyclic ring contains an —NH— moiety, that nitrogen is optionally substituted with $R^{20*}$;
$R^3$ is selected from H, halo, and methyl;
$R^4$ is selected from halo, —CN, methyl, and trifluoromethyl;
$R^{20}$ in each occurrence is independently selected from halo and $C_{1-6}$alkyl;

$R^{20*}$ is selected from $C_{1-6}$alkyl, 3- to 6-membered carbocyclyl, —S(O)$R^{20b}$, and —S(O)$_2R^{20b}$; and $R^{20b}$ in each occurrence is independently selected from $C_{1-6}$alkyl and 3- to 6-membered carbocyclyl.

Additional embodiments of the invention are as follows. These additional embodiments relate to compounds of Formula (I) and/or Formula (Ia) and/or pharmaceutically acceptable salts thereof. Such specific substituents may be used, where appropriate, with any of the definitions, claims or embodiments defined hereinbefore or hereinafter.

$X_1$ Embodiments

As generally defined above, $X_1$ is selected from

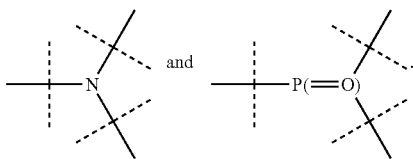

In some embodiments, $X_1$ is

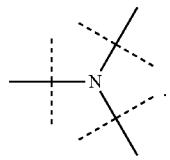

In some embodiments, $X_1$ is

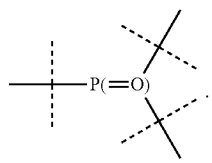

$X_2$ Embodiments

As generally defined above, $X_2$ is selected from —NH— and —N($C_{1-4}$ alkyl)-. In some embodiments, $X_2$ is —NH—. In some embodiments, $X_2$ is —N($C_{1-4}$ alkyl)-.

$R^1$ Embodiments

As generally defined above, $R^1$ is selected from H and $C_{1-4}$alkyl, wherein said $C_{1-4}$alkyl is optionally substituted with one or more hydroxy.

In one aspect, $R^1$ is selected from H and $C_{1-4}$alkyl.

In another aspect, $R^1$ is selected from H and methyl.

In some embodiments, $R^1$ is H. In some embodiments, $R^1$ is $C_{1-4}$alkyl. In some embodiments, $R^1$ is methyl. In some embodiments, $R^1$ is $C_2$alkyl. In some embodiments, $R^1$ is $C_3$alkyl. In some embodiments, $R^1$ is $C_4$alkyl. In some embodiments, $R^1$ is $C_2$alkyl substituted with a hydroxyl.

$R^2$ Embodiments

As generally defined above, $R^2$ is selected from H, $C_{1-4}$alkyl, $C_{3-6}$cycloalkyl, and 4- to 7-membered heterocyclyl, wherein said $C_{1-4}$alkyl is optionally substituted with one or more hydroxy.

In one aspect, $R^2$ is selected from H, $C_{1-4}$alkyl; $C_{3-6}$cycloalkyl, and 4- or 5-membered heterocyclyl.

In another aspect, $R^2$ is selected from H, methyl, cyclopropyl, and oxetanyl.

In some embodiments, $R^2$ is H. In some embodiments, $R^2$ is $C_{1-4}$alkyl. In some embodiments, $R^2$ is methyl. In some embodiments, $R^2$ is $C_2$alkyl substituted with a hydroxy. In some embodiments, $R^2$ is $C_{3-6}$cycloalkyl. In some embodiments, $R^2$ is a 4- to 7-membered heterocyclyl. In some embodiments, $R^2$ is a 4-membered heterocyclyl. In some embodiments, $R^2$ is an oxetanyl.

$R^1$ and $R^2$ Embodiments

As generally defined above, $R^1$ and $R^2$ may together with the nitrogen to which they are attached form a 4- to 7-membered heterocyclic ring, wherein said 4- to 7-membered heterocyclic ring is optionally substituted on carbon with one or more $R^{20}$, and wherein if said 4- to 7-membered heterocyclic ring contains an —NH— moiety, that nitrogen is optionally substituted with $R^{20*}$.

In one aspect, $R^1$ is selected from H and $C_{1-4}$alkyl; and $R^2$ is selected from H, $C_{1-4}$alkyl; $C_{3-6}$cycloalkyl, and 4- or 5-membered heterocyclyl.

In another aspect, $R^1$ is selected from H and methyl; and $R^2$ is selected from H, methyl, cyclopropyl, and oxetanyl.

In another aspect, $R^1$ and $R^2$ together with the nitrogen to which they are attached form a 5- or 6-membered heterocyclic ring, wherein said 5- or 6-membered heterocyclic ring is optionally substituted on carbon with one or more $R^{20}$, and wherein if said 5- or 6-membered heterocyclic ring contains an —NH— moiety, that nitrogen is optionally substituted with $R^{20*}$; $R^{20}$ in each occurrence is independently selected from halo and $C_{1-3}$alkyl; and $R^{20*}$ is $C_{1-3}$alkyl.

In another aspect, $R^1$ and $R^2$ together with the nitrogen to which they are attached form a morpholino ring, a piperazinyl ring or a pyrrolidinyl ring, wherein said morpholino ring, piperazinyl ring and pyrrolidinyl ring are optionally substituted on carbon with one or more $R^{20}$, and wherein said piperazinyl ring is optionally substituted on nitrogen with $R^{20*}$; $R^{20}$ in each occurrence is independently selected from fluoro and methyl; and $R^{20*}$ is selected from methyl and isopropyl.

In some embodiments, $R^1$ and $R^2$ together with the nitrogen to which they are attached form piperazinyl. In some embodiments, $R^1$ and $R^2$ together with the nitrogen to which they are attached form 1-methylpiperazinyl. In some embodiments, $R^1$ and $R^2$ together with the nitrogen to which they are attached form 4-methylpiperazinyl. In some embodiments, $R^1$ and $R^2$ together with the nitrogen to which they are attached form 1-(methylsulfonyl)piperazinyl. In some embodiments, $R^1$ and $R^2$ together with the nitrogen to which they are attached form fluorocyclopentanyl. In some embodiments, $R^1$ and $R^2$ together with the nitrogen to which they are attached form 1-isopropylpiperazinyl. In some embodiments, $R^1$ and $R^2$ together with the nitrogen to which they are attached form 2,6-dimethylmorpholinyl.

$R^{20}$ Embodiments

As generally defined above, $R^{20}$ in each occurrence is selected from halo and $C_{1-6}$alkyl.

In some embodiments, $R^{20}$ is methyl. In some embodiments, $R^{20}$ is fluoro.

$R^{20*}$

As generally defined above, $R^{20*}$ is selected from $C_{1-6}$alkyl, 3- to 6-membered carbocyclyl, —S(O)$R^{20b}$, and —S(O)$_2R^{20b}$.

In some embodiments, $R^{20*}$ is methyl. In some embodiments, $R^{20*}$ is —S(O)$_2R^{20b}$. In some embodiments, $R^{20*}$ is $C_3$alkyl. In some embodiments, $R^{20*}$ is isopropyl.

$R^{20b}$ Embodiments

As generally defined above, $R^{20b}$ in each occurrence is independently selected from $C_{1-6}$alkyl and 3- to 6-membered carbocyclyl.

In some embodiments, $R^{20b}$ is methyl.

$R^3$ Embodiments

As generally defined above, $R^3$ is selected from H, halo, and methyl.

In one aspect, $R^3$ is selected from H and methyl.

In some embodiments $R^3$ is H. In some embodiments $R^3$ is methyl. In some embodiments $R^3$ is halo. In some embodiments $R^3$ is fluoro. In some embodiments $R^3$ is chloro.

$R^4$ Embodiments

As generally defined above, $R^4$ is selected from halo, —CN, methyl, and trifluoromethyl.

In one aspect, $R^4$ is selected from halo and methyl.

In another aspect, $R^4$ is selected from chloro and methyl.

In some embodiments, $R^4$ is halo. In some embodiments, $R^4$ is bromo. In some embodiments, $R^4$ is chloro. In some embodiments, $R^4$ is fluoro. In some embodiments, $R^4$ is —CN. In some embodiments, $R^4$ is methyl. In some embodiments, $R^4$ is trifluoromethyl.

$R^5$ Embodiments

As generally defined above, $R^5$ is selected from H, halo, and $C_{1-4}$ alkyl.

In one aspect, $R^5$ is selected from H, halo, and $C_{1-4}$ alkyl. In another aspect, $R^5$ is selected from H. In another aspect $R^5$ is selected from halo. In another aspect, $R^5$ is selected from fluoro. In another aspect, $R^5$ is selected from $C_{1-4}$ alkyl. In another aspect, $R^5$ is selected from $C_{1-2}$ alkyl. In another aspect, $R^5$ is selected from $C_2$ alkyl. In another aspect, $R^5$ is selected from gem dimethyl.

In some embodiments, $R^5$ is H. In some embodiments, $R^5$ is $C_2$alkyl. In some embodiments, $R^5$ is dimethyl. In some embodiments, $R^5$ is $C_2$ alkyl. In some embodiments, $R^5$ is dimethyl. In some embodiments, $R^5$ is gem dimethyl. In some embodiments, $R^5$ is halo. In some embodiments, $R^5$ is fluoro.

$R^1$, $R^2$, $R^3$, and $R^4$ Embodiments

In one aspect, $R^1$ and $R^2$ together with the nitrogen to which they are attached form a 4- to 7-membered heterocyclic ring, wherein said 4- to 7-membered heterocyclic ring is optionally substituted on carbon with one or more $R^{20}$, and wherein if said 4- to 7-membered heterocyclic ring contains an —NH— moiety, that nitrogen is optionally substituted with $R^{20*}$;

$R^3$ is selected from H, halo, and methyl;

$R^4$ is selected from halo, —CN, methyl, and trifluoromethyl;

$R^{20}$ in each occurrence is independently selected from halo and $C_{1-4}$alkyl;

$R^{20*}$ is selected from $C_{1-4}$alkyl, 3- to 6-membered carbocyclyl, —S(O)$R^{20b}$, and —S(O)$_2R^{20b}$; and $R^{20b}$ in each occurrence is independently selected from $C_{1-6}$alkyl and 3- to 6-membered carbocyclyl.

In one aspect, $R^1$ and $R^2$ together with the nitrogen to which they are attached form a 5- or 6-membered heterocyclic ring, wherein said 5- or 6-membered heterocyclic ring is optionally substituted on carbon with one or more $R^{20}$, and wherein if said 5- or 6-membered heterocyclic ring contains an —NH— moiety, that nitrogen is optionally substituted with $R^{20*}$;

$R^3$ is selected from H, halo, and methyl;

$R^4$ is selected from halo, —CN, methyl, and trifluoromethyl;

$R^{20}$ in each occurrence is independently selected from halo and $C_{1-3}$alkyl; and $R^{20*}$ is $C_{1-3}$alkyl.

In one aspect, $R^1$ and $R^2$ together with the nitrogen to which they are attached form a 5- or 6-membered heterocyclic ring, wherein if said 5- or 6-membered heterocyclic ring contains an —NH— moiety, that nitrogen is optionally substituted with $R^{20*}$;

$R^3$ is selected from H, halo, and methyl;

$R^4$ is selected from halo, —CN, methyl, and trifluoromethyl; and $R^{20*}$ is $C_{1-3}$ alkyl.

In another aspect of compounds of Formula (I) and/or Formula (Ia), and/or pharmaceutically acceptable salts thereof, $R^1$ is selected from H and $C_{1-4}$alkyl, wherein said $C_{1-4}$alkyl is optionally substituted with one or more hydroxy;

$R^2$ is selected from H, $C_{1-4}$alkyl, $C_{3-6}$cycloalkyl, and 4- to 7-membered heterocyclyl, wherein said $C_{1-4}$alkyl is optionally substituted with one or more hydroxy;

$R^3$ is selected from H, halo, and methyl; and $R^4$ is selected from halo, —CN, methyl, and trifluoromethyl.

In one aspect, $R^1$ is selected from H and $C_{1-4}$alkyl.

$R^2$ is selected from H, $C_{1-4}$alkyl; $C_{3-6}$cycloalkyl, and 4- or 5-membered heterocyclyl.

$R^3$ is selected from H, halo, and methyl; and $R^4$ is selected from halo, —CN, methyl, and trifluoromethyl.

$X_1$, $X_2$, $R^1$, $R^2$, $R^3$, and $R^4$ Embodiments

In one aspect, $X_1$ is

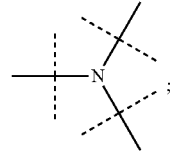

$X_2$ is —NH—; $R^1$ is H; $R^2$ is H; or $R^1$ and $R^2$ together with the nitrogen to which they are attached form a 4- to 7-membered heterocyclic ring, wherein said 4- to 7-membered heterocyclic ring contains an —NH— moiety optionally substituted with $R^{20*}$; $R^{20*}$ is $C_{1-6}$alkyl; $R^3$ is H; $R^4$ is selected from halo and methyl; and $R^5$ is H.

In one aspect, $X_1$ is

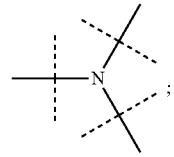

$X_2$ is —NH—; $R^1$ is H; $R^2$ is H; $R^3$ is H; $R^4$ is halo; and $R^5$ is H.

In one aspect, $X_1$ is

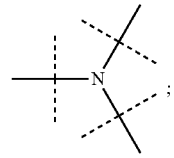

$X_2$ is —NH—; $R^1$ is H; $R^2$ is H; $R^3$ is H; $R^4$ is chloro; and $R^5$ is H.

In one aspect, $X_1$ is

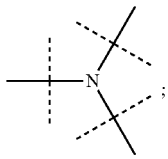

$X_2$ is —NH—; $R^1$ and $R^2$ together with the nitrogen to which they are attached form a 4- to 7-membered heterocyclic ring, wherein said 4- to 7-membered heterocyclic ring contains an —NH— moiety optionally substituted with $R^{20*}$; $R^{20*}$ is $C_1$alkyl; $R^3$ is H; $R^4$ is methyl; and $R^5$ is H.

In one aspect, $X_1$ is

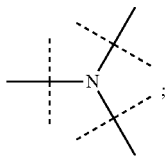

$X_2$ is —NH—; $R^1$ and $R^2$ together with the nitrogen to which they are attached form a 6-membered heterocyclic ring, wherein said 6-membered heterocyclic ring contains an —NH— moiety optionally substituted with $C_1$alkyl; $R^3$ is H; $R^4$ is methyl; and $R^5$ is H.

In one aspect, $X_1$ is

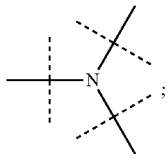

$X_2$ is —NH—; $R^1$ and $R^2$ together with the nitrogen to which they are attached form a piperazinyl ring, wherein said piperazinyl ring is optionally substituted with $C_1$alkyl; $R^3$ is H; $R^4$ is methyl; and $R^5$ is H.

In one aspect, $X_1$ is

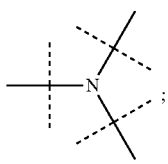

$X_2$ is —NH—; $R^1$ and $R^2$ together with the nitrogen to which they are attached form 4-methylpiperazinyl; $R^3$ is H; $R^4$ is methyl; and $R^5$ is H.

In one aspect, $X_1$ is

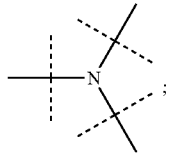

$X_2$ is —NH—; $R^1$ and $R^2$ together with the nitrogen to which they are attached form a 4- to 7-membered heterocyclic ring, wherein said 4- to 7-membered heterocyclic ring contains an —NH— moiety optionally substituted with $R^{20*}$; $R^{20*}$ is $C_1$alkyl; $R^3$ is H; $R^4$ is halo; and $R^5$ is H.

In one aspect, $X_1$ is

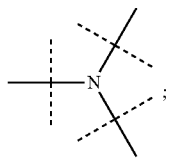

$X_2$ is —NH—; $R^1$ and $R^2$ together with the nitrogen to which they are attached form a 4- to 7-membered heterocyclic ring, wherein said 4- to 7-membered heterocyclic ring contains an —NH— moiety optionally substituted with $R^{20*}$; $R^{20*}$ is $C_1$alkyl; $R^3$ is H; $R^4$ is chloro; and $R^5$ is H.

In one aspect, $X_1$ is

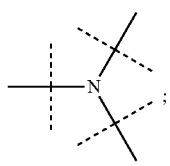

$X_2$ is —NH—; $R^1$ and $R^2$ together with the nitrogen to which they are attached form a 6-membered heterocyclic ring, wherein said 6-membered heterocyclic ring contains an —NH— moiety optionally substituted with $C_1$alkyl; $R^3$ is H; $R^4$ is chloro; and $R^5$ is H.

In one aspect, $X_1$ is

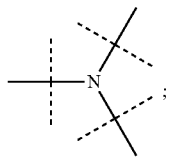

$X_2$ is —NH—; $R^1$ and $R^2$ together with the nitrogen to which they are attached form a piperazinyl ring, wherein said piperazinyl ring is optionally substituted with $C_1$alkyl; $R^4$ is chloro; and $R^5$ is H.

In one aspect, $X_1$ is

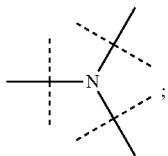

$X_2$ is —NH—; $R^1$ and $R^2$ together with the nitrogen to which they are attached form 4-methylpiperazinyl; $R^3$ is H; $R^4$ is chloro; and $R^5$ is H.

Also provided herein is:

N-(4-(4-Aminopiperidin-1-yl)-2-methoxyphenyl)-5-chloro-4-(1H-indol-3-yl)pyrimidin-2-amine as the trifluoroacetic acid salt;

5-Chloro-4-(1H-indol-3-yl)-N-(2-methoxy-4-(4-(methylamino)piperidin-1-yl)phenyl)pyrimidin-2-amine as the trifluoroacetic acid salt;

5-Chloro-4-(1H-indol-3-yl)-N-(2-methoxy-4-(4-(piperazin-1-yl)piperidin-1-yl)phenyl)pyrimidin-2-amine;

4-(1H-Indol-3-yl)-N-(2-methoxy-4-(4-(methylamino)piperidin-1-yl)phenyl)-5-methylpyrimidin-2-amine;

N-(4-(4-Aminopiperidin-1-yl)-2-methoxyphenyl)-4-(1H-indol-3-yl)-5-methylpyrimidin-2-amine as the trifluoroacetic acid salt;

5-Chloro-N-(4-(4-(cyclopropylamino)piperidin-1-yl)-2-methoxyphenyl)-4-(1H-indol-3-yl)pyrimidin-2-amine as the trifluoroacetic acid salt;

5-Fluoro-4-(1H-Indol-3-yl)-N-(2-methoxy-4-(4-(4-methylpiperazin-1-yl)piperidin-1-yl)phenyl)pyrimidin-2-amine as the trifluoroacetic acid salt;

4-(1H-Indol-3-yl)-N-(2-methoxy-4-(4-(4-methylpiperazin-1-yl)piperidin-1-yl)phenyl)-5-(trifluoromethyl)pyrimidin-2-amine;

4-(1H-Indol-3-yl)-N-(2-methoxy-4-(4-(4-methylpiperazin-1-yl)piperidin-1-yl)phenyl)-5-methylpyrimidin-2-amine;

5-Chloro-4-(1H-indol-3-yl)-N-(2-methoxy-4-(4-(4-methylpiperazin-1-yl)piperidin-1-yl)phenyl)pyrimidin-2-amine;

N-(4-(4-(Dimethylamino)piperidin-1-yl)-2-methoxyphenyl)-4-(1H-indol-3-yl)-5-methylpyrimidin-2-amine;

5-Chloro-N-(4-(4-(dimethylamino)piperidin-1-yl)-2-methoxyphenyl)-4-(1H-indol-3-yl)pyrimidin-2-amine;

N-(4-(4-(Dimethylamino)piperidin-1-yl)-2-methoxyphenyl)-5-fluoro-4-(1H-indol-3-yl)pyrimidin-2-amine;

5-Chloro-4-(1H-indol-3-yl)-N-(2-methoxy-5-methyl-4-(4-(4-methylpiperazin-1-yl)piperidin-1-yl)phenyl)pyrimidin-2-amine;

4-(1H-Indol-3-yl)-N-(2-methoxy-5-methyl-4-(4-(4-methylpiperazin-1-yl)piperidin-1-yl)phenyl)-5-methylpyrimidin-2-amine;

5-Chloro-N-(4-(4-(dimethylamino)piperidin-1-yl)-2-methoxy-5-methylphenyl)-4-(1H-indol-3-yl)pyrimidin-2-amine;

N-(4-(4-(Dimethylamino)piperidin-1-yl)-2-methoxy-5-methylphenyl)-4-(1H-indol-3-yl)-5-methylpyrimidin-2-amine;

N-(4-(4-Aminopiperidin-1-yl)-2-methoxy-5-methylphenyl)-5-chloro-4-(1H-indol-3-yl)pyrimidin-2-amine;

N-(4-(4-aminopiperidin-1-yl)-2-methoxy-5-methylphenyl)-4-(1H-indol-3-yl)-5-methylpyrimidin-2-amine;

2-(1-(4-(5-Chloro-4-(1H-indol-3-yl)pyrimidin-2-ylamino)-3-methoxyphenyl)piperidin-4-ylamino)ethanol;

5-Chloro-4-(1H-indol-3-yl)-N-(2-methoxy-4-{4-[4-(methylsulfonyl)piperazin-1-yl]piperidin-1-yl}phenyl)pyrimidin-2-amine as the trifluoroacetic acid salt;

5-Chloro-N-(4-{4-[(3R)-3-fluoropyrrolidin-1-yl]piperidin-1-yl}-2-methoxyphenyl)-4-(1H-indol-3-yl)pyrimidin-2-amine as the trifluoroacetic acid salt;

5-Chloro-4-(1H-indol-3-yl)-N-(4-(4-(4-isopropylpiperazin-1-yl)piperidin-1-yl)-2-methoxyphenyl)pyrimidin-2-amine as the trifluoroacetic acid salt;

5-Chloro-N-(4-(4-((2S,6R)-2,6-dimethylmorpholino)piperidin-1-yl)-2-methoxyphenyl)-4-(1H-indol-3-yl)pyrimidin-2-amine as the trifluoroacetic acid salt;

(R)-5-Chloro-N-(4-(4-(3-fluoropyrrolidin-1-yl)piperidin-1-yl)-2-methoxy-5-methylphenyl)-4-(1H-indol-3-yl)pyrimidin-2-amine;

5-Chloro-4-(1H-indol-3-yl)-N-(2-methoxy-4-(4-(oxetan-3-ylamino)piperidin-1-yl)phenyl)pyrimidin-2-amine as the trifluoroacetic acid salt;

(5-Bromo-4-(1H-indol-3-yl)-N-(2-methoxy-4-(4-(4-methylpiperazin-1-yl)piperidin-1-yl)phenyl)pyrimidin-2-amine;

4-(1H-Indol-3-yl)-2-(2-methoxy-4-(4-(4-methylpiperazin-1-yl)piperidin-1-yl)phenylamino)pyrimidine-5-carbonitrile;

N-(4-(4-(dimethylamino)piperidin-1-yl)-2-methoxyphenyl)-4-(1H-indol-3-yl)-5-(trifluoromethyl)pyrimidin-2-amine as the trifluoroacetic acid salt;

N-(4-(4-amino-3,3-dimethylpiperidin-1-yl)-2-methoxyphenyl)-5-chloro-4-(1H-indol-3-yl)pyrimidin-2-amine;

5-chloro-N-(4-(3,3-dimethyl-4-(methylamino)piperidin-1-yl)-2-methoxyphenyl)-4-(1H-indol-3-yl)pyrimidin-2-amine;

5-chloro-N-(4-(4-(dimethylamino)-3,3-dimethylpiperidin-1-yl)-2-methoxyphenyl)-4-(1H-indol-3-yl)pyrimidin-2-amine;

N-(4-((3R,4S)-4-amino-3-fluoropiperidin-1-yl)-2-methoxyphenyl)-5-chloro-4-(1H-indol-3-yl)pyrimidin-2-amine;

5-Chloro-N-(2-methoxy-4-(4-(4-methylpiperazin-1-yl)piperidin-1-yl)phenyl)-4-(1-methyl-1H-indol-3-yl)pyrimidin-2-amine HCl salt;

N-(4-(4-aminopiperidin-1-yl)-2-methoxyphenyl)-5-chloro-4-(1-methyl-1H-indol-3-yl)pyrimidin-2-amine TFA salt;

5-fluoro-N-(2-methoxy-4-(4-(4-methylpiperazin-1-yl)piperidin-1-yl)phenyl)-4-(1-methyl-1H-indol-3-yl)pyrimidin-2-amine;

5-Fluoro-N-[5-fluoro-2-methoxy-4-[4-(4-methylpiperazin-1-yl)-1-piperidyl]phenyl]-4-(1H-indol-3-yl)pyrimidin-2-amine;

N-[5-fluoro-2-methoxy-4-[4-(4-methylpiperazin-1-yl)-1-piperidyl]phenyl]-4-(1H-indol-3-yl)-5-methyl-pyrimidin-2-amine;

5-chloro-N-[5-fluoro-2-methoxy-4-[4-(4-methylpiperazin-1-yl)-1-piperidyl]phenyl]-4-(1H-indol-3-yl)pyrimidin-2-amine;

5-chloro-N-[5-chloro-2-methoxy-4-[4-(4-methylpiperazin-1-yl)-1-piperidyl]phenyl]-4-(1H-indol-3-yl)pyrimidin-2-amine;

N-[4-(4-Amino-1-piperidyl)-2-methoxy-phenyl]-5-fluoro-4-(1H-indol-3-yl)pyrimidin-2-amine; and N-[4-(4-amino-1-oxidophosphinan-1-yl)-2-methoxyphenyl]-5-chloro-4-(1H-indol-3-yl)pyrimidin-2-amine.

In certain embodiments, the present invention provides any compound listed herein, and, if a free base, a pharmaceutically acceptable salt thereof.

Also provided herein is:
N-(4-(4-Aminopiperidin-1-yl)-2-methoxyphenyl)-5-chloro-4-(1H-indol-3-yl)pyrimidin-2-amine as the trifluoroacetic acid salt;
5-Chloro-4-(1H-indol-3-yl)-N-(2-methoxy-4-(4-(methylamino)piperidin-1-yl)phenyl)pyrimidin-2-amine as the trifluoroacetic acid salt;
5-Chloro-4-(1H-indol-3-yl)-N-(2-methoxy-4-(4-(piperazin-1-yl)piperidin-1-yl)phenyl)pyrimidin-2-amine;
4-(1H-Indol-3-yl)-N-(2-methoxy-4-(4-(methylamino)piperidin-1-yl)phenyl)-5-methylpyrimidin-2-amine;
N-(4-(4-Aminopiperidin-1-yl)-2-methoxyphenyl)-4-(1H-indol-3-yl)-5-methylpyrimidin-2-amine as the trifluoroacetic acid salt;
5-Chloro-N-(4-(4-(cyclopropylamino)piperidin-1-yl)-2-methoxyphenyl)-4-(1H-indol-3-yl)pyrimidin-2-amine as the trifluoroacetic acid salt;
5-Fluoro-4-(1H-indol-3-yl)-N-(2-methoxy-4-(4-(4-methylpiperazin-1-yl)piperidin-1-yl)phenyl)pyrimidin-2-amine as the trifluoroacetic acid salt;
4-(1H-indol-3-yl)-N-(2-methoxy-4-(4-(4-methylpiperazin-1-yl)piperidin-1-yl)phenyl)-5-(trifluoromethyl)pyrimidin-2-amine;
4-(1H-indol-3-yl)-N-(2-methoxy-4-(4-(4-methylpiperazin-1-yl)piperidin-1-yl)phenyl)-5-methylpyrimidin-2-amine;
5-Chloro-4-(1H-indol-3-yl)-N-(2-methoxy-4-(4-(4-methylpiperazin-1-yl)piperidin-1-yl)phenyl)pyrimidin-2-amine;
N-(4-(4-(Dimethylamino)piperidin-1-yl)-2-methoxyphenyl)-4-(1H-indol-3-yl)-5-methylpyrimidin-2-amine;
5-Chloro-N-(4-(4-(dimethylamino)piperidin-1-yl)-2-methoxyphenyl)-4-(1H-indol-3-yl)pyrimidin-2-amine;
N-(4-(4-(Dimethylamino)piperidin-1-yl)-2-methoxyphenyl)-5-fluoro-4-(1H-indol-3-yl)pyrimidin-2-amine;
5-Chloro-4-(1H-indol-3-yl)-N-(2-methoxy-5-methyl-4-(4-(4-methylpiperazin-1-yl)piperidin-1-yl)phenyl)pyrimidin-2-amine;
4-(1H-indol-3-yl)-N-(2-methoxy-5-methyl-4-(4-(4-methylpiperazin-1-yl)piperidin-1-yl)phenyl)-5-methylpyrimidin-2-amine;
5-Chloro-N-(4-(4-(dimethylamino)piperidin-1-yl)-2-methoxy-5-methylphenyl)-4-(1H-indol-3-yl)pyrimidin-2-amine;
N-(4-(4-(Dimethylamino)piperidin-1-yl)-2-methoxy-5-methylphenyl)-4-(1H-indol-3-yl)-5-methylpyrimidin-2-amine;
N-(4-(4-Aminopiperidin-1-yl)-2-methoxy-5-methylphenyl)-5-chloro-4-(1H-indol-3-yl)pyrimidin-2-amine;
N-(4-(4-aminopiperidin-1-yl)-2-methoxy-5-methylphenyl)-4-(1H-indol-3-yl)-5-methylpyrimidin-2-amine;
2-(1-(4-(5-Chloro-4-(1H-indol-3-yl)pyrimidin-2-ylamino)-3-methoxyphenyl)piperidin-4-ylamino)ethanol;
5-Chloro-4-(1H-indol-3-yl)-N-(2-methoxy-4-{4-[4-(methylsulfonyl)piperazin-1-yl]piperidin-1-yl}phenyl)pyrimidin-2-amine as the trifluoroacetic acid salt;
5-Chloro-N-(4-{4-[(3R)-3-fluoropyrrolidin-1-yl]piperidin-1-yl}-2-methoxyphenyl)-4-(1H-indol-3-yl)pyrimidin-2-amine as the trifluoroacetic acid salt;
5-Chloro-4-(1H-indol-3-yl)-N-(4-(4-(4-isopropylpiperazin-1-yl)piperidin-1-yl)-2-methoxyphenyl)pyrimidin-2-amine as the trifluoroacetic acid salt;
5-Chloro-N-(4-(4-((2S,6R)-2,6-dimethylmorpholino)piperidin-1-yl)-2-methoxyphenyl)-4-(1H-indol-3-yl)pyrimidin-2-amine as the trifluoroacetic acid salt;
(R)-5-Chloro-N-(4-(4-(3-fluoropyrrolidin-1-yl)piperidin-1-yl)-2-methoxy-5-methylphenyl)-4-(1H-indol-3-yl)pyrimidin-2-amine;
5-Chloro-4-(1H-indol-3-yl)-N-(2-methoxy-4-(4-(oxetan-3-ylamino)piperidin-1-yl)phenyl)pyrimidin-2-amine as the trifluoroacetic acid salt;
(5-Bromo-4-(1H-indol-3-yl)-N-(2-methoxy-4-(4-(4-methylpiperazin-1-yl)piperidin-1-yl)phenyl)pyrimidin-2-amine;
4-(1H-indol-3-yl)-2-(2-methoxy-4-(4-(4-methylpiperazin-1-yl)piperidin-1-yl)phenylamino)pyrimidine-5-carbonitrile; and
N-(4-(4-(dimethylamino)piperidin-1-yl)-2-methoxyphenyl)-4-(1H-indol-3-yl)-5-(trifluoromethyl)pyrimidin-2-amine as the trifluoroacetic acid salt.
Also provided herein is:
N-(4-(4-Aminopiperidin-1-yl)-2-methoxyphenyl)-5-chloro-4-(1H-indol-3-yl)pyrimidin-2-amine as the trifluoroacetic acid salt;
5-Chloro-4-(1H-indol-3-yl)-N-(2-methoxy-4-(4-(methylamino)piperidin-1-yl)phenyl)pyrimidin-2-amine as the trifluoroacetic acid salt;
5-Chloro-4-(1H-indol-3-yl)-N-(2-methoxy-4-(4-(piperazin-1-yl)piperidin-1-yl)phenyl)pyrimidin-2-amine;
4-(1H-Indol-3-yl)-N-(2-methoxy-4-(4-(methylamino)piperidin-1-yl)phenyl)-5-methylpyrimidin-2-amine;
N-(4-(4-Aminopiperidin-1-yl)-2-methoxyphenyl)-4-(1H-indol-3-yl)-5-methylpyrimidin-2-amine as the trifluoroacetic acid salt;
5-Chloro-N-(4-(4-(cyclopropylamino)piperidin-1-yl)-2-methoxyphenyl)-4-(1H-indol-3-yl)pyrimidin-2-amine as the trifluoroacetic acid salt;
5-Fluoro-4-(1H-Indol-3-yl)-N-(2-methoxy-4-(4-(4-methylpiperazin-1-yl)piperidin-1-yl)phenyl)pyrimidin-2-amine as the trifluoroacetic acid salt;
4-(1H-Indol-3-yl)-N-(2-methoxy-4-(4-(4-methylpiperazin-1-yl)piperidin-1-yl)phenyl)-5-(trifluoromethyl)pyrimidin-2-amine;
4-(1H-Indol-3-yl)-N-(2-methoxy-4-(4-(4-methylpiperazin-1-yl)piperidin-1-yl)phenyl)-5-methylpyrimidin-2-amine;
5-Chloro-4-(1H-indol-3-yl)-N-(2-methoxy-4-(4-(4-methylpiperazin-1-yl)piperidin-1-yl)phenyl)pyrimidin-2-amine;
N-(4-(4-(Dimethylamino)piperidin-1-yl)-2-methoxyphenyl)-4-(1H-indol-3-yl)-5-methylpyrimidin-2-amine;
5-Chloro-N-(4-(4-(dimethylamino)piperidin-1-yl)-2-methoxyphenyl)-4-(1H-indol-3-yl)pyrimidin-2-amine;
N-(4-(4-(Dimethylamino)piperidin-1-yl)-2-methoxyphenyl)-5-fluoro-4-(1H-indol-3-yl)pyrimidin-2-amine;
5-Chloro-4-(1H-indol-3-yl)-N-(2-methoxy-5-methyl-4-(4-(4-methylpiperazin-1-yl)piperidin-1-yl)phenyl)pyrimidin-2-amine;
4-(1H-Indol-3-yl)-N-(2-methoxy-5-methyl-4-(4-(4-methylpiperazin-1-yl)piperidin-1-yl)phenyl)-5-methylpyrimidin-2-amine;
5-Chloro-N-(4-(4-(dimethylamino)piperidin-1-yl)-2-methoxy-5-methylphenyl)-4-(1H-indol-3-yl)pyrimidin-2-amine;
N-(4-(4-(Dimethylamino)piperidin-1-yl)-2-methoxy-5-methylphenyl)-4-(1H-indol-3-yl)-5-methylpyrimidin-2-amine;
N-(4-(4-Aminopiperidin-1-yl)-2-methoxy-5-methylphenyl)-5-chloro-4-(1H-indol-3-yl)pyrimidin-2-amine;
N-(4-(4-aminopiperidin-1-yl)-2-methoxy-5-methylphenyl)-4-(1H-indol-3-yl)-5-methylpyrimidin-2-amine;
2-(1-(4-(5-Chloro-4-(1H-indol-3-yl)pyrimidin-2-ylamino)-3-methoxyphenyl)piperidin-4-ylamino)ethanol;
5-Chloro-4-(1H-indol-3-yl)-N-(2-methoxy-4-{4-[4-(methylsulfonyl)piperazin-1-yl]piperidin-1-yl}phenyl)pyrimidin-2-amine as the trifluoroacetic acid salt;

5-Chloro-N-(4-{4-[(3R)-3-fluoropyrrolidin-1-yl]piperidin-1-yl}-2-methoxyphenyl)-4-(1H-indol-3-yl)pyrimidin-2-amine as the trifluoroacetic acid salt;

5-Chloro-4-(1H-indol-3-yl)-N-(4-(4-(4-isopropylpiperazin-1-yl)piperidin-1-yl)-2-methoxyphenyl)pyrimidin-2-amine as the trifluoroacetic acid salt;

5-Chloro-N-(4-(4-((2S,6R)-2,6-dimethylmorpholino)piperidin-1-yl)-2-methoxyphenyl)-4-(1H-indol-3-yl)pyrimidin-2-amine as the trifluoroacetic acid salt;

(R)-5-Chloro-N-(4-(4-(3-fluoropyrrolidin-1-yl)piperidin-1-yl)-2-methoxy-5-methylphenyl)-4-(1H-indol-3-yl)pyrimidin-2-amine;

5-Chloro-4-(1H-indol-3-yl)-N-(2-methoxy-4-(4-(oxetan-3-ylamino)piperidin-1-yl)phenyl)pyrimidin-2-amine as the trifluoroacetic acid salt;

(5-Bromo-4-(1H-indol-3-yl)-N-(2-methoxy-4-(4-(4-methylpiperazin-1-yl)piperidin-1-yl)phenyl)pyrimidin-2-amine;

4-(1H-Indol-3-yl)-2-(2-methoxy-4-(4-(4-methylpiperazin-1-yl)piperidin-1-yl)phenylamino)pyrimidine-5-carbonitrile;

N-(4-(4-(dimethylamino)piperidin-1-yl)-2-methoxyphenyl)-4-(1H-indol-3-yl)-5-(trifluoromethyl)pyrimidin-2-amine as the trifluoroacetic acid salt;

N-(4-(4-amino-3,3-dimethylpiperidin-1-yl)-2-methoxyphenyl)-5-chloro-4-(1H-indol-3-yl)pyrimidin-2-amine;

5-chloro-N-(4-(3,3-dimethyl-4-(methylamino)piperidin-1-yl)-2-methoxyphenyl)-4-(1H-indol-3-yl)pyrimidin-2-amine;

5-chloro-N-(4-(4-(dimethylamino)-3,3-dimethylpiperidin-1-yl)-2-methoxyphenyl)-4-(1H-indol-3-yl)pyrimidin-2-amine;

N-(4-((3R,4S)-4-amino-3-fluoropiperidin-1-yl)-2-methoxyphenyl)-5-chloro-4-(1H-indol-3-yl)pyrimidin-2-amine;

5-Chloro-N-(2-methoxy-4-(4-(4-methylpiperazin-1-yl)piperidin-1-yl)phenyl)-4-(1-methyl-1H-indol-3-yl)pyrimidin-2-amine HCl salt;

N-(4-(4-aminopiperidin-1-yl)-2-methoxyphenyl)-5-chloro-4-(1-methyl-1H-indol-3-yl)pyrimidin-2-amine TFA salt;

5-fluoro-N-(2-methoxy-4-(4-(4-methylpiperazin-1-yl)piperidin-1-yl)phenyl)-4-(1-methyl-1H-indol-3-yl)pyrimidin-2-amine;

5-Fluoro-N-[5-fluoro-2-methoxy-4-[4-(4-methylpiperazin-1-yl)-1-piperidyl]phenyl]-4-(1H-indol-3-yl)pyrimidin-2-amine;

N-[5-fluoro-2-methoxy-4-[4-(4-methylpiperazin-1-yl)-1-piperidyl]phenyl]-4-(1H-indol-3-yl)-5-methyl-pyrimidin-2-amine;

5-chloro-N-[5-fluoro-2-methoxy-4-[4-(4-methylpiperazin-1-yl)-1-piperidyl]phenyl]-4-(1H-indol-3-yl)pyrimidin-2-amine;

5-chloro-N-[5-chloro-2-methoxy-4-[4-(4-methylpiperazin-1-yl)-1-piperidyl]phenyl]-4-(1H-indol-3-yl)pyrimidin-2-amine;

N-[4-(4-Amino-1-piperidyl)-2-methoxy-phenyl]-5-fluoro-4-(1H-indol-3-yl)pyrimidin-2-amine; and N-[4-(4-amino-1-oxidophosphinan-1-yl)-2-methoxyphenyl]-5-chloro-4-(1H-indol-3-yl)pyrimidin-2-amine.

In one aspect, provided is a compound selected from:

N-(4-(4-Aminopiperidin-1-yl)-2-methoxyphenyl)-5-chloro-4-(1H-indol-3-yl)pyrimidin-2-amine;

5-Chloro-4-(1H-indol-3-yl)-N-(2-methoxy-4-(4-(methylamino)piperidin-1-yl)phenyl)pyrimidin-2-amine;

5-Chloro-4-(1H-indol-3-yl)-N-(2-methoxy-4-(4-(piperazin-1-yl)piperidin-1-yl)phenyl)pyrimidin-2-amine;

4-(1H-Indol-3-yl)-N-(2-methoxy-4-(4-(methylamino)piperidin-1-yl)phenyl)-5-methylpyrimidin-2-amine;

N-(4-(4-Aminopiperidin-1-yl)-2-methoxyphenyl)-4-(1H-indol-3-yl)-5-methylpyrimidin-2-amine;

5-Chloro-N-(4-(4-(cyclopropylamino)piperidin-1-yl)-2-methoxyphenyl)-4-(1H-indol-3-yl)pyrimidin-2-amine;

5-Fluoro-4-(1H-Indol-3-yl)-N-(2-methoxy-4-(4-(4-methylpiperazin-1-yl)piperidin-1-yl)phenyl)pyrimidin-2-amine;

4-(1H-Indol-3-yl)-N-(2-methoxy-4-(4-(4-methylpiperazin-1-yl)piperidin-1-yl)phenyl)-5-(trifluoromethyl)pyrimidin-2-amine;

4-(1H-Indol-3-yl)-N-(2-methoxy-4-(4-(4-methylpiperazin-1-yl)piperidin-1-yl)phenyl)-5-methylpyrimidin-2-amine;

5-Chloro-4-(1H-indol-3-yl)-N-(2-methoxy-4-(4-(4-methylpiperazin-1-yl)piperidin-1-yl)phenyl)pyrimidin-2-amine;

N-(4-(4-(Dimethylamino)piperidin-1-yl)-2-methoxyphenyl)-4-(1H-indol-3-yl)-5-methylpyrimidin-2-amine;

5-Chloro-N-(4-(4-(dimethylamino)piperidin-1-yl)-2-methoxyphenyl)-4-(1H-indol-3-yl)pyrimidin-2-amine;

N-(4-(4-(Dimethylamino)piperidin-1-yl)-2-methoxyphenyl)-5-fluoro-4-(1H-indol-3-yl)pyrimidin-2-amine;

5-Chloro-4-(1H-indol-3-yl)-N-(2-methoxy-5-methyl-4-(4-(4-methylpiperazin-1-yl)piperidin-1-yl)phenyl)pyrimidin-2-amine;

4-(1H-Indol-3-yl)-N-(2-methoxy-5-methyl-4-(4-(4-methylpiperazin-1-yl)piperidin-1-yl)phenyl)-5-methylpyrimidin-2-amine;

5-Chloro-N-(4-(4-(dimethylamino)piperidin-1-yl)-2-methoxy-5-methylphenyl)-4-(1H-indol-3-yl)pyrimidin-2-amine;

N-(4-(4-(Dimethylamino)piperidin-1-yl)-2-methoxy-5-methylphenyl)-4-(1H-indol-3-yl)-5-methylpyrimidin-2-amine;

N-(4-(4-Aminopiperidin-1-yl)-2-methoxy-5-methylphenyl)-5-chloro-4-(1H-indol-3-yl)pyrimidin-2-amine;

N-(4-(4-aminopiperidin-1-yl)-2-methoxy-5-methylphenyl)-4-(1H-indol-3-yl)-5-methylpyrimidin-2-amine;

2-(1-(4-(5-Chloro-4-(1H-indol-3-yl)pyrimidin-2-ylamino)-3-methoxyphenyl)piperidin-4-ylamino)ethanol;

5-Chloro-4-(1H-indol-3-yl)-N-(2-methoxy-4-{4-[4-(methylsulfonyl)piperazin-1-yl]piperidin-1-yl}phenyl)pyrimidin-2-amine;

5-Chloro-N-(4-{4-[(3R)-3-fluoropyrrolidin-1-yl]piperidin-1-yl}-2-methoxyphenyl)-4-(1H-indol-3-yl)pyrimidin-2-amine;

5-Chloro-4-(1H-indol-3-yl)-N-(4-(4-(4-isopropylpiperazin-1-yl)piperidin-1-yl)-2-methoxyphenyl)pyrimidin-2-amine;

5-Chloro-N-(4-(4-((2S,6R)-2,6-dimethylmorpholino)piperidin-1-yl)-2-methoxyphenyl)-4-(1H-indol-3-yl)pyrimidin-2-amine;

(R)-5-Chloro-N-(4-(4-(3-fluoropyrrolidin-1-yl)piperidin-1-yl)-2-methoxy-5-methylphenyl)-4-(1H-indol-3-yl)pyrimidin-2-amine;

5-Chloro-4-(1H-indol-3-yl)-N-(2-methoxy-4-(4-(oxetan-3-ylamino)piperidin-1-yl)phenyl)pyrimidin-2-amine;

(5-Bromo-4-(1H-indol-3-yl)-N-(2-methoxy-4-(4-(4-methylpiperazin-1-yl)piperidin-1-yl)phenyl)pyrimidin-2-amine;

4-(1H-Indol-3-yl)-2-(2-methoxy-4-(4-(4-methylpiperazin-1-yl)piperidin-1-yl)phenylamino)pyrimidine-5-carbonitrile;

N-(4-(4-(dimethylamino)piperidin-1-yl)-2-methoxyphenyl)-4-(1H-indol-3-yl)-5-(trifluoromethyl)pyrimidin-2-amine;

N-(4-(4-amino-3,3-dimethylpiperidin-1-yl)-2-methoxyphenyl)-5-chloro-4-(1H-indol-3-yl)pyrimidin-2-amine;

5-chloro-N-(4-(3,3-dimethyl-4-(methylamino)piperidin-1-yl)-2-methoxyphenyl)-4-(1H-indol-3-yl)pyrimidin-2-amine;

5-chloro-N-(4-(4-(dimethylamino)-3,3-dimethylpiperidin-1-yl)-2-methoxyphenyl)-4-(1H-indol-3-yl)pyrimidin-2-amine;

N-(4-((3R,4S)-4-amino-3-fluoropiperidin-1-yl)-2-methoxyphenyl)-5-chloro-4-(1H-indol-3-yl)pyrimidin-2-amine;

N-(4-((3S,4R)-4-amino-3-fluoropiperidin-1-yl)-2-methoxyphenyl)-5-chloro-4-(1H-indol-3-yl)pyrimidin-2-amine;

5-Chloro-N-(2-methoxy-4-(4-(4-methylpiperazin-1-yl)piperidin-1-yl)phenyl)-4-(1-methyl-1H-indol-3-yl)pyrimidin-2-amine;

N-(4-(4-aminopiperidin-1-yl)-2-methoxyphenyl)-5-chloro-4-(1-methyl-1H-indol-3-yl)pyrimidin-2-amine;

5-fluoro-N-(2-methoxy-4-(4-(4-methylpiperazin-1-yl)piperidin-1-yl)phenyl)-4-(1-methyl-1H-indol-3-yl)pyrimidin-2-amine;

5-Fluoro-N-[5-fluoro-2-methoxy-4-[4-(4-methylpiperazin-1-yl)-1-piperidyl]phenyl]-4-(1H-indol-3-yl)pyrimidin-2-amine;

N-[5-fluoro-2-methoxy-4-[4-(4-methylpiperazin-1-yl)-1-piperidyl]phenyl]-4-(1H-indol-3-yl)-5-methyl-pyrimidin-2-amine;

5-chloro-N-[5-fluoro-2-methoxy-4-[4-(4-methylpiperazin-1-yl)-1-piperidyl]phenyl]-4-(1H-indol-3-yl)pyrimidin-2-amine;

5-chloro-N-[5-chloro-2-methoxy-4-[4-(4-methylpiperazin-1-yl)-1-piperidyl]phenyl]-4-(1H-indol-3-yl)pyrimidin-2-amine;

N-[4-(4-Amino-1-piperidyl)-2-methoxy-phenyl]-5-fluoro-4-(1H-indol-3-yl)pyrimidin-2-amine;

(cis)-N-[4-(4-amino-1-oxidophosphinan-1-yl)-2-methoxyphenyl]-5-chloro-4-(1H-indol-3-yl)pyrimidin-2-amine;

(trans)-N-[4-(4-amino-1-oxidophosphinan-1-yl)-2-methoxyphenyl]-5-chloro-4-(1H-indol-3-yl)pyrimidin-2-amine;

(cis)-N-[4-(4-amino-1-oxidophosphinan-1-yl)-2-methoxyphenyl]-4-(1H-indol-3-yl)-5-methylpyrimidin-2-amine;

(trans)-N-[4-(4-amino-1-oxidophosphinan-1-yl)-2-methoxyphenyl]-4-(1H-indol-3-yl)-5-methylpyrimidin-2-amine;

N-[4-[(3R,4R)-4-amino-3-fluoro-1-piperidyl]-2-methoxy-phenyl]-5-chloro-4-(1H-indol-3-yl)pyrimidin-2-amine;

N-[4-[(3S,4S)-4-amino-3-fluoro-1-piperidyl]-2-methoxyphenyl]-5-chloro-4-(1H-indol-3-yl)pyrimidin-2-amine;

N-(4-((3S,4R)-4-amino-3-fluoropiperidin-1-yl)-2-methoxyphenyl)-5-chloro-4-(1H-indol-3-yl)pyrimidin-2-amine; and N-(4-((3R,4S)-4-amino-3-fluoropiperidin-1-yl)-2-methoxyphenyl)-5-chloro-4-(1H-indol-3-yl)pyrimidin-2-amine; and/or a pharmaceutically acceptable salt thereof.

In one aspect, provided is a compound selected from:

N-(4-(4-aminopiperidin-1-yl)-2-methoxyphenyl)-5-chloro-4-(1H-indol-3-yl)pyrimidin-2-amine;

4-(1H-indol-3-yl)-N-(2-methoxy-4-(4-(4-methylpiperazin-1-yl)piperidin-1-yl)phenyl)-5-methylpyrimidin-2-amine; and 5-Chloro-4-(1H-indol-3-yl)-N-(2-methoxy-4-(4-(4-methylpiperazin-1-yl)piperidin-1-yl)phenyl)pyrimidin-2-amine; and/or a pharmaceutically acceptable salt thereof.

In this specification the prefix $C_{x-y}$ as used in terms such as $C_{x-y}$alkyl and the like (where x and y are integers) indicates the numerical range of carbon atoms that are present in the group; for example, $C_{1-4}$alkyl includes $C_1$alkyl(methyl), $C_1$alkyl(ethyl), $C_1$alkyl(propyl and isopropyl) and $C_1$alkyl (butyl, 1-methylpropyl, 2-methylpropyl, and t-butyl).

Compounds of Formula (I) and/or Formula (Ia) may have one or more chiral centers, and it is to be understood that the invention encompasses all such stereoisomers, including enantiomers and diastereoisomers. Thus, it is to be understood that, insofar as certain compounds of Formula (I) and/or Formula (Ia) may exist in optically active or racemic forms by virtue of one or more asymmetric carbon atoms, the invention includes in its definition any such optically active or racemic form which possesses the above-mentioned activity. The present invention encompasses all such stereoisomers having activity as herein defined.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Thus, throughout the specification, where reference is made to the compound of Formula (I) and/or Formula (Ia), it is to be understood that the term compound includes isomers, mixtures of isomers, solvates, stereoisomers, and polymorphs that inhibit ALK tyrosine kinase activity in a human or animal.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free for other stereoisomers, for example containing less than 20%, particularly less than 10% and more particularly less than 5% by weight of other stereoisomers.

It is to be understood that, insofar as certain compounds of Formula (I) and/or Formula (Ia) defined above may exist in tautomeric forms, the invention includes in its definition any such tautomeric form which possesses the above-mentioned activity. Thus, the invention relates to all tautomeric forms of compounds of Formula (I) and/or Formula (Ia) which inhibit ALK tyrosine kinase activity in a human or animal.

It is also to be understood that certain compounds of Formula (I) and/or Formula (Ia) can exist in solvated as well as unsolvated forms such as, for example, hydrated forms. It is to be understood that the invention encompasses all such solvated forms.

III. General Methods of Preparation

The present invention provides synthetic methodologies for preparing compounds of Formula (I) and/or Formula (Ia) comprising coupling a 2-chloropyrimidine compound of formula (a) with an aniline compound of formula (b) in the presence of suitable catalytic acid or base or by employing a Buchwald coupling. In certain embodiments, compounds of Formula (I) and/or Formula (Ia) is further purified.

In certain embodiments, compounds of Formula (I) and/or Formula (Ia) are generally prepared according to the steps depicted in SCHEME 1 set forth below.

SCHEME 1

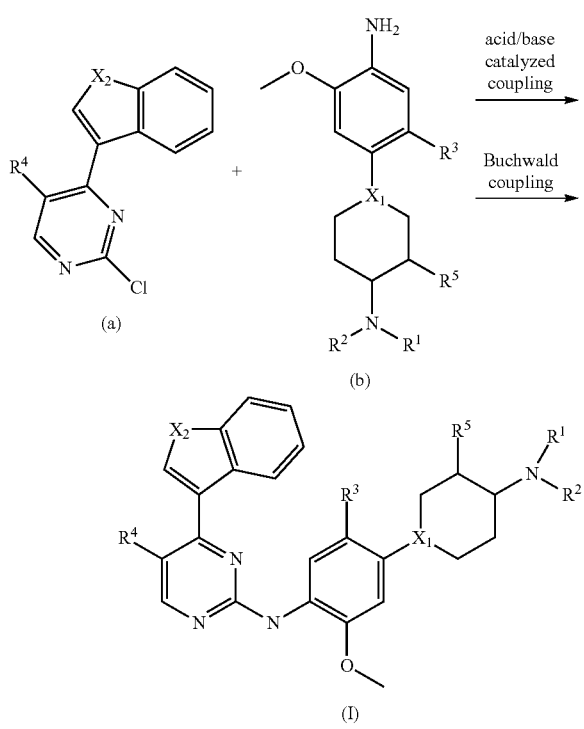

In SCHEME 1 above, $R^1$, $R^2$, $R^3$, $R^4$, $R^5$, $X_1$ and $X_2$ are defined in classes and subclasses as described herein.

In certain embodiments, the present invention provides a method for preparing compounds of Formula (I) comprising providing a 2-chloropyrimidine compound of formula (a), an aniline compound of formula (b) and coupling the compound of formula (a) with the compound of formula (b).

As depicted in SCHEME 1, a 2-chloropyrimidine compound of formula (a) is coupled to an aniline compound of formula (b) via a direct acid or base catalyzed coupling reaction in the presence of a suitable solvent at a temperature of from about 100° C. to about 170° C. In some embodiments, the temperature of the coupling reaction is 100° C. In some embodiments, the temperature of the coupling reaction is 110° C. In some embodiments, the temperature of the coupling reaction is 120° C. In some embodiments, the temperature of the coupling reaction is 130° C. In some embodiments, the temperature of the coupling reaction is 140° C. In some embodiments, the temperature of the coupling reaction is 150° C. In some embodiments, the temperature of the coupling reaction is 160° C. In some embodiments, the temperature of the coupling reaction is 170° C. In some embodiments, a suitable acid catalyst is aqueous hydrochloric acid. In some embodiments, a suitable acid catalyst is p-toluenesulfonic acid (PTSA). In some embodiments, a suitable base catalyst is diisopropylethylamine (DIPEA). In some embodiments, a suitable solvent includes an alcoholic solvent. Exemplary alcoholic solvents include, but are not limited to isopropyl alcohol, n-butanol, pentanol, trifluoroethanol, and/or a mixture of an alcohol and N-methylpyrrolidone (NMP).

According to an alternate embodiment, a 2-chloropyrimidine compound of formula (a) is coupled to an aniline compound of formula (b) under coupling conditions known to one of ordinary skill in the art (e.g., Buchwald coupling reaction conditions) in the presence of an appropriate palladium catalyst, ligand, base, and a suitable solvent at a temperature of from about 60° C. to about 170° C. In some embodiments, a suitable temperature is from about 80° C. to about 150° C. In some embodiments, a suitable temperature is from about 90° C. to about 140° C. In some embodiments, a suitable temperature is about 90° C. In some embodiments, a suitable temperature is about 100° C. In some embodiments, a suitable temperature is about 110° C. In some embodiments, a suitable temperature is about 120° C. In some embodiments, a suitable temperature is about 130° C. In some embodiments, a suitable temperature is about 140° C. In some embodiments, a suitable palladium catalyst includes but is not limited to $Pd_2(dba)_3$. In some embodiments, a suitable ligand includes, but is not limited to BINAP. In some embodiments, a suitable base includes, but is not limited to sodium tert-butoxide. In some embodiments, a suitable solvent includes, but is not limited to toluene.

In certain embodiments, a compound of formula (a) when $X_2$ is —NH— and/or when $X_2$ is —N($C_{1-4}$ alkyl)- is generally prepared according to the steps depicted in SCHEME 2 set forth below.

SCHEME 2

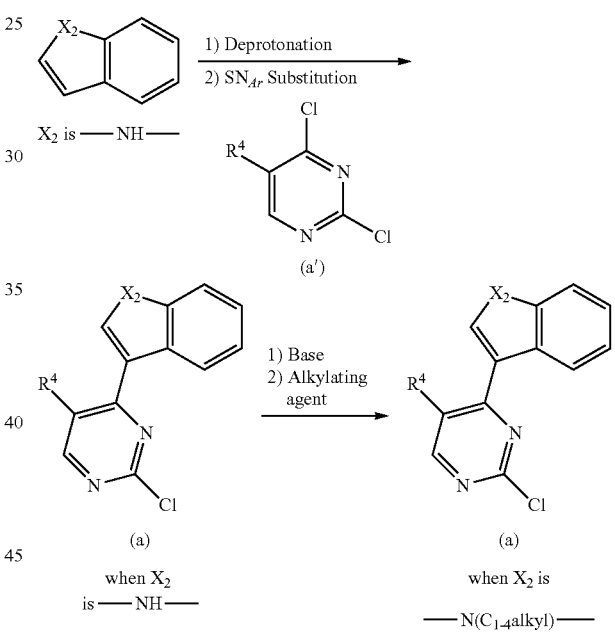

In SCHEME 2 above, $X_2$ and $R^4$ are defined in classes and subclasses as described herein.

As depicted in SCHEME 2, a one-pot reaction is performed to form a compound of formula (a) by deprotonating 1H-indole using a suitable grignard reagent, and thereafter performing a substitution reaction by adding a dichloropyrimidine compound of formula (a'), to form a compound of formula (a) wherein $X_2$ is —NH—, using a suitable solvent. In some embodiments a suitable solvent includes but is not limited to dichloromethane and/or dichloroethane. In some embodiments, a suitable solvent is dichloromethane. In some embodiments, a suitable solvent is dichloroethane. In some embodiments, a suitable solvent is a mixture of dichloromethane and dichloroethane.

The deprotonation step in SCHEME 2 is performed using a suitable grinard reagent in the presence of a suitable solvent. In some embodiments, a suitable grignard reagent includes, but is not limited to methylmagnesium iodide, ethylmagnesium bromide, and isopropylmagnesium bromide. In some embodiments, a suitable grignard is methylmagnesium iodide. In some embodiments, a suitable grignard is ethylmagnesium bromide. In some embodiments, a suitable grignard is isopropylmagnesium bromide. In some embodiments, a suitable temperature is from about −20° C. to about room temperature (i.e., ~25° C.). In some embodiments, a suitable temperature is from about −10° C. to about 20° C. In some embodiments, a suitable temperature is from about 0° C. to about 10° C. In some embodiments, a suitable temperature is about 0° C.

The substitution step in SCHEME 2 is done at a suitable temperature range. In some embodiments, a suitable temperature is from about 0° C. to about 25° C. In some embodiments, a suitable temperature is from about 0° C. to about 20° C. In some embodiments, a suitable temperature is from about 0° C. to about 10° C. In some embodiments, a suitable temperature is from about 0° C. to about 5° C. In some embodiments, a suitable temperature is about 0° C.

According to a further embodiment, a compound of formula (a) wherein $X_2$ is —NH—, is treated with a suitable base and an alkylating agent to form a compound of formula (a) wherein $X_2$ is —N($C_{1-4}$ alkyl)-. In some embodiments, a suitable base includes, but is not limited to NaH and/or KOt-Bu. In some embodiments, suitable alkylating agents include, but are not limited to methyl iodide, ethyl iodide, iso-propyl iodide, n-propyl iodide and/or n-butyl iodide.

In certain embodiments, a starting material compound of formula (a) when $X_2$ is —NH— is generally prepared according to the steps depicted in SCHEME 3 set forth below.

SCHEME 3

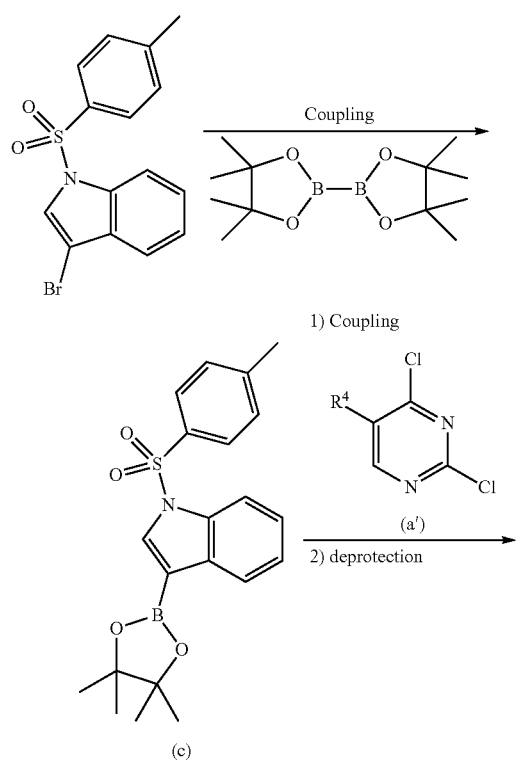

-continued

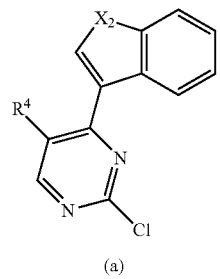

(a)

when $X_2$ is —NH—

In SCHEME 3 above, $R^4$ and $X_2$ are defined in classes and subclasses as described herein.

As depicted in SCHEME 3, the boronate of formula (c) is prepared by treating 3-bromo-1-tosyl-1H-indole with 4,4,4',4',5,5,5',5'-octamethyl-2,2'-bi(1,3,2-dioxaborolane) under coupling conditions known to one of ordinary skill in the art (e.g., Suzuki). The boronate of formula (c) is further coupled with a dichloropyrimidine compound of formula (a') under coupling conditions known to one of ordinary skill in the art (e.g., Suzuki), followed by subsequent deprotection at a temperature of about 50 to 150° C. using a suitable base in the presence of a solvent, to form a compound of formula (a) wherein $X_2$ is —NH—. In some embodiments, a suitable temperature is from about 70 to 130° C. In some embodiments, a suitable temperature is from about 70 to 110° C. In some embodiments, a suitable temperature is 70° C. In some embodiments, a suitable temperature is 80° C. In some embodiments, a suitable temperature is 90° C. In some embodiments, a suitable temperature is 100° C. In some embodiments, a suitable temperature is 110° C.

In some embodiments, a suitable palladium catalyst employed for a Suzuki coupling reaction includes, but is not limited to Pd(PPh$_3$)$_4$, PdCl$_2$(dppf).CH$_2$Cl$_2$, PdCl$_2$(PP$_3$)$_2$, Pd(OAc)$_2$, and/or Pd$_2$(dba)$_3$. In some embodiments, a suitable ligand employed for a Suzuki coupling reaction includes, but is not limited to PPh$_3$, P(t-Bu)$_3$, and/or PCy$_3$. In some embodiments, a suitable inorganic base employed for a Suzuki coupling reaction includes, but is not limited to cesium carbonate, sodium carbonate, potassium acetate, potassium carbonate, sodium hydroxide, and/or sodium ethoxide. In some embodiments, a suitable solvent employed for a Suzuki coupling reaction includes, but is not limited to dioxane, THF, DMSO, DMF, ethanol, toluene, and/or mixtures of water with dioxane, THF, DMSO, DMF, ethanol, and/or toluene.

In some embodiments, a suitable base used for the subsequent deprotection in SCHEME 3 includes, but is not limited to sodium hydroxide, sodium methoxide, cesium carbonate and/or sodium tert-butoxide. In some embodiments, a suitable solvent used for the subsequent deprotection in SCHEME 3 includes, but is not limited to methanol, isopropanol, t-butanol, n-butanol, n-pentanol, and/or a mixture of tetrahydrofuran with methanol, isopropanol, t-butanol, n-butanol, n-pentanol.

In certain embodiments, a starting material compound of formula (b) is generally prepared according to the steps depicted in SCHEME 4 set forth below.

SCHEME 4

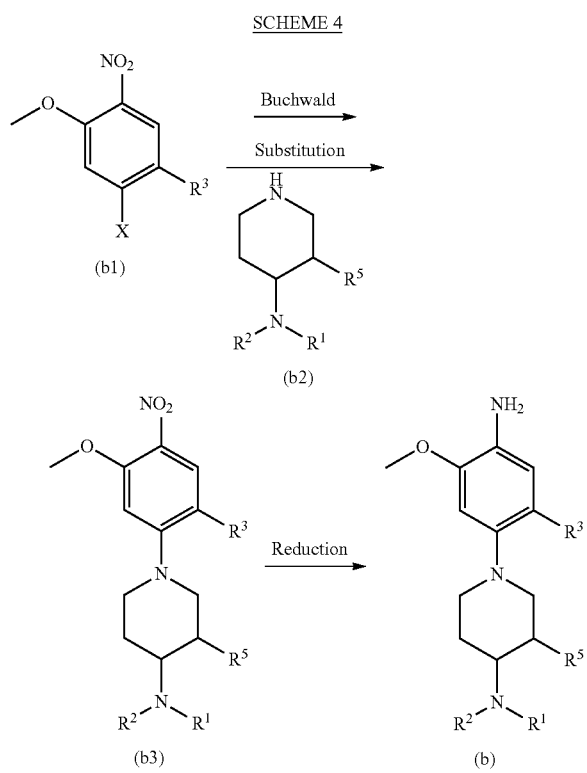

In SCHEME 4 above, $R^1$, $R^2$, $R^3$, and $R^5$ are defined in classes and subclasses as described herein. X is a halo or a suitable leaving group. Exemplary halo groups include fluorine, chlorine, bromine and iodine. Exemplary leaving groups include, but are not limited to tosylate, mesylate, nitro, and triflate.

As depicted in SCHEME 4, a nitrobenzene compound of formula (b3) is prepared by treating a nitrobenzene compound of formula (b1) with a piperidinyl compound of formula (b2) via a substitution reaction in the presence of a suitable base and a suitable solvent at a temperature of from about room temperature to reflux. In some embodiments, the temperature of the coupling reaction is from about room temperature to about reflux. In some embodiments, the temperature of the coupling reaction is about room temperature. In some embodiments, the temperature of the coupling reaction is about reflux. In some embodiments, the temperature of the coupling reaction is about 60° C. In some embodiments, a suitable base includes, but is not limited to potassium carbonate. In some embodiments, a suitable solvent includes but is not limited to acetonitrile, acetone, DMF and/or DMSO.

According to an alternate embodiment, a nitrobenzene compound of formula (b3) is prepared by treating a nitrobenzene compound of formula (b1) with a piperidinyl compound of formula (b2) under coupling conditions known to one of ordinary skill in the art (e.g., Buchwald coupling reaction conditions) in the presence of an appropriate palladium catalyst, ligand, base, and a suitable solvent at a temperature of from about 60° C. to about 170° C. In some embodiments, a suitable temperature is from about 80° C. to about 150° C. In some embodiments, a suitable temperature is from about 90° C. to about 140° C. In some embodiments, a suitable temperature is about 90° C. In some embodiments, a suitable temperature is about 100° C. In some embodiments, a suitable temperature is about 110° C. In some embodiments, a suitable temperature is about 120° C. In some embodiments, a suitable temperature is about 130° C. In some embodiments, a suitable temperature is about 140° C. In some embodiments, a suitable palladium catalyst includes but is not limited to $Pd_2(dba)_3$. In some embodiments, a suitable ligand includes, but is not limited to BINAP. In some embodiments, a suitable base includes, but is not limited to sodium tert-butoxide. In some embodiments, a suitable solvent includes, but is not limited to toluene.

As depicted in SCHEME 4, an aniline compound of formula (b) is prepared by further reducing a nitrobenzene compound of formula (b3) using nitro reduction conditions known to one of ordinary skill in the art. Such conditions and/or reagents to achieve nitro reduction include, but are not limited to catalyzed hydrogenation, using reduction reagents such as iron, zinc, and/or titanium trichloride, tin dichloride reduction, ferric ($Fe^{3+}$) catalyzed hydrazine reduction, sodium hydrosulfite reduction, and/or sodium sulfide reduction.

Alternatively, in certain embodiments a starting material compound of formula (b) is generally prepared according to the steps depicted in SCHEME 5 set forth below.

SCHEME 5

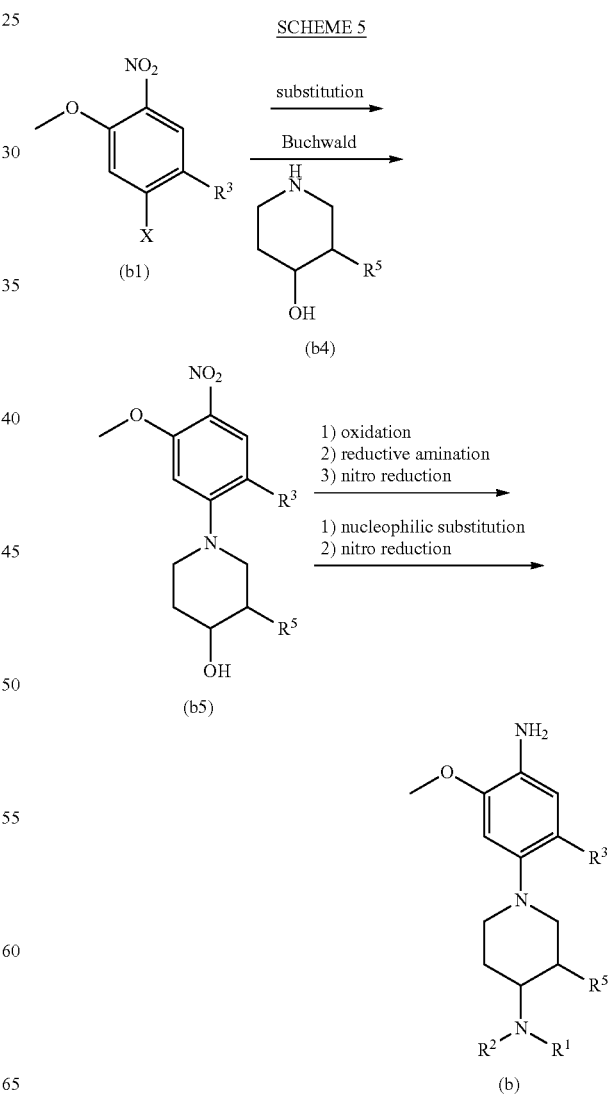

In SCHEME 5 above, $R^1$, $R^2$, $R^3$, and $R^5$ are defined in classes and subclasses as described herein. X is a halo group. Exemplary halo groups include fluorine, chlorine, bromine and/or iodine.

As depicted in SCHEME 5, a nitrobenzene compound of formula (b5) is prepared by treating a nitrobenzene compound of formula (b1) with a piperidinyl compound of formula (b4) using procedures and conditions similar to those described for SCHEME 4 herein.

As depicted in SCHEME 5, an aniline compound of formula (b) is prepared by further oxidizing a nitrobenzene compound of formula (b5) using oxidation conditions known to one of ordinary skill in the art, followed by reductive amination and a nitro reduction. Oxidation methods utilized include, but are not limited to methods used to oxidize alcohol groups to ketone, or aldehyde groups. Exemplary conditions and/or reagents to achieve oxidation include, but are not limited to Swern oxidation, Dess-Martin oxidation, Jone's Reagent and/or manganese dioxide. Conditions and/or reagents to achieve reductive amination include but are not limited to sodium borohydride, sodium cyanoborohydride, or sodium triacetoxyborohydride. Conditions and/or reagents to achieve nitro reduction include, but are not limited to catalyzed hydrogenation, using reduction reagents such as iron, zinc, and/or titanium trichloride, tin dichloride reduction, ferric ($F^{e3+}$) catalyzed hydrazine reduction, sodium hydrosulfite reduction, and/or sodium sulfide reduction.

According to an alternate embodiment, an aniline compound of formula (b) is prepared by converting the hydroxyl group of the nitrobenzene compound of formula (b5) to an alkylating agent, followed by a nucleophilic substitution with an amino group and nitro reduction. Exemplary alkylating agents that the hydroxyl group of the nitrobenzene compound of formula (b5) are converted to include, but are not limited to a sulfonate ester and/or a halide. Conditions and/or reagents to achieve nitro reduction include, but are not limited to catalyzed hydrogenation, using reduction reagents such as iron, zinc, and/or titanium trichloride, tin dichloride reduction, ferric ($F^{e3+}$) catalyzed hydrazine reduction, sodium hydrosulfite reduction, and/or sodium sulfide reduction.

In certain embodiments, a starting material compound of formula (b) is generally prepared according to the steps depicted in SCHEME 6 set forth below.

SCHEME 6

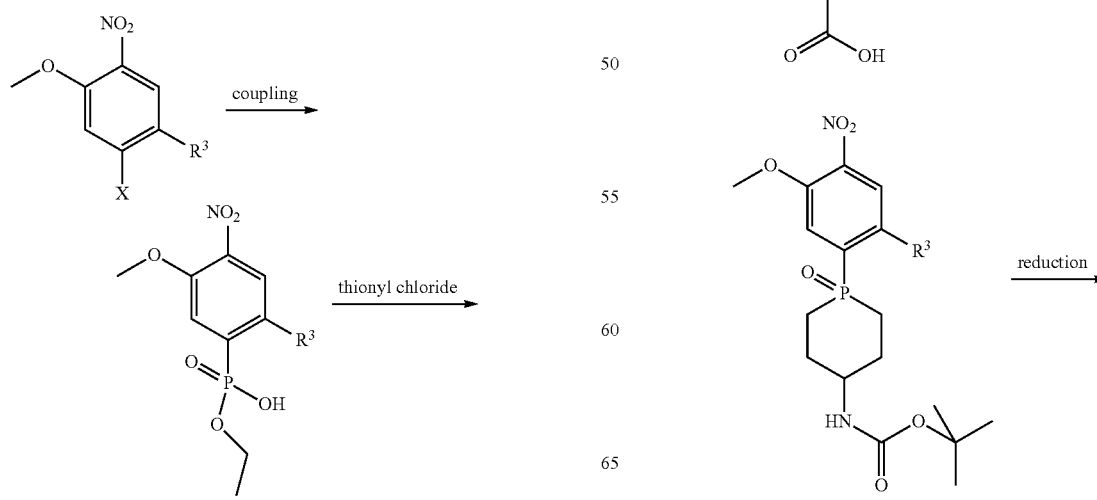

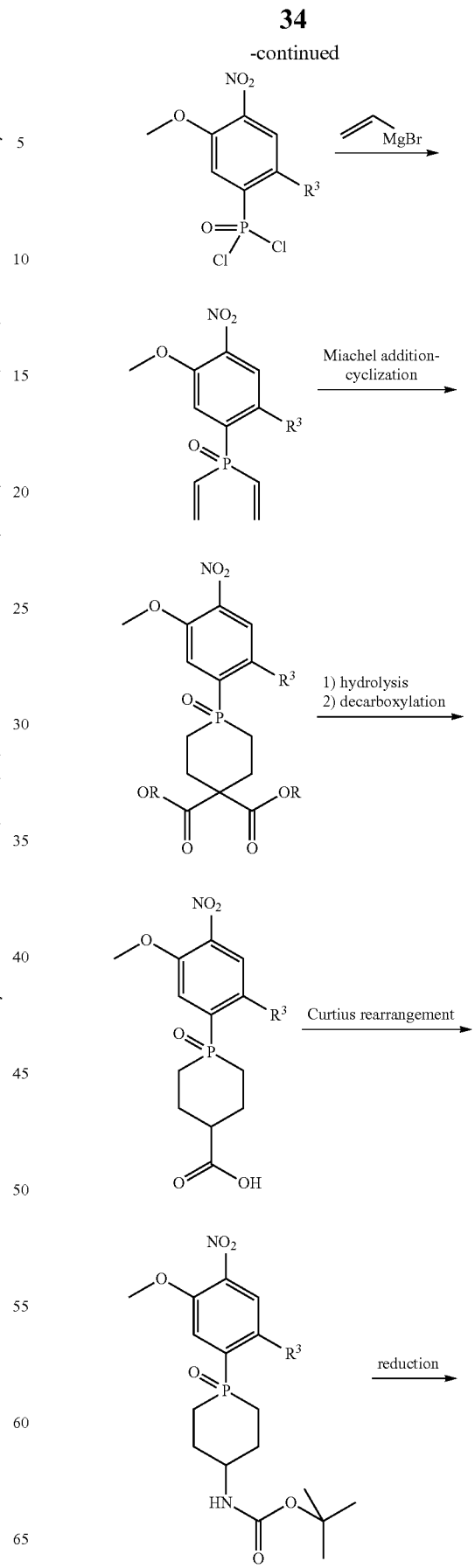

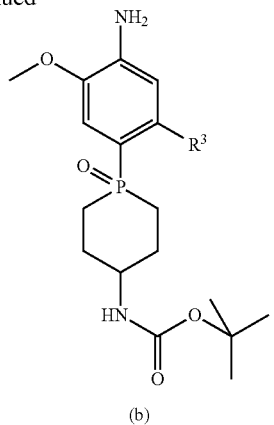

(b)

In SCHEME 6 above, R³ is defined in classes and subclasses as described herein.

As depicted in SCHEME 6, an aniline compound of formula (b) is prepared by via exemplary procedures as described herein. More specifically, please see EXAMPLE 42.

Utility

Compounds of Formula (I) and/or Formula (Ia) are useful for their ability to inhibit ALK kinase activity. Compounds of Formula (I) and/or Formula (Ia) are thus also useful in the treatment of diseases or medical conditions mediated alone or in part by the ALK tyrosine kinase. Examples of proliferative and hyperproliferative diseases/conditions which may be driven by ALK include cancers such as: carcinoma (such as carcinoma of the bladder, brain, breast, colon, kidney, liver, lung, ovary, pancreas, prostate, stomach, cervix, colon, thyroid, and skin); hematopoietic tumors of lymphoid lineage (such as acute lymphocytic leukaemia, B-cell lymphoma, and Burketts lymphoma); hematopoietic tumours of myeloid lineage (such as acute and chronic myelogenous leukaemias, and promyelocytic leukaemia); tumours of mesenchymal origin (such as fibrosarcoma and rhabdomyosarcoma); and other tumours, including melanoma, seminoma, tetratocarcinoma, neuroblastoma and glioma.

Compounds of Formula (I) and/or Formula (Ia) have been shown to inhibit tyrosine kinases, particularly the ALK family and, as demonstrated by the ALK assay described below.

In some embodiments, compounds of Formula (I) and/or Formula (Ia) have been shown to inhibit ALK kinase. In some embodiments, compounds of Formula (I) and/or Formula (Ia) have been shown to inhibit IGF1R kinase. In some embodiments, compounds of Formula (I) and/or Formula (Ia) have been shown to inhibit EGFR kinase. In some embodiments, compounds of Formula (I) and/or Formula (Ia) have been shown to inhibit FGFR kinase. In some embodiments, compounds of Formula (I) and/or Formula (Ia) have been shown to inhibit INSR kinase.

In some embodiments, compounds of Formula (I) and/or Formula (Ia) have been shown to inhibit ALK tyrosine kinase, and one or more kinases chosen from IGF1R kinase, EGFR kinase, FGFR kinase and/or INSR kinase. In some embodiments, Compounds of Formula (I) and/or Formula (Ia) are useful for their ability to inhibit ALK kinase activity and inhibit IGF1R kinase activity. In some embodiments, Compounds of Formula (I) and/or Formula (Ia) are useful for their ability to inhibit ALK kinase activity and inhibit EGFR kinase activity. In some embodiments, Compounds of Formula (I) and/or Formula (Ia) are useful for their ability to inhibit ALK kinase activity and inhibit FGFR kinase activity. In some embodiments, Compounds of Formula (I) and/or Formula (Ia) are useful for their ability to inhibit ALK kinase activity and inhibit INSR kinase activity.

Compounds of Formula (I) and/or Formula (Ia) should also be useful as standards and reagents in determining the ability of a potential pharmaceutical to inhibit tyrosine kinases, particularly the ALK family. These would be provided in commercial kits comprising a compound of this invention.

Although the pharmacological properties of compounds of the Formula (I) and/or Formula (Ia) may vary with structural change, typical compounds of the Formula (I) and/or Formula (Ia) possess ALK inhibitory activity at $IC_{50}$ concentrations (concentrations to achieve 50% inhibition or doses at a level below 30 μM.

ALK kinase activity was determined by measuring the kinase's ability to phosphorylate a tyrosine residue within a peptide substrate using a mobility shift assay on a Caliper LC3000 reader (Caliper Life Sciences, Hopkinton, Mass.), which measures fluorescence of the phosphorylated and unphosphorylated substrate and calculates a ratiometric value to determine percent turnover.

To measure ALK kinase activity, the ALK enzyme used was N-terminal GST-tagged, recombinant, human ALK, amino acids 1058-1620 (Genbank Accession number NP_004295) expressed in insect cells and activated in-vitro via autophosphorylation. This was either purchased from a commercially available source (Invitrogen, Carlsbad, Calif.) or prepared by AstraZeneca. The kinase was incubated with a FAM labeled SRCtide substrate (5FAM-GEEPLYWSFPA-KKK-NH2, AnaSpec, Fremont, Calif.), 30 μM adenosine triphosphate (ATP, at Km concentration) or 5 mM ATP, 50 mM HEPES buffer (pH 7.3), 1 mM DTT, 0.01% Tween 20, 50 μg/ml BSA and 10 mM $MgCl_2$ for 90 minutes at room temperature. After this time, the kinase reaction was stopped by adding quenching buffer containing final concentrations of 36 mM ethylenediaminetetraacetic acid (EDTA), 65 mM HEPES buffer (pH 7.3), 0.2% Coatin Reagent 3 (Caliper Life Sciences, Hopkinton, Mass.), and 0.003% Tween 20. The reaction was performed in 384 well microtitre plates and the reaction products were detected using the Caliper LC3000 Reader in the presence of separation buffer consisting of 100 mM HEPES (pH 7.3), 15.8 mM EDTA, 0.1% Coatin Reagent 3 (Caliper, Mass.), 0.015% Brij-35, 5% DMSO, and 5.6 mM $MgCl_2$. The separation conditions set up on the Caliper LC3000 were −1.7 PSI, −400V upstream voltage, −2000V downstream voltage, 0.2 second sample sip, 45 second post sip, and 150 seconds final delay. The percentage of inhibition of ALK enzyme activity by compounds were measured based on Max signals (DMSO control) and Min signals (EDTA control) in the plates. Data was graphed and $IC_{50}$s calculated by IDBS ActivityBase program.

When tested in the assay described above, the Examples listed below in Table 1 had ALK inhibitory activity measured at the indicated $IC_{50}$s (μM).

TABLE 1

| Example | ALK Enzyme $IC_{50}$ (μM)* | ALK Enzyme $IC_{50}$ (μM)** |
|---|---|---|
| 1 | 0.015 | 0.021 |
| 2 | 0.023 | — |
| 3 | 0.070 | — |
| 4 | 0.052 | — |
| 5 | 0.030 | — |
| 6 | 0.058 | — |
| 7 | 0.041 | 0.079 |

TABLE 1-continued

| Example | ALK Enzyme IC$_{50}$ (μM)* | ALK Enzyme IC$_{50}$ (μM)** |
|---|---|---|
| 8 | 0.061 | — |
| 9 | 0.050 | 0.068 |
| 10 | 0.020 | — |
| 11 | 0.086 | — |
| 12 | 0.023 | 0.021 |
| 13 | 0.050 | — |
| 14 | 0.024 | — |
| 15 | 0.144 | — |
| 16 | 0.019 | — |
| 17 | 0.047 | — |
| 18 | 0.027 | — |
| 19 | 0.052 | — |
| 20 | 0.029 | — |
| 21 | 0.235 | — |
| 22 | 0.057 | — |
| 23 | 0.028 | — |
| 24 | 0.140 | — |
| 25 | 0.390 | — |
| 26 | 0.113 | — |
| 27 | 0.033 | — |
| 28 | 0.024 | — |
| 29 | 0.021 | — |
| 30 | 0.182 | 0.151 |
| 31 | 0.088 | 0.136 |
| 32 | 0.343 | 0.356 |
| 33 | 0.025 | 0.030 |
| 34 | 0.148 | — |
| 35 | 0.098 | — |
| 36 | 1.484 | — |
| 37 | 0.244 | — |
| 38 | 0.258 | — |
| 39 | 0.225 | — |
| 40 | 0.198 | — |
| 41 | 0.068 | — |
| 42 | nt | 0.083 |
| 43 | nt | 0.158 |
| 44 | nt | 0.020 |
| 45 | nt | 0.061 |
| 46 | nt | 0.039 |
| 47 | nt | nt |
| 50 | nt | 0.022 |
| 51 | nt | 0.031 |

*= Data points are geometric means encompassing multiple test runs and were presented in the filing(s) to which the present application claims priority.
**= Data points are geometric means (cumulative) encompassing multiple test re-runs, some of which have been obtained since the priority filings to which the present application claims priority.
nt = not tested.

Examples 1, 9 and 10 were additionally tested using an alternate ALK protocol as follows: ALK (h) was incubated with 8 mM MOPS pH 7.0, 0.2 mM EDTA, 250 μM KKKSPGEYVNIEFG, 10 mM MgAcetate and [γ-33P-ATP] (specific activity approx. 500 cpm/pmol, concentration as required). The reaction was initiated by the addition of the MgATP mix. After incubation for 40 minutes at room temperature, the reaction was stopped by the addition of 3% phosphoric acid solution. 10 μL of the reaction was spotted onto a P30 filtermat and washed three times for 5 minutes in 75 mM phosphoric acid and once in methanol prior to drying and scintillation counting. When tested in the assay described above, Examples 1, 9 and 10 each had ALK inhibitory activities (IC$_{50}$s (μM)) of 0.004, 0.019, and 0.006, respectively.

In one aspect, there is provided a compound of Formula (I) and/or Formula (Ia), and/or a pharmaceutically acceptable salt thereof, for use as a medicament.

In another aspect, there is provided the use of a compound of Formula (I) and/or Formula (Ia), and/or a pharmaceutically acceptable salt thereof, in the manufacture of a medicament for the treatment or prophylaxis of at least one of: carcinoma, hematopoietic tumours of lymphoid lineage, hematopoietic tumors of myeloid lineage, tumors of mesenchymal origin, melanoma, seminoma, tetratocarcinoma, neuroblastoma, and glioma.

In another aspect, there is provided the use of a compound of Formula (I) and/or Formula (Ia), and/or a pharmaceutically acceptable salt thereof, in the manufacture of a medicament for the treatment of at one of: non small cell lung cancer, breast cancer, neuroblastoma, anaplastic large cell lymphoma, esophogeal squamos cell carcinoma, and inflammatory myofibroblastic tumors.

In another aspect, there is provided the use of a compound of Formula (I) and/or Formula (Ia), and/or a pharmaceutically acceptable salt thereof, in the manufacture of a medicament for the treatment of cancer.

In another aspect, there is provided the use of a compound of Formula (I) and/or Formula (Ia), and/or a pharmaceutically acceptable salt thereof, in the manufacture of a medicament for the production of an anti-proliferative or pro-apoptotic effect, in a warm-blooded animal such as man.

In another aspect, there is provided the use of a compound of Formula (I) and/or Formula (Ia), and/or a pharmaceutically acceptable salt thereof, in the manufacture of a medicament for the production of a ALK inhibitory effect in a warm blooded animal such as man.

In another aspect, there is provided a method for the treatment or prophylaxis of at least one of: carcinoma, hematopoietic tumours of lymphoid lineage, hematopoietic tumors of myeloid lineage, tumors of mesenchymal origin, melanoma, seminoma, tetratocarcinoma, neuroblastoma and glioma, said method comprising administering to said animal an effective amount of a compound of Formula (I) and/or Formula (Ia), and/or a pharmaceutically acceptable salt thereof.

In another aspect, there is provided a method for treating at least one of: non small cell lung cancer, breast cancer, neuroblastoma, anaplastic large cell lymphoma, esophogeal squamos cell carcinoma, and inflammatory myofibroblastic tumors, in a warm-blooded animal such as man, said method comprising administering to said animal an effective amount of a compound of Formula (I) and/or Formula (Ia), and/or a pharmaceutically acceptable salt thereof.

In another aspect, there is provided a method for producing an anti-proliferative or pro-apoptotic effect in a warm-blooded animal such as man, said method comprising administering to said animal an effective amount of a compound of Formula (I) and/or Formula (Ia), and/or a pharmaceutically acceptable salt thereof.

In another aspect, there is provided a method for producing an ALK inhibitory effect in a warm-blooded animal such as man, said method comprising administering to said animal an effective amount of a compound of Formula (I) and/or Formula (Ia), and/or a pharmaceutically acceptable salt thereof.

In another aspect, there is provided a method for treating cancer in a warm-blooded animal such as man, said method comprising administering to said animal an effective amount of a compound of Formula (I) and/or Formula (Ia), and/or a pharmaceutically acceptable salt thereof.

In another aspect, there is provided a compound of Formula (I) and/or Formula (Ia), and/or a pharmaceutically acceptable salt thereof, for use in the treatment of at least one of: carcinoma, hematopoietic tumours of lymphoid lineage, hematopoietic tumors of myeloid lineage, tumors of mesenchymal origin, melanoma, seminoma, tetratocarcinoma, neuroblastoma, and glioma.

In another aspect, there is provided a compound of Formula (I) and/or Formula (Ia), and/or a pharmaceutically acceptable salt thereof, for use in the treatment of at one of: non small cell lung cancer, breast cancer, neuroblastoma, anaplastic large cell lymphoma, esophogeal squamos cell carcinoma, and inflammatory myofibroblastic tumors.

In still another aspect, there is provided a compound of Formula (I) and/or Formula (Ia), and/or a pharmaceutically acceptable salt thereof, for use in the production of an antiproliferative or pro-apoptotic effect, in a warm-blooded animal such as man.

In another aspect, there is provided a compound of Formula (I) and/or Formula (Ia), and/or a pharmaceutically acceptable salt thereof, for use in the production of an ALK inhibitory effect in a warm-blooded animal such as man.

In another aspect, there is provided a compound of Formula (I) and/or Formula (Ia), and/or a pharmaceutically acceptable salt thereof, for use in the treatment of cancer in a warm-blooded animal such as man.

In another aspect, there is provided a pharmaceutical composition comprising a compound of Formula (I) and/or Formula (Ia), and/or a pharmaceutically acceptable salt thereof, and at least one pharmaceutically acceptable carrier, diluent, or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In some embodiments, compounds and/or compositions according to the present invention can be administered orally (i.e., I.P.O., also known as per os).

The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 2 g of an active ingredient. In some embodiments, dosage unit forms contain about 1 mg to about 1 g of an active ingredient. In some embodiments, dosage unit forms contain about 1 mg to about 800 mg of an active ingredient. In some embodiments, dosage unit forms contain about 1 mg to about 500 mg of an active ingredient. In some embodiments, dosage unit forms contain about 150 mg to about 1 g of an active ingredient. In some embodiments, dosage unit forms contain about 150 mg to about 750 mg of an active ingredient. In some embodiments, dosage unit forms contain about 150 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

As stated above the size of the dose required for the therapeutic or prophylactic treatment of a particular disease state will necessarily be varied depending on the host treated, the route of administration and the severity of the illness being treated. A daily dose in the range of 0.1-50 mg/kg may be employed. Accordingly, the optimum dosage may be determined by the practitioner who is treating any particular patient.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines including 5-fluorouracil and tegafur, raltitrexed, methotrexate, cytosine arabinoside and hydroxyurea); antitumor antibiotics (for example anthracyclines such as adriamycin, bleomycin, doxorubicin, daunomycin, epirubicin, idarubicin, mitomycin-C, dactinomycin and mithramycin); antimitotic agents (for example vinca alkaloids such as vincristine, vinblastine, vindesine and vinorelbine and taxoids such as taxol and taxotere); and topoisomerase inhibitors (for example epipodophyllotoxins such as etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors such as marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase (MEK1/2) and for example inhibitors of protein kinase B (PKB/Akt), for example inhibitors of Src tyrosine kinase family and/or Abelson (Abl) tyrosine kinase family such as AZD0530 and dasatinib (BMS-354825) and imatinib mesylate (Gleevec™); and any agents that modify STAT signaling;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies and approaches using the immunomodulatory drugs thalidomide and lenalidomide [Revlimid®]; and (x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ compounds of this invention, and/or pharmaceutically acceptable salts thereof, within the dosage range described hereinbefore and the other pharmaceutically-active agent within its approved dosage range.

In addition to its use in therapeutic medicine, compounds of Formula (I) and/or Formula (Ia) and/or pharmaceutically acceptable salts thereof are also useful as pharmacological tools in the development and standardization of in vitro and in vivo test systems for the evaluation of the effects of inhibitors of ALK in laboratory animals such as cats, dogs, rabbits, monkeys, rats and mice, as part of the search for new therapeutic agents.

In any of the above-mentioned pharmaceutical composition, process, method, use, medicament, and manufacturing features of the instant invention, any of the alternate embodiments of compounds of the invention described herein also apply.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

EXAMPLES

The invention will now be further described with reference to the following illustrative Examples in which, unless stated otherwise:
(i) temperatures are given in degrees Celsius (° C.); operations are carried out at room temperature or ambient temperature, that is, in a range of 18-25° C.;
(ii) organic solutions were dried over anhydrous magnesium sulfate unless otherwise stated;
(iii) chromatography means flash chromatography on silica gel; thin layer chromatography (TLC) was carried out on silica gel plates;
(iv) in general, the course of reactions was followed by TLC or liquid chromatography/mass spectroscopy and reaction times are given for illustration only;
(v) final products have satisfactory proton nuclear magnetic resonance (NMR) spectra and/or mass spectra data;
(vi) yields are given for illustration only and are not necessarily those which can be obtained by diligent process development; preparations were repeated if more material was required;
(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;
(viii) chemical symbols have their usual meanings;
(ix) solvent ratio was given in volume:volume (v/v) terms;
(x) "ISCO" refers to normal phase flash column chromatography using pre-packed silica gel cartridges (12 g, 40 g etc.), used according to the manufacturer's instructions, obtained from ISCO, Inc, 4700 Superior Street Lincoln, Nebr., USA;
(xi) "Gilson® chromatography" refers to chromatography using a YMC-AQC 18 reversed phase HPLC Column (unless otherwise indicated) with dimension 20 mm/100 and 50 mm/250 in $H_2O$/MeCN with 0.1% TFA as mobile phase (unless otherwise stated), used according to the manufacturer's instructions, obtained from Gilson®, Inc. 3000 Parmenter Street, Middleton, Wis. 53562-0027, U.S.A;
(xii) "Biotage®" refers to normal phase flash column chromatography using pre-packed silica gel cartridges (12 g, 40 g, 80 g etc.), used according to the manufacturer's instructions, obtained from Biotage® Inc, 1725 Discovery Drive Charlotteville, Va. 22911, USA;
(xiii) "SFC (super critical fluid chromatography)" refers to Analytical SFC (ASC-1000 Analytical SFC System with a diode array detector) and/or Preparative SFC (APS-1000 AutoPrep Preparative SFC), used according to the manufacturer's instruction, obtained from SFC Mettler Toledo AutoChem, Inc. 7075 Samuel Morse Drive Columbia Md. 21046, USA.;
(xiv) Chiralcel OJ® and Chiralcel AD-H®, Chiralcel AD-S® or Chiralpak® columns are used according to the manufacturer's instruction, and are obtained from Chiral Technologies, Inc. 800NorthFivePointsRoad WestChester, Pa. 19380, USA;
(xv) Parr Hydrogenator or Parr shaker type hydrogenators are systems for treating chemicals with hydrogen in the presence of a catalyst at pressures up to 5 atmospheres (60 psi) and temperatures to 80° C.; and
(xvi) the following abbreviations may have been used:

| | |
|---|---|
| BINAP | 2,2'-bis(diphenylphosphino)-1,1'-binapthyl |
| Boc$_2$O | tert-butyloxycarbonyl anhydride |
| DAST | Diethylaminosulfur trifluoride |
| DCM | dichloromethane |
| DIPEA | N, N-diisopropylethylamine |
| DMF | N,N-dimethylformamide |
| dppf | 1,1'-bis(diphenylphosphino)ferrocene |
| DMAP | 4-dimethylaminopyridine |
| DMSO | dimethylsulfoxide |
| e.e. | entantiomeric excess |
| EtOAc | ethyl acetate |
| Et$_2$O | diethyl ether |
| GC | gas chromatography |
| HPLC | high-performance liquid chromatography |
| h or hr | hours |
| LDA | Lithium diisopropylamide |
| mins | minutes |
| NMP | N-methylpyrrolidone |
| o/n | overnight |
| Pd$_2$(dba)$_3$ | Tris(dibenzylideneacetone)dipalladium(0) |
| iPrOH | i-propanol |
| rac. | Racemic |
| RT | room temperature |
| TBME | tert-butylmethyl ether |
| TEA | triethylamine |
| TFA | trifluoroacetic acid |
| THF | tetrahydrofuran |
| TMS | trimethyl silyl |
| Tosyl, Ts | para-toluenesulfonyl. |

Intermediate 1

3-(2-Chloro-5-methylpyrimidin-4-yl)-1H-indole

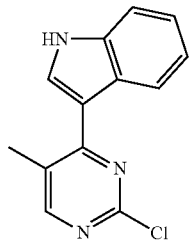 [SMILES: Cc1cnc(Cl)nc1-c1c[nH]c2ccccc12]

Methylmagnesium iodide (3 M in diethyl ether, 30.7 mL, 92.02 mmol) was added over 20 min to a solution of 1H-indole (7.19 g, 61.35 mmol) in DCE (25 mL) under nitrogen at 0° C. 2,4-Dichloro-5-methylpyrimidine (10 g, 61.35 mmol) in DCE (20 mL) was then added slowly to the reaction mixture over 20 min at 0° C. and the reaction mixture was stirred for an additional 30 min at 0° C. The reaction mixture was then allowed to warm up to RT and stirred at 30 min. The reaction mixture was then cooled to 0° C. and water (50 mL) was slowly added. The resultant yellow solids were collected by vacuum filtration. The solids were then suspended in 10% aqueous citric acid solution (150 mL) and stirred for 10 min, filtered, then washed with water and diethyl ether to give the title product. (8.10 g, 54.2%) as a yellow solid.

$^1$H NMR (300 MHz, CDCl$_3$) δ ppm 10.74 (br. s., 1H), 8.47-8.44 (m, 1H), 8.22 (s, 1H), 7.73 (d, 1H), 7.40-7.36 (m, 1H), 7.21-7.17 (m, 2H), 2.39 (s, 3H). m/z 244.

INTERMEDIATES 2 TO 5 were prepared from the indicated starting materials using a method similar to the one described for the synthesis of INTERMEDIATE 1:

Intermediate 2

3-(2,5-Dichloropyrimidin-4-yl)-1H-indole

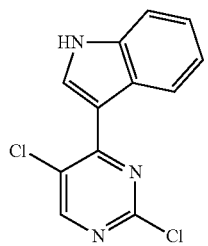 [SMILES: Clc1ncc(Cl)c(-c2c[nH]c3ccccc23)n1]

Starting materials: 2,4,5-trichloropyrimidine and 1H-indole. m/z 265.

Intermediate 3

3-(2-Chloro-5-fluoropyrimidin-4-yl)-1H-indole

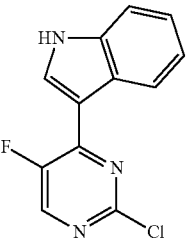 [SMILES: Fc1cnc(Cl)nc1-c1c[nH]c2ccccc12]

Starting materials: 2,4-dichloro-5-fluoropyrimidine and 1H-indole. m/z 248.

Intermediate 4

3-(2-Chloro-5-(trifluoromethyl)pyrimidin-4-yl)-1H-indole

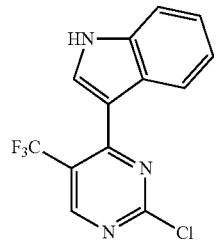 [SMILES: FC(F)(F)c1cnc(Cl)nc1-c1c[nH]c2ccccc12]

Starting materials: 2,4-dichloro-5-(trifluoromethyl)pyrimidine and 1H-indole. m/z 298.

Intermediate 5

3-(5-Bromo-2-chloropyrimidin-4-yl)-1H-indole

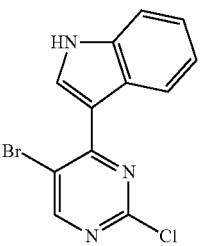

Starting materials: 5-bromo-2,4-dichloropyrimidine and 1H-indole. m/z 309.

Intermediate 6

3-(5-Bromo-2-chloropyrimidin-4-yl)-1-tosyl-1H-indole

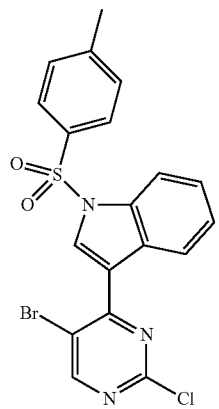 [SMILES: Cc1ccc(S(=O)(=O)n2cc(-c3nc(Cl)ncc3Br)c3ccccc32)cc1]

3-(5-Bromo-2-chloropyrimidin-4-yl)-1H-indole (INTERMEDIATE 5, 1.23 g, 4 mmol) in THF (40.0 ml) and DMF (5 ml) was cooled to −10° C. Sodium hydride (0.19 g, 4.80 mmol) was added and the reaction was stirred at −10° C. for 30 min. 4-Methylbenzene-1-sulfonyl chloride (0.84 g, 4.40 mmol) was then added. The reaction mixture was allowed to warm to RT and stirred for 15 h. Water (10 mL) was added and the resultant solids were collected by vacuum filtration to give the title product (1.36 g, 73.5%).

$^1$H NMR (400 MHz, DMSO-$d_6$) δ ppm 9.11 (s, 1H), 8.81 (s, 1H), 8.15 (d, 1H), 8.09-7.93 (m, 3H), 7.56-7.35 (m, 4H), 2.34 (s, 3H). m/z 463.

Intermediate 7

1-Fluoro-5-methoxy-2-methyl-4-nitrobenzene

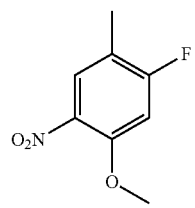

Hydrogen fluoride (70%) in pyridine (47.4 ml, 0.48 mol) in a plastic separatory funnel was added dropwise over 20 min. to pyridine (16 mL) in a plastic bottle at −78° C. (dry ice/acetone bath) under nitrogen. Note: reaction was exothermic. After the addition was complete, the reaction was stirred for 10 min. at −78° C. 5-Methoxy-2-methyl-4-nitroaniline (9.11 g, 0.05 mol) was then added and the reaction mixture was stirred for an additional 10 min. at −78° C. Sodium nitrite (5.8 g, 0.08 mol) was then added and the reaction mixture was stirred an additional 10 min. at −78° C. The reaction mixture was allowed to warm to RT and then heated to 60° C. for 2 h. The reaction mixture was then allowed to cool to RT and an ice/water mixture (300 mL) was added. The resultant precipitates were collected by vacuum filtration, washed with water and dried under vacuum. The solid product was recrystallized from methylcyclohexane to give yellow crystals as the title product (5.8 g, 63%).

$^1$H NMR (300 MHz, CHLOROFORM-d) δ ppm 7.82 (d, 1H), 6.75 (d, 1H), 3.93 (s, 3H), 2.25 (d, 3H).

Intermediate 8 tert-Butyl 4-(1-(3-methoxy-4-nitrophenyl)piperidin-4-yl)piperazine-1-carboxylate

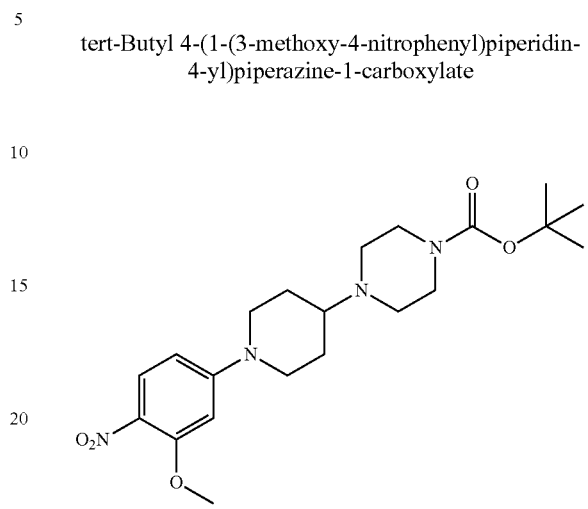

tert-Butyl 4-(piperidin-4-yl)piperazine-1-carboxylate (1.842 g, 6.84 mmol) was added to a stirring mixture of 4-fluoro-2-methoxy-1-nitrobenzene (1.17 g, 6.84 mmol) and K$_2$CO$_3$ (2.83 g, 20.51 mmol) in acetonitrile (15 mL) and the reaction mixture was stirred at 90° C. for 15 h. The reaction mixture was filtered and concentrated in vacuo. The crude residue was purified by chromatography on silica gel (hexanes/EtOAc) to give the title product (2.5 g, 87%). m/z 421.

INTERMEDIATES 9 to 11 were prepared from the indicated starting materials using a method similar to the one described for the synthesis of INTERMEDIATE 8:

Intermediate 9 tert-Butyl 1-(3-methoxy-4-nitrophenyl)piperidin-4-ylcarbamate

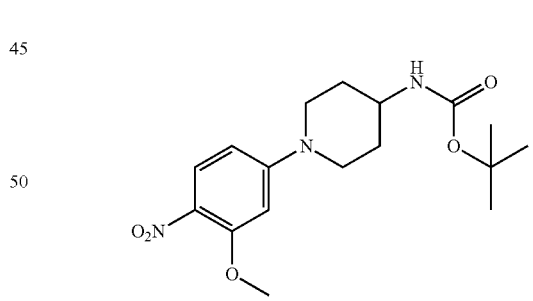

Starting materials: 4-fluoro-2-methoxy-1-nitrobenzene and tent-butyl piperidin-4-ylcarbamate. m/z 352.

Intermediated 10 tert-Butyl 1-(3-methoxy-4-nitrophenyl)piperidin-4-yl (methyl)carbamate

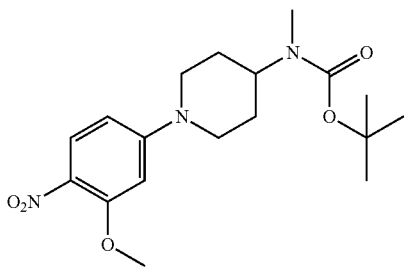 [SMILES: COc1cc(N2CCC(N(C)C(=O)OC(C)(C)C)CC2)ccc1[N+](=O)[O-]]

Starting materials: 4-fluoro-2-methoxy-1-nitrobenzene and tert-butyl methyl(piperidin-4-yl)carbamate. m/z 366.

Intermediate 11

1-(3-Methoxy-4-nitrophenyl)-N,N-dimethylpiperidin-4-amine

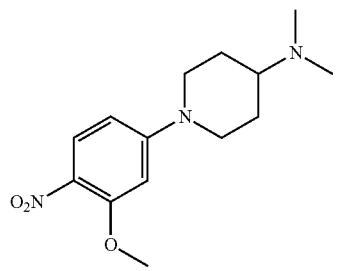 [SMILES: COc1cc(N2CCC(N(C)C)CC2)ccc1[N+](=O)[O-]]

Starting materials: 4-fluoro-2-methoxy-1-nitrobenzene and N,N-dimethylpiperidin-4-amine. m/z 280.

Intermediate 12

1-(1-(5-Methoxy-2-methyl-4-nitrophenyl)piperidin-4-yl)-4-methylpiperazine

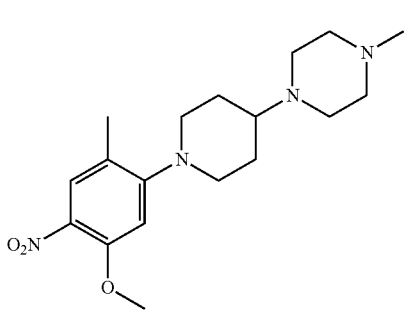

1-Fluoro-5-methoxy-2-methyl-4-nitrobenzene (INTERMEDIATE 7, 0.370 g, 2.00 mmol), 1-methyl-4-(piperidin-4-yl)piperazine (0.367 g, 2.00 mmol), and potassium carbonate (0.415 g, 3.00 mmol) in DMSO (2.0 mL) were stirred at 80° C. for 15 h. DCM (20 mL) and water (20 mL) were added to the reaction mixture. The organic layer was washed with water and brine, dried over sodium sulfate, filtered and concentrated in vacuo to give the title product. (0.640 g, 92%).

$^1$H NMR (400 MHz, CHLOROFORM-d) δ ppm 7.85-7.77 (m, 1H), 6.54 (s, 1H), 3.94 (s, 3H), 3.35 (d, 2H), 2.78-2.63 (m, 5H), 2.60-2.48 (m, 4H), 2.32 (s, 3H), 2.24 (s, 3H), 1.99 (d, 2H), 1.72 (dd, 2H). m/z 349.

INTERMEDIATES 13 TO 15 were prepared from the indicated starting materials using a method similar to the one described for the synthesis of INTERMEDIATE 12:

Intermediate 13

1-(1-(3-Methoxy-4-nitrophenyl)piperidin-4-yl)-4-methylpiperazine

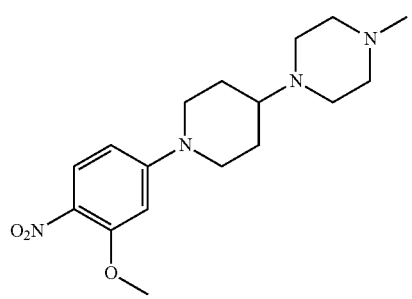 [SMILES: COc1cc(N2CCC(N3CCN(C)CC3)CC2)ccc1[N+](=O)[O-]]

Starting Materials: 4-fluoro-2-methoxy-1-nitrobenzene and 1-methyl-4-(piperidin-4-yl)piperazine.

$^1$H NMR (400 MHz, METHANOL-$d_4$) δ ppm 7.95 (d, 1H), 6.65-6.49 (m, 2H), 4.11 (d, 2H), 3.95 (s, 3H), 3.05-2.95 (m, 2H), 2.69 (br. s., 4H), 2.64-2.38 (m, 5H), 2.31 (s, 3H), 2.061-0.95 (m, 2H), 1.67-1.49 (m, 2H). m/z 335.

Intermediate 14 tert-Butyl 1-(5-methoxy-2-methyl-4-nitrophenyl)piperidin-4-ylcarbamate

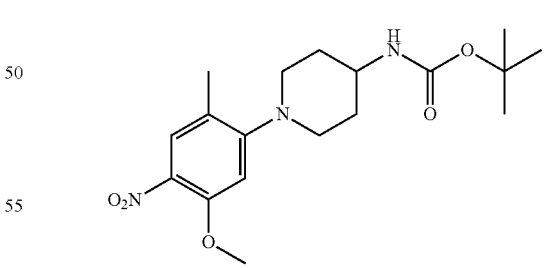

Starting Materials: 1-fluoro-5-methoxy-2-methyl-4-nitrobenzene (INTERMEDIATE 7) and tert-butyl piperidin-4-ylcarbamate.

$^1$H NMR (400 MHz, CHLOROFORM-d) δ ppm 7.82 (s, 1H), 6.55 (s, 1H), 4.53 (br. s., 1H), 4.05-3.85 (m, 3H), 3.65 (br. s., 1H), 3.24 (d, 2H), 2.93-2.70 (m, 2H), 2.29-2.14 (m, 3H), 2.09 (d, 2H), 1.70-1.53 (m, 2H), 1.47 (s, 9H). m/z 366.

Intermediate 15

1-(5-Methoxy-2-methyl-4-nitrophenyl)-N,N-dimethylpiperidin-4-amine

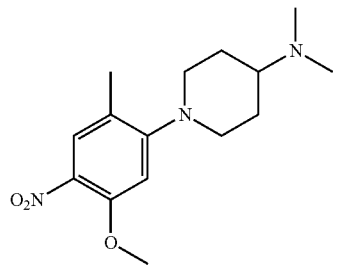 [SMILES: COc1cc(N2CCC(N(C)C)CC2)c(C)cc1[N+](=O)[O-]]

Starting Materials: 1-fluoro-5-methoxy-2-methyl-4-nitrobenzene (INTERMEDIATE 7) and N,N-dimethylpiperidin-4-amine. m/z 294.

Intermediate 16

8-(5-Methoxy-2-methyl-4-nitrophenyl)-1,4-dioxa-8-azaspiro[4.5]decane

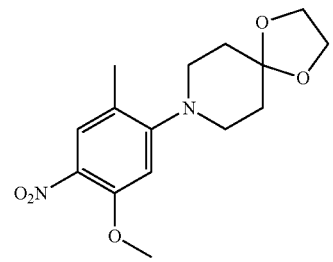 [SMILES: COc1cc(N2CCC3(CC2)OCCO3)c(C)cc1[N+](=O)[O-]]

Starting Materials: 1-fluoro-5-methoxy-2-methyl-4-nitrobenzene (INTERMEDIATE 7) and 1,4-dioxa-8-azaspiro[4.5]decane. m/z 309.

Intermediate 17

1-(3-Methoxy-4-nitrophenyl)piperidin-4-ol

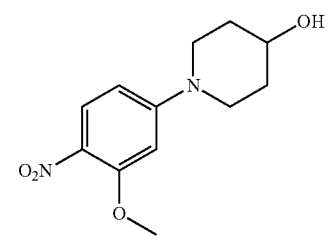 [SMILES: COc1cc(N2CCC(O)CC2)ccc1[N+](=O)[O-]]

Potassium carbonate (4.85 g, 35.06 mmol) was added to a stirring solution of 4-fluoro-2-methoxy-1-nitrobenzene (5.0 g, 29.22 mmol) and piperidin-4-ol (2.96 g, 29.22 mmol) in DMSO (20 mL) and the reaction mixture was heated at 90° C. for 1 h. The reaction mixture was allowed to cool to RT and water (200 mL) was added. The resultant precipitates were collected by vacuum filtration and washed with water and Et$_2$O to give the title product as a yellow solid (7.0 g, 95%).

$^1$H NMR (300 MHz, DMSO-d$_6$) δ ppm 7.87 (d, 1H), 6.58 (dd, 1H), 6.50 (d, 1H), 4.75 (d, 1H), 3.90 (s, 3H), 3.85-3.66 (m, 3H), 3.19 (m, 2H), 1.89-1.73 (m, 2H), 1.52-1.32 (m, 2H).

Intermediate 18

1-(3-Methoxy-4-nitrophenyl)piperidin-4-one

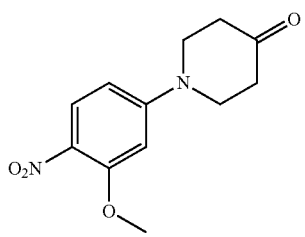 [SMILES: COc1cc(N2CCC(=O)CC2)ccc1[N+](=O)[O-]]

Dess-Martin periodinane (13.62 g, 32.11 mmol) was added to 1-(3-methoxy-4-nitrophenyl)piperidin-4-ol (INTERMEDIATE 17, 5.4 g, 21.41 mmol) in DCM (120 mL) at 0° C. and the reaction mixture was stirred for 30 min. The reaction mixture was then allowed to warm to RT and stirred for an additional 4 h. The reaction solution was poured into a mixture of 20% aqueous Na$_2$S$_2$O$_3$ (50 mL) and saturated aqueous NaHCO$_3$ (50 mL) and the biphasic mixture was stirred at RT for 1 h. The mixture was partitioned and organic layer was washed with brine, dried over sodium sulfate, filtered and concentrated in vacuo. The crude residue was purified by chromatography on silica gel (5% MeOH/DCM) to give the title product (4.28 g, 80%). m/z 251.

Intermediate 19

N-Cyclopropyl-1-(3-methoxy-4-nitrophenyl)piperidin-4-amine

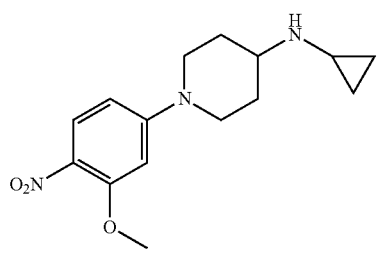 [SMILES: COc1cc(N2CCC(NC3CC3)CC2)ccc1[N+](=O)[O-]]

1-(3-Methoxy-4-nitrophenyl)piperidin-4-one (INTERMEDIATE 18, 0.70 g, 2.80 mmol), cyclopropanamine (0.160 g, 2.80 mmol) and sodium triacetoxyborohydride (0.889 g, 4.20 mmol) in DCE (15 mL)/THF (5 mL) were stirred at 25° C. for 2 h. The reaction mixture was concentrated in vacuo. The crude residue was taken up in EtOAc and washed with saturated aqueous sodium bicarbonate and brine, dried over sodium sulfate, filtered and concentrated in vacuo. The crude residue was purified by chromatography on silica gel (10% MeOH/EtOAc) to give the title product (0.76 g, 93%). m/z 292.

INTERMEDIATES 20 TO 24 were prepared from the indicated starting materials using a method similar to the one described for the synthesis of INTERMEDIATE 19:

Intermediate 20

2-(1-(3-Methoxy-4-nitrophenyl)piperidin-4-ylamino)ethanol

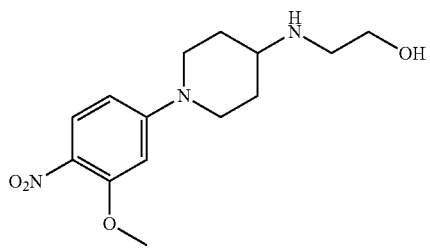 [SMILES: COc1cc(N2CCC(NCCO)CC2)ccc1[N+](=O)[O-]]

Starting materials: 1-(3-methoxy-4-nitrophenyl)piperidin-4-one (INTERMEDIATE 18) and 2-aminoethanol. m/z 296.

Intermediate 21

1-(1-(3-Methoxy-4-nitrophenyl)piperidin-4-yl)-4-(methylsulfonyl)piperazine

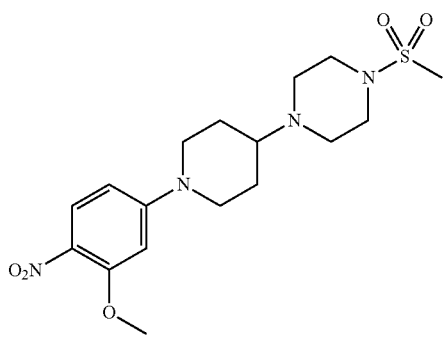 [SMILES: COc1cc(N2CCC(N3CCN(S(C)(=O)=O)CC3)CC2)ccc1[N+](=O)[O-]]

Starting materials: 1-(3-methoxy-4-nitrophenyl)piperidin-4-one (INTERMEDIATE 18) and 1-(methylsulfonyl)piperazine.

$^1$H NMR (300 MHz, DMSO-$d_6$) δ ppm 7.88 (d, 1H), 6.59 (m, 1H), 6.51 (d, 1H), 4.06 (d, 2H), 3.91 (s, 3H), 3.24-3.13 (m, 1H), 3.13-3.03 (m, 4H), 3.03-2.90 (m, 2H), 2.85 (s, 3H), 2.65-2.53 (m, 4H), 1.84 (m, 2H), 1.56-1.30 (m, 2H).

Intermediate 22

(R)-4-(3-Fluoropyrrolidin-1-yl)-1-(3-methoxy-4-nitrophenyl)piperidine

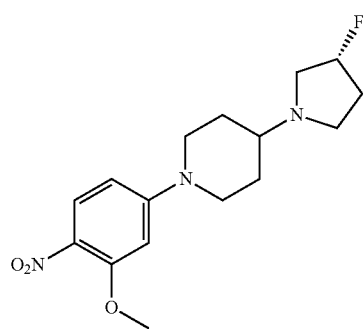 [SMILES: COc1cc(N2CCC(N3CC[C@@H](F)C3)CC2)ccc1[N+](=O)[O-]]

Starting materials: 1-(3-methoxy-4-nitrophenyl)piperidin-4-one (INTERMEDIATE 18) and (R)-3-fluoropyrrolidine. m/z 324.

Intermediate 23

1-Isopropyl-4-(1-(3-methoxy-4-nitrophenyl)piperidin-4-yl)piperazine

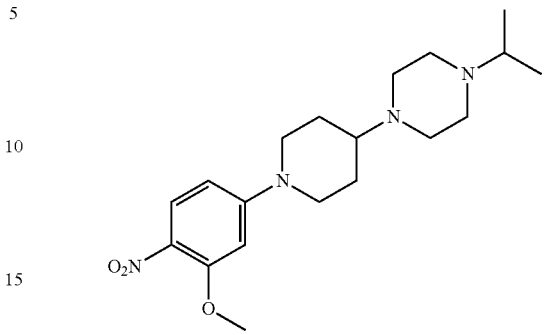

Starting materials: 1-(3-methoxy-4-nitrophenyl)piperidin-4-one (INTERMEDIATE 18) and 1-isopropylpiperazine. m/z 363.

Intermediate 24

(2S,6R)-4-(1-(3-Methoxy-4-nitrophenyl)piperidin-4-yl)-2,6-dimethylmorpholine

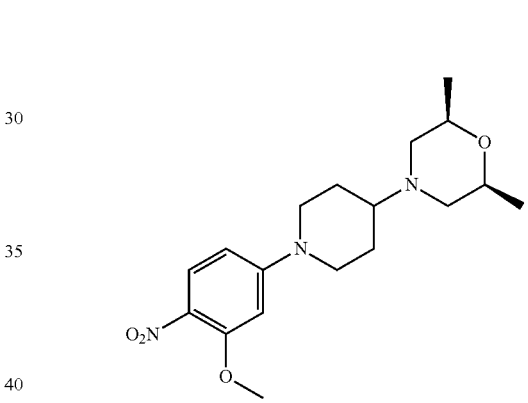

Starting materials: 1-(3-methoxy-4-nitrophenyl)piperidin-4-one (INTERMEDIATE 18) and (2S,6R)-2,6-dimethylmorpholine. m/z 350.

Intermediate 25

(R)-4-(3-Fluoropyrrolidin-1-yl)-1-(5-methoxy-2-methyl-4-nitrophenyl)piperidine

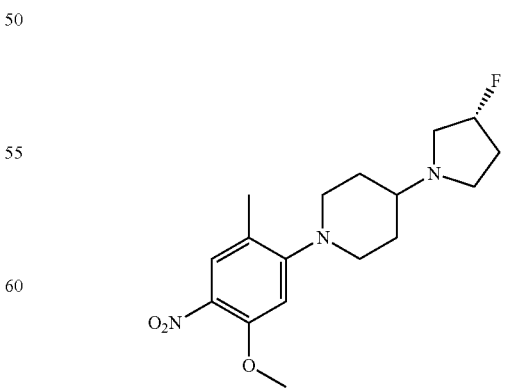

8-(5-Methoxy-2-methyl-4-nitrophenyl)-1,4-dioxa-8-azaspiro[4.5]decane (INTERMEDIATE 16, 0.350 g, 1.14 mmol)

and 4-toluenesulfonic acid hydrate (0.217 g, 1.14 mmol) in water (25 mL) were stirred under reflux for 6 h. The reaction mixture was allowed to cooled to RT and adjusted to pH 7 with potassium carbonate The mixture was concentrated in vacuo. The crude residue was taken up in EtOAc, washed with water and brine, dried over magnesium sulfate, filtered and concentrated in vacuo. To the resultant crude 1-(5-methoxy-2-methyl-4-nitrophenyl)piperidin-4-one (0.30 g, 1.14 mmol) in acetonitrile (15 mL) was added (R)-3-fluoropyrrolidine hydrochloride (0.102 g, 1.14 mmol) and sodium triacetoxyborohydride (0.481 g, 2.27 mmol) and the reaction mixture was stirred at RT for 16 h. The mixture was concentrated in vacuo and the crude residue was taken up in EtOAc and washed with 10% aqueous sodium carbonate and brine. The organic layer was separated, dried over sodium sulfate and concentrated in vacuo to give the title product which was used in the next step without further purification (0.19 g, 50%). m/z 338.

Intermediate 26

2-Methoxy-5-methyl-4-(4-(4-methylpiperazin-1-yl)piperidin-1-yl)aniline

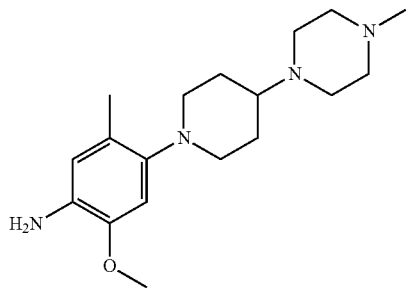

Palladium on carbon (10% Degussa Type) (100 mg, 0.94 mmol) was added to a stirring solution of 1-(1-(5-methoxy-2-methyl-4-nitrophenyl)piperidin-4-yl)-4-methylpiperazine (INTERMEDIATE 12, 697 mg, 2.00 mmol) in methanol (10 mL). The reaction mixture was then stirred under hydrogen (1 atm) at RT for 15 h. The reaction mixture was filtered through Celite® and the filtrate was concentrated in vacuo to give the title product which was used in the next step without further purification (566 mg, 66.1%). m/z 319.

INTERMEDIATES 27 to 36 were prepared from the indicated starting material using a method similar to the one described for the synthesis of INTERMEDIATE 26:

Intermediate 27

2-methoxy-4-(4-(4-methylpiperazin-1-yl)piperidin-1-yl)aniline

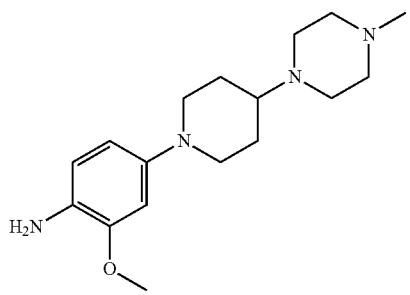

Starting material: 1-(1-(3-Methoxy-4-nitrophenyl)piperidin-4-yl)-4-methylpiperazine (INTERMEDIATE 13). m/z 305.

Intermediate 28

1-(4-Amino-3-methoxyphenyl)-N,N-dimethylpiperidin-4-amine

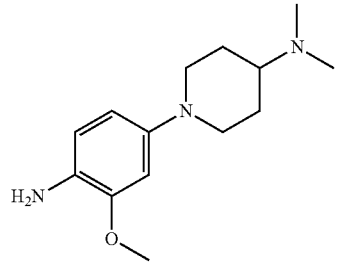 [SMILES: COc1cc(N2CCC(N(C)C)CC2)ccc1N]

Starting material: 1-(3-methoxy-4-nitrophenyl)-N,N-dimethylpiperidin-4-amine (INTERMEDIATE 11). m/z 250.

Intermediate 29 tert-Butyl 1-(4-amino-5-methoxy-2-methylphenyl)piperidin-4-ylcarbamate

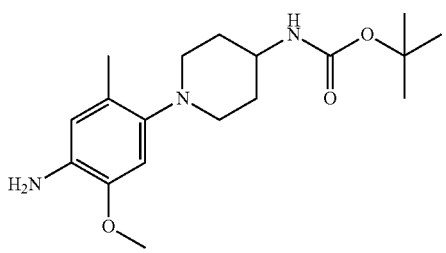

Starting material: tert-butyl 1-(5-methoxy-2-methyl-4-nitrophenyl)piperidin-4-ylcarbamate (INTERMEDIATE 14). m/z 336.

Intermediate 30

1-(4-Amino-5-methoxy-2-methylphenyl)-N,N-dimethylpiperidin-4-amine

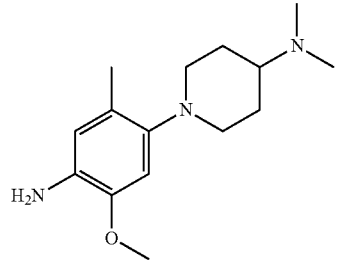

Starting material: 1-(5-methoxy-2-methyl-4-nitrophenyl)-N,N-dimethylpiperidin-4-amine (INTERMEDIATE 15). m/z 264.

Intermediate 31

2-(1-(4-Amino-3-methoxyphenyl)piperidin-4-ylamino)ethanol

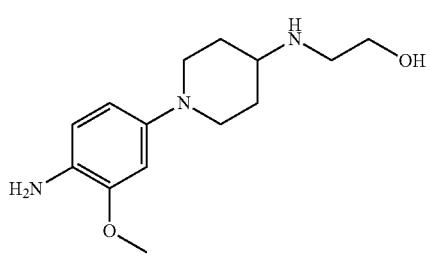

Starting material: 2-(1-(3-methoxy-4-nitrophenyl)piperidin-4-ylamino)ethanol (INTERMEDIATE 20).

¹H NMR (300 MHz, DMSO-d$_6$) δ ppm 6.52-6.48 (m, 2H), 6.29 (dd, 1H), 4.47 (br. s., 1H), 4.17 (br. s., 2H), 3.74 (s, 3H), 3.46 (br. s., 2H), 2.63 (m, 4H), 1.90-1.77 (m, 2H), 1.42-1.29 (m, 2H).

Intermediate 32

2-Methoxy-4-(4-(4-(methylsulfonyl)piperazin-1-yl)piperidin-1-yl)aniline

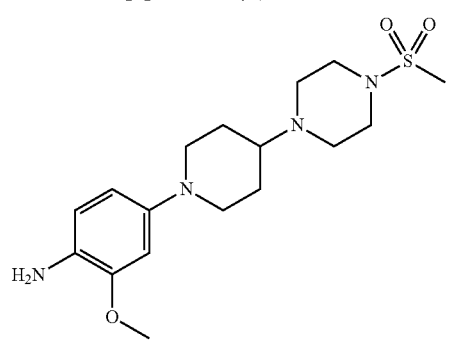

Starting material: 1-(1-(3-methoxy-4-nitrophenyl)piperidin-4-yl)-4-(methylsulfonyl)piperazine (INTERMEDIATE 21). m/z 369.

Intermediate 33

(R)-4-(4-(3-Fluoropyrrolidin-1-yl)piperidin-1-yl)-2-methoxyaniline

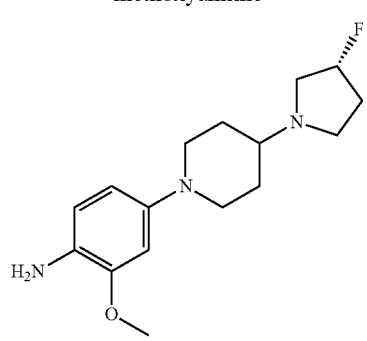

Starting material: (R)-4-(3-fluoropyrrolidin-1-yl)-1-(3-methoxy-4-nitrophenyl)piperidine (INTERMEDIATE 22). m/z 294.

Intermediate 34

4-(4-(4-Isopropylpiperazin-1-yl)piperidin-1-yl)-2-methoxyaniline

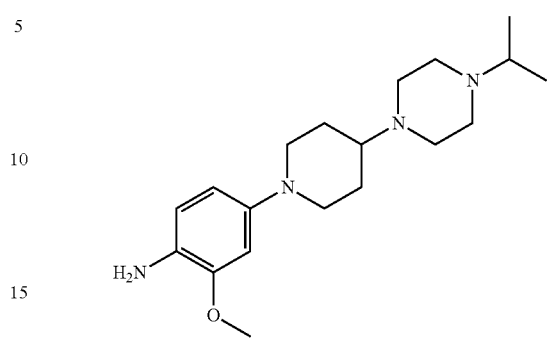

Starting material: 1-isopropyl-4-(1-(3-methoxy-4-nitrophenyl)piperidin-4-yl)piperazine (INTERMEDIATE 23). m/z 333.

Intermediate 35

4-(4-((2S,6R)-2,6-Dimethylmorpholino)piperidin-1-yl)-2-methoxyaniline

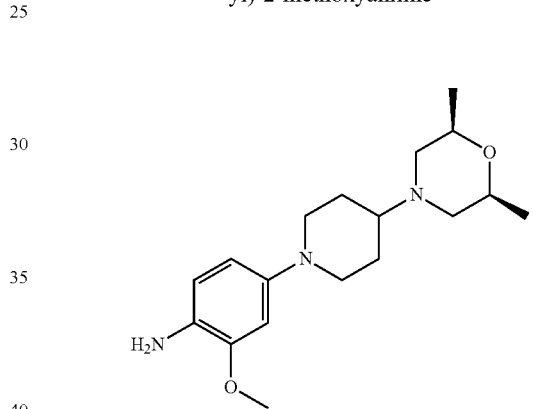

Starting material: (2S,6R)-4-(1-(3-Methoxy-4-nitrophenyl)piperidin-4-yl)-2,6-dimethylmorpholine (INTERMEDIATE 24). m/z 320.

Intermediate 36

(R)-4-(4-(3-Fluoropyrrolidin-1-yl)piperidin-1-yl)-2-methoxy-5-methylaniline

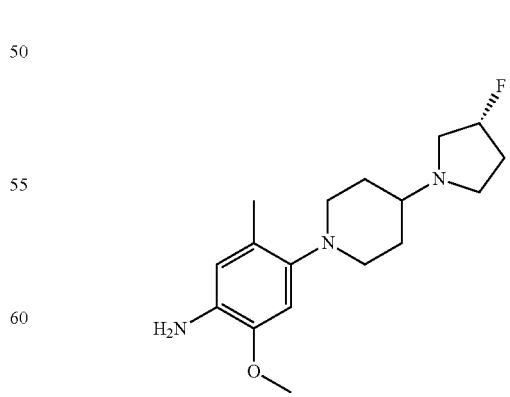

Starting material: (R)-4-(3-fluoropyrrolidin-1-yl)-1-(5-methoxy-2-methyl-4-nitrophenyl)piperidine (INTERMEDIATE 25). m/z 308.

Intermediate 37

5-Bromo-N-(2-methoxy-4-(4-(4-methylpiperazin-1-yl)piperidin-1-yl)phenyl)-4-(1-tosyl-1H-indol-3-yl)pyrimidin-2-amine

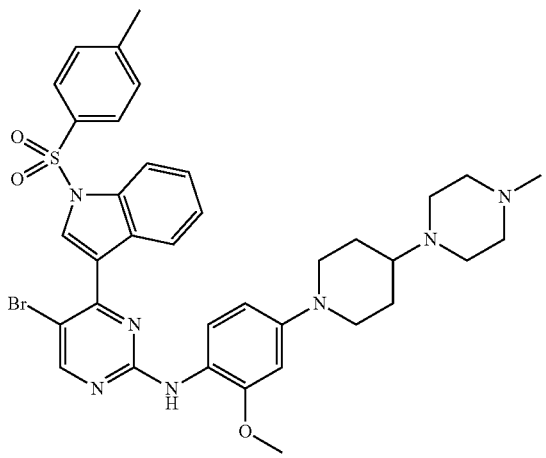 [SMILES: COc1cc(N2CCC(N3CCN(C)CC3)CC2)ccc1Nc1ncc(Br)c(-c2cn(S(=O)(=O)c3ccc(C)cc3)c3ccccc23)n1]

3-(5-Bromo-2-chloropyrimidin-4-yl)-1-tosyl-1H-indole (INTERMEDIATE 6, 372 mg, 0.83 mmol), 2-methoxy-4-(4-(4-methylpiperazin-1-yl)piperidin-1-yl)aniline (INTERMEDIATE 27, 343 mg, 0.83 mmol), and DIEA (0.145 mL, 0.83 mmol) in n-butanol (4.0 mL) were heated at 170° C. for 3 h. The reaction mixture was concentrated in vacuo and the crude residue was purified by chromatography on silica gel (10% MeOH/1% NH$_4$OH in DCM) to give the title product (320 mg, 53.9%). m/z 718.

Intermediate 38

3,3-Dimethylpiperidin-4-one

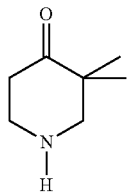

Trifluoroactic acid (4 mL, 51.92 mmol) was added to a solution of tert-butyl 3,3-dimethyl-4-oxopiperidine-1-carboxylate (2.0588 g, 9.06 mmol) in dichloromethane (12 mL). The reaction was stirred at RT for 2 h and the solution was concentrated to remove the solvent. The residue as the product was directly used in the next step without further purification. m/z 128.

Intermediate 39

1-(3-Methoxy-4-nitrophenyl)-3,3-dimethylpiperidin-4-one

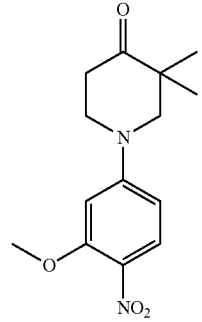

4-Fluoro-2-methoxy-1-nitrobenzene (1.550 g, 9.06 mmol), 3,3-dimethylpiperidin-4-one (INTERMEDIATE 38) (2.17 g, 9.06 mmol, TFA salt), and potassium carbonate (2.504 g, 18.12 mmol) in DMF (20 ml) were heated at 70° C. overnight. The reaction mixture was concentrated in vacuo to remove the solvent. The residue was partitioned between CH$_2$Cl$_2$ (100 mL) and water (30 mL). The organic phase was dried over MgSO$_4$ and concentrated in vacuo. The residue was purified using silica gel column (50%-100% CH$_2$Cl$_2$/Hexane) to obtain the title product (1.100 g, 43.6%).

$^1$H NMR (400 MHz, DICHLOROMETHANE-d$_2$) δ ppm 7.99 (d, 1H), 6.45 (m, 1H), 6.32 (d, 1H), 3.96 (s, 3H), 3.74 (t, 2H), 3.53 (s, 2H), 2.69 (t, 2H), 1.11-1.21 (m, 6H). m/z 279.

Intermediate 40

1-(3-Methoxy-4-nitrophenyl)-3,3-dimethylpiperidin-4-amine

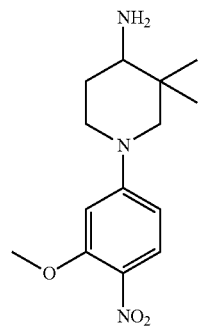

A solution of 1-(3-Methoxy-4-nitrophenyl)-3,3-dimethylpiperidin-4-one (INTERMEDIATE 39) (278 mg, 1 mmol) and ammonium acetate (771 mg, 10.0 mmol) in MeOH (5 mL) was stirred at RT overnight. Sodium cyanoborohydride (75 mg, 1.2 mmol) were added. The reaction was stirred at RT for 2 h. MeOH (20 mL) and silica gel (5 g) was added. The mixture was concentrated in vacuo. The residue was purified by chromatography on silica gel (5% MeOH and 1% NH$_4$OH in CH$_2$Cl$_2$) to give the title product (0.2 g, 72.0%).

$^1$H NMR (400 MHz, DICHLOROMETHANE-d$_2$) δ ppm 7.93 (d, 1H), 6.41 (m, 1H), 6.29 (d, 1H), 3.93 (s, 3H), 3.79-3.88 (m, 1H), 3.54 (m, 1H), 3.42 (s, 1H), 3.03 (m, 1H), 2.76 (d, 1H), 2.62 (m, 1H), 1.76 (m, 1H), 1.54 (m, 1H), 0.99 (s, 3H), 0.87 (s, 3H). m/z 280.

Intermediate 41

1-(3-Methoxy-4-nitrophenyl)-N,3,3-trimethylpiperidin-4-amine

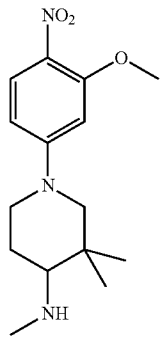 [SMILES: CNC1CCN(c2ccc([N+](=O)[O-])c(OC)c2)CC1(C)C]

INTERMEDIATE 41 was prepared from the indicated starting material using a method similar to the one described for the synthesis of INTERMEDIATE 40.

Starting material: 1-(3-Methoxy-4-nitrophenyl)-3,3-dimethylpiperidin-4-one (INTERMEDIATE 39). m/z 294.

Intermediate 42

1-(3-Methoxy-4-nitrophenyl)-N,3,3-trimethylpiperidin-4-amine

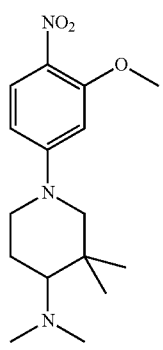 [SMILES: COc1cc(N2CCC(N(C)C)C(C)(C)C2)ccc1[N+](=O)[O-]]

A solution of 1-(3-Methoxy-4-nitrophenyl)-N,3,3-trimethylpiperidin-4-amine (INTERMEDIATE 41) (263 mg, 0.90 mmol) and formaldehyde (37% H$_2$O solution, 146 mg, 1.79 mmol) in MeOH (5 mL) was stirred at RT for 1 h. Sodium cyanoborohydride (141 mg, 2.24 mmol) was added. The reaction mixture was stirred at RT for another 1 h. Concentration in vacuo removed the solvent to yield a residue. The crude product was purified by chromatography on silica gel (5% MeOH and 0.5% NH$_4$OH in CH$_2$Cl$_2$) to give the title product (230 mg, 83% yield). m/z 308.

Intermediate 43

1-(4-Amino-3-methoxyphenyl)-3,3-dimethylpiperidin-4-amine

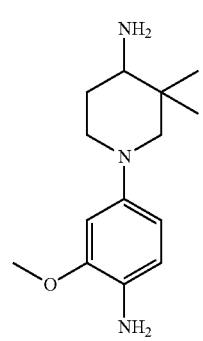

Pd/C (10% wet base, 20 mg) was added to a solution of 1-(3-methoxy-4-nitrophenyl)-3,3-dimethylpiperidin-4-amine (INTERMEDIATE 40) (0.2 g, 0.72 mmol) in methanol (4 mL). The reaction mixture was degassed and was stirred at RT under a hydrogen ballon for 4 h. The catalyst was removed by filtering the mixture through a pad of Celite®. The filtrate was concentrated to give the title product and it was used without further purification. m/z 250.

INTERMEDIATES 44 and 45 were prepared from the indicated starting material using a method similar to the one described for the synthesis of INTERMEDIATE 43.

Intermediate 44

1-(4-Amino-3-methoxyphenyl)-N,3,3-trimethylpiperidin-4-amine

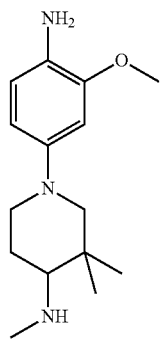 [SMILES: CNC1CCN(c2ccc(N)c(OC)c2)CC1(C)C]

Starting material: 1-(3-Methoxy-4-nitrophenyl)-N,3,3-trimethylpiperidine-4-amine (INTERMEDIATE 41). m/z 264.

Intermediate 45

1-(4-Amino-3-methoxyphenyl)-N,N,3,3-tetramethylpiperidin-4-amine

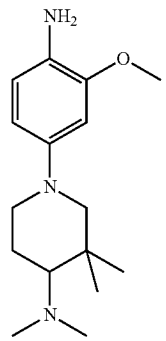 [SMILES: COc1cc(N2CCC(N(C)C)C(C)(C)C2)ccc1N]

Starting material: 1-(3-methoxy-4-nitrophenyl)-N,N,3,3-tetramethylpiperidin-4-amine (INTERMEDIATE 42). m/z 278.

Intermediate 46

(3R,4S)—N-benzyl-3-fluoropiperidin-4-amine HCl salt

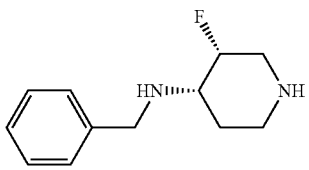

MeOH (25 mL) and HCl (4 N in dioxane) (16 ml, 64.00 mmol) were added to a flask charged with (3R,4S)-tert-butyl 4-(benzylamino)-3-fluoropiperidine-1-carboxylate (4 g, 12.97 mmol, prepared according to WO2007/071965 and references described therein) and the suspension was stirred at RT for 5 h. The solution was concentrated under reduced pressure and the white solid obtained was suspended in ether (50 ml) and filtered, dried under high vacuum to give the title product (2.90 g, 91%) (white solid).

$^1$H NMR (300 MHz, DMSO-$d_6$) δ ppm 9.95 (br. s., 2H), 8.97 (br. s., 1H), 7.66-7.63 (m, 2H), 7.45-7.43 (m, 3H), 5.50 (d, 1H), 4.26-4.21 (m, 2H), 3.70-3.54 (m, 2H), 2.99 (t, 1H), 2.30-2.26 (m, 1H), 2.13-2.02 (m, 1H).

Intermediate 47

(3R,4S)—N-benzyl-3-fluoro-1-(3-methoxy-4-nitrophenyl)piperidin-4-amine

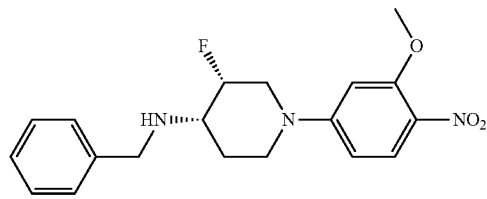 [SMILES: COc1cc(N2CC[C@H](NCc3ccccc3)[C@H](F)C2)ccc1[N+](=O)[O-]]

DMA (60 ml) and potassium carbonate (5.65 g, 40.86 mmol) were added to the flask containing 4-fluoro-2-methoxy-1-nitrobenzene (1.748 g, 10.22 mmol) and (3R,4S)—N-benzyl-3-fluoropiperidin-4-amine HCl salt (INTERMEDIATE 46, 2.5 g, 10.22 mmol). The reaction was heated to 120° C. for 5 h. The reaction mixture was cooled to rt, and filtered. The filtrate was diluted with EtOAc (50 ml) and the solution was washed with brine (2×100 ml). The organic layer was dried over Na$_2$SO$_4$, filtered, and concentrated to give a crude yellow liquid. It was purified using silica gel chromatography (80-100% EtOAc/hexane) to give the title product (2.200 g, 59.9%). m/z 361.

Intermediate 48

(3R,4S)-1-(4-amino-3-methoxyphenyl)-3-fluoropiperidin-4-amine

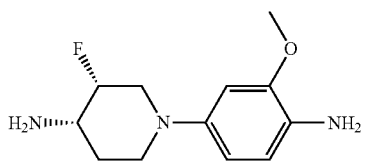 [SMILES: COc1cc(N2CC[C@H](N)[C@H](F)C2)ccc1N]

Ethanol (15 ml) and ethyl acetate (3.00 ml) were added to a flask charged with (3R,4S)—N-benzyl-3-fluoro-1-(3-methoxy-4-nitrophenyl)piperidin-4-amine (INTERMEDIATE 47) (1.4 g, 3.90 mmol) and Pd/C (0.415 g, 0.39 mmol). The flask was degassed and filled with H$_2$. The reaction was stirred at RT for 2 h under hydrogen balloon. The reaction mixture was filtered through a pad of Celite® and the filtrate was concentrated under reduced pressure to give the title product (0.840 g, 90%).

$^1$H NMR (300 MHz, DMSO-$d_6$) δ ppm 6.53-6.48 (m, 2H), 6.30 (dd, 1H), 4.63 (d, 1H), 4.21 (br. s., 2H), 3.74 (s, 3H), 3.58-3.46 (m, 1H), 3.32-3.25 (m, 2H), 2.88-2.84 (m, 1H), 2.67-2.59 (m, 1H), 1.70-1.64 (m, 2H).

Intermediate 49

3-(2,5-Dichloropyrimidin-4-yl)-1-methyl-1H-indole

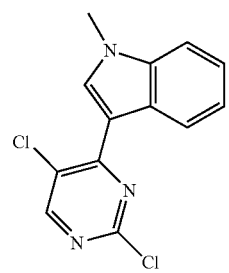 [SMILES: Cn1cc(-c2nc(Cl)ncc2Cl)c2ccccc21]

Sodium hydride (0.136 g, 3.41 mmol) and iodomethane (0.533 ml, 8.52 mmol) were added to a flask charged with 3-(2,5-dichloropyrimidin-4-yl)-1H-indole (INTERMEDIATE 2) (0.750 g, 2.84 mmol) and THF (18.40 ml). The reaction was stirred at RT for 2 h. The reaction was concentrated under reduced pressure and the crude solid obtained was washed with water and 3 mL of THF. The solid was dried under high vacuum to give the title product (0.564 g, 71.4%). m/z 278.

Intermediate 50

3-(2-chloro-5-fluoropyrimidin-4-yl)-1-methyl-1H-indole

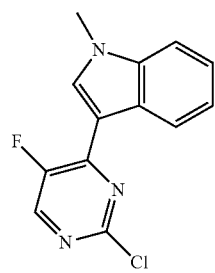

INTERMEDIATE 50 was prepared from the indicated starting material using a method similar to the one described for the synthesis of INTERMEDIATE 49.

Starting material: 3-(2-chloro-5-fluoropyrimidin-4-yl)-1H-indole (INTERMEDIATE 3). m/z 262.

Intermediate 51

4,5-Difluoro-2-nitrophenol

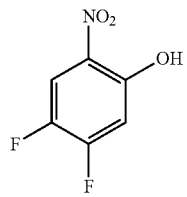

A solution of 3,4-difluorophenol (5.0 g, 38.4 mmol) and tetrabutylammonium bromide (1.239 g, 3.8 mmol) in dichloroethane (30 mL) were added into a 250 mL round-bottomed flask. The mixture was stirred for 45 min before nitric acid (86 g, 96.09 mmol) (7%) was added. The reaction was stirred at RT for 14 h. Water (100 mL) and DCM (50 mL) was added. After stirring for another 10 min, the mixture was partitioned, and the aqueous layer was extracted with DCM (1×20 mL). The combined organic layer was dried (Na$_2$SO$_4$), and concentrated to give the crude product. The crude product was purified by chromatography on silica gel using EtOAc/hexance (0-50%, 30 min). Collected fractions were concentrated to give the title product (2.0 g, 30% yield).

$^1$H NMR (300 MHz, DMSO-d6) δ ppm 11.43 (br. s., 1H), 8.15 (m, 1H), 7.16 (m, 1H).

Intermediate 52

1,2-Difluoro-4-methoxy-5-nitrobenzene

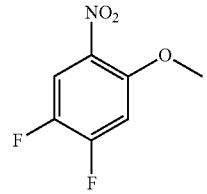

4,5-Difluoro-2-nitrophenol (INTERMEDIATE 51) (2.02 g, 11.54 mmol) and potassium carbonate (2.39 g, 17.3 mmol) were added into a 50 mL round-bottomed flask. DMF (10 mL) was added. Iodomethane (1.08 mL, 17.3 mmol) was added. The reaction mixture was stirred at RT overnight. The mixture was poured into water (60 mL) and stirred for 10 min. Filtration afforded the title product as a precipitate (1.9 g, 87% yield).

$^1$H NMR (300 MHz, DMSO-d6) δ ppm 8.23 (m, 1H), 7.63 (m, 1H), 3.94 (s, 3H).

Intermediate 53

1-(1-(2-Fluoro-5-methoxy-4-nitrophenyl)piperidin-4-yl)-4-methylpiperazine

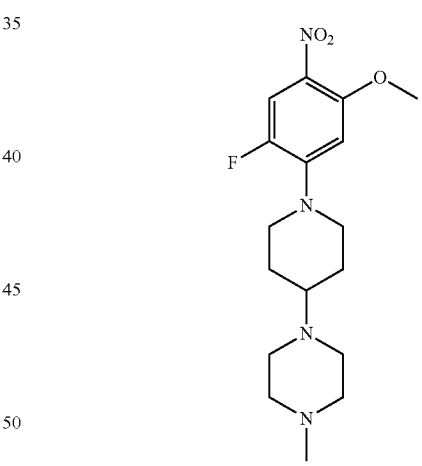

1,2-Difluoro-4-methoxy-5-nitrobenzene (INTERMEDIATE 52) (1.0 g, 5.3 mmol) and 1-methyl-4-(piperidin-4-yl)piperazine (1.066 g, 5.8 mmol) were added in a 50 mL round-bottomed flask. DMSO (6 mL) was added. The reaction was stirred at 90° C. for 1 h. After it was cooled to RT, sat. NaHCO$_3$ (20 mL) was added. After the mixture was stirred at RT for 10 min, filtration afforded the title product as an orange solid (1.7 g, 90% yield).

$^1$H NMR (300 MHz, DMSO-d6) δ ppm 7.82 (d, 1H), 6.65 (d, 1H), 3.93 (s, 3H), 3.74 (d, 2H), 2.91 (t, 2H), 2.35-2.45 (m, 5H), 2.31 (br. s., 4H), 2.14 (s, 3H), 1.86 (m, 2H), 1.42-1.66 (m, 2H).

Intermediate 54

5-Fluoro-2-methoxy-4-(4-(4-methylpiperazin-1-yl)piperidin-1-yl)aniline

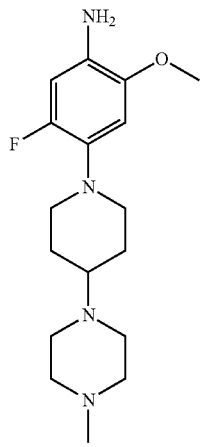

1-(1-(2-Fluoro-5-methoxy-4-nitrophenyl)piperidin-4-yl)-4-methylpiperazine (1.65 g, 4.68 mmol) was added in a 200-mL round-bottomed flask. Methanol (30 mL) was added as the solvent. Pd/C (10% wet) (0.2 g, 4.68 mmol) was added. The reaction was stirred under a hydrogen balloon for 5 h. The filtrate was collected after filtration and it was concentrated in vacuo to give the title product (1.4 g, 93% yield).

$^1$H NMR (300 MHz, DMSO-d6) δ ppm 6.53 (d, 1H), 6.41 (d, 1H), 4.57 (s, 2H), 3.72 (s, 3H), 3.04-3.22 (m, 2H), 2.58 (t, 2H), 2.31 (br. s., 7H), 2.17-2.27 (m, 2H), 2.14 (s, 3H), 1.79 (d, 2H), 1.40-1.62 (m, 2H).

Intermediate 55

5-Chloro-2-methoxy-4-(4-(4-methylpiperazin-1-yl)piperidin-1-yl)aniline

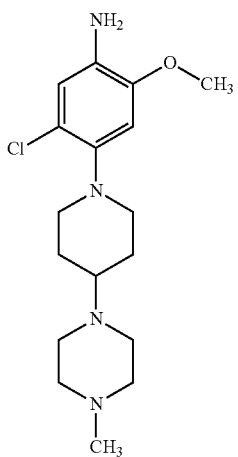 [SMILES: COc1cc(N2CCC(N3CCN(C)CC3)CC2)c(Cl)cc1N]

INTERMEDIATE 55 was prepared from the indicated starting material using a method similar to the one described for the synthesis of INTERMEDIATE 54. Starting material: 4-chloro-3-fluorophenol.

$^1$H NMR (300 MHz, DMSO-d6) δ ppm 6.65 (s, 1H), 6.63 (s, 1H), 4.62 (s, 2H), 3.75 (s, 3H), 3.11 (m, 2H), 2.53-2.65 (m, 3H), 2.18-2.42 (m, 8H), 2.15 (s, 3H), 1.80 (m, 2H), 1.41-1.64 (m, 2H).

Intermediate 56 tert-Butyl[1-(4-amino-3-methoxyphenyl)piperidin-4-yl]carbamate

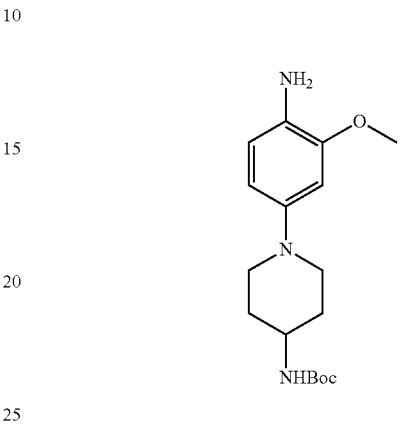

INTERMEDIATE 56 was prepared from the indicated starting material using a method similar to the one described for the synthesis of INTERMEDIATE 26.

Starting material: tert-butyl 1-(3-methoxy-4-nitrophenyl)piperidin-4-ylcarbamate (INTERMEDIATE 9). m/z 322.

Intermediate 57

Ethyl hydrogen 3-methoxy-4-nitrophenylphosphonate

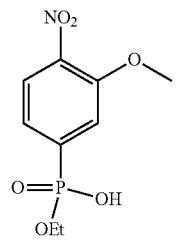 [SMILES: CCOP(=O)(O)c1ccc([N+](=O)[O-])c(OC)c1]

4-Chloro-2-methoxy-1-nitrobenzene (4.84 g, 25.8 mmol) and diethyl phosphonate (3.92 g, 28.4 mmol) were added in a 250 mL round-bottomed flask. DMF (100 mL) was added to give a yellow solution. Potassium phosphate (6.02 g, 28.4 mmol) and palladium (II) acetate (0.290 g, 1.29 mmol) were added. Nitrogen was bubbled through the solution for 20 min before xantphos (1.045 g, 1.81 mmol) was added. The reaction was heated to 130° C. and stirred at that temperature for 4 h. After it was cooled to RT, the solution was concentrated in vacuo to remove the solvent, and to the residue was added water (60 mL) and DCM (40 mL). After partition, the aqueous layer was washed with DCM (2×20 mL). The aqueous layer was acidified using 12 N HCl (10 mL), and DCM was added (50 mL). After partition and extraction with DCM (2×30 mL), the DCM solution was combined and concentrated to give the product without further purification (2.4 g, 36% yield).

$^1$H NMR (300 MHz, DMSO-d6) δ ppm 7.98 (d, 1H), 7.51 (d, 1H), 7.40 (m, 1H), 3.85-4.03 (m, 5H), 1.13-1.28 (m, 3H).

Intermediate 58

Diethenyl(3-methoxy-4-nitrophenyl)phosphane oxide

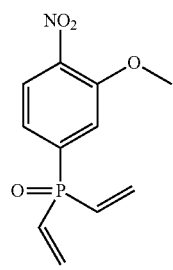 [SMILES: C=CP(=O)(C=C)c1ccc([N+](=O)[O-])c(OC)c1]

Ethyl hydrogen 3-methoxy-4-nitrophenylphosphonate (INTERMEDIATE 57) (2.0 g, 7.66 mmol) was added into a 100 mL round-bottomed flask. DMF (1.0 mL) was added to give a brown solution. Thionyl chloride (5.59 mL, 76.58 mmol) was added. The reaction was stirred at 78° C. for 2 h. After it was cooled to RT, it was concentrated to remove thinonyl chloride in vacuo. To the residue was added DCM (3 mL) and hexane (20 mL). The mixture was allowed to sit for 20 min before the solvent was decanted to give the residue as crude 3-methoxy-4-nitrophenylphosphonic dichloride. The crude intermediate was added into a 100 mL round-bottomed flask. THF (20 mL) was added to give a brown solution. The solution was cooled to −78° C. in a dry ice/acetone bath. Vinylmagnesium bromide in THF (15.96 mL, 15.96 mmol) was added slowly into the solution over 0.5 h. The reaction was stirred at −78° C. for additional 1 h. NH$_4$Cl (sat'd, 20 mL) was added into the reaction solution at −78° C. and the mixture was allowed to warm up to RT. Water (10 mL) and EtOAc (20 mL) were added. After partition and extraction with EtOAc (2×15 mL), the combined organic layer was dried (Na$_2$SO$_4$) and concentrated to give the crude product. The crude product was added to a silica gel column and eluted with EtOAc/hexane (0-80%). The collected fractions were concentrated to give the product (0.5 g, 26% yield). m/z 254.

Intermediate 59

Diethyl 1-(3-methoxy-4-nitrophenyl)phosphinane-4,4-dicarboxylate 1-oxide

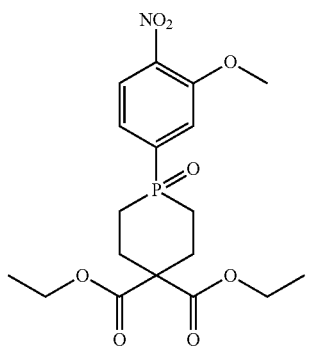 [SMILES: CCOC(=O)C1(C(=O)OCC)CCP(=O)(c2ccc([N+](=O)[O-])c(OC)c2)CC1]

Diethenyl(3-methoxy-4-nitrophenyl)phosphane oxide (INTERMEDIATE 58) (0.45 g, 1.78 mmol) and diethyl malonate (0.285 g, 1.78 mmol) were added to a 15 mL round-bottomed flask. DMSO (10 mL) was added to give a brown solution. Potassium carbonate (0.368 g, 2.67 mmol) was added. The reaction was heated to 75° C. and stirred at that temp for 1 h. The reaction was cooled to RT, and the solution was poured into an HCl solution (1N, 40 mL). The mixture was extracted with EtOAc (3×10 mL), and the combined organic layers were dried (Na$_2$SO$_4$) and concentrated to give the crude product. The crude product was added to a silica gel column (40 g) and eluted with MeOH/DCM (0-5%). The collected fractions were concentrated to give the product (0.3 g, 41%).
$^1$H NMR (300 MHz, DMSO-d6) δ ppm 8.01 (m, 1H), 7.61 (d, 1H), 7.46 (m, 1H), 4.07-4.28 (m, 4H), 4.02 (s, 3H), 2.18-2.42 (m, 5H), 2.11 (m, 3H), 1.10-1.27 (m, 6H).

Intermediate 60

1-(3-methoxy-4-nitrophenyl)phosphinane-4-carboxylic acid 1-oxide

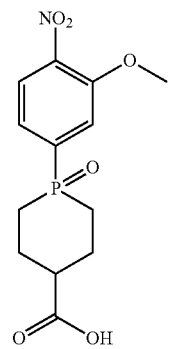 [SMILES: COc1cc(P2(=O)CCC(C(=O)O)CC2)ccc1[N+](=O)[O-]]

Diethyl 1-(3-methoxy-4-nitrophenyl)phosphinane-4,4-dicarboxylate 1-oxide (INTERMEDIATE 59) (4.5 g, 10.89 mmol) and lithium hydroxide (1.043 g, 43.55 mmol) were added to a 200-mL round bottomed flask. Water (30 mL) and THF (30 mL) were added to give a brown suspension. The mixture was heated to 75° C. and stirred at that temperature for 4 h. The reaction mixture was concentrated to give a solid residue. To the mixture was added HCl (aq., 4 N, 60 mL) to give a suspension and further diluted with THF (30.0 mL). The mixture was microwaved at 110° C. for 2 h. After cooling to RT, water (60 mL) was added to the reaction solution. The solution was extracted with 30% iPrOH in chloroform (5×40 mL), and the combined organic layers were concentrated to give the title compound (0.4 g, 12% yield). m/z 314.

Intermediate 61 tert-butyl[1-(3-methoxy-4-nitrophenyl)-1-oxidophosphinan-4-yl]carbamate

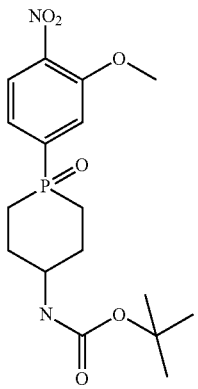 [SMILES: COc1cc(P2(=O)CCC(NC(=O)OC(C)(C)C)CC2)ccc1[N+](=O)[O-]]

To a solution of 1-(3-methoxy-4-nitrophenyl)phosphinane-4-carboxylic acid 1-oxide (INTERMEDIATE 60) (0.42 g, 1.34 mmol) and TEA (0.224 mL, 1.61 mmol) in t-BuOH (10 mL) at 40° C. was added DPPA (0.347 mL, 1.61 mmol) dropwise over 2 min. The resulting solution was stirred at 80° C. for 2 h. The mixture was concentrated in vacuo. The residue was partitioned between EtOAc (15 mL) and NaHCO$_3$/H$_2$O (sat., 15 mL). After partition, the organic layer were collected, concentrated, and purified by silica gel column (10% EtOAc/Hexane) to yield the title compound. m/z 385.

Intermediate 62 propan-2-yl[1-(4-amino-3-methoxyphenyl)-1-oxidonhosphinan-4-yl]carbamate

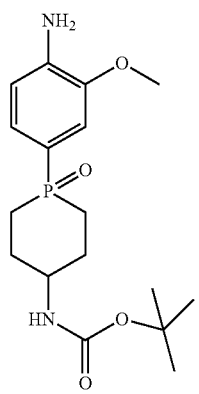 [SMILES: COc1cc(P2(=O)CCC(NC(=O)OC(C)(C)C)CC2)ccc1N]

INTERMEDIATE 62 was prepared from the indicated starting material using a method similar to the one described for the synthesis of INTERMEDIATE 26.

Starting material: tert-butyl[1-(3-methoxy-4-nitrophenyl)-1-oxidophosphinan-4-yl]carbamate (INTERMEDIATE 61). m/z 355.

Intermediate 63A and Intermediate 63B (trans)-(±)-3-fluoro-1-(3-methoxy-4-nitrophenyl)piperidin-4-amine

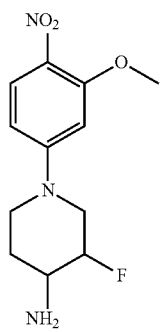 [SMILES: COc1cc(N2CCC(N)C(F)C2)ccc1[N+](=O)[O-]]

4-Fluoro-2-methoxy-1-nitrobenzene (0.856 g, 5 mmol), 3-fluoro-1-(3-methoxy-4-nitrophenyl)piperidin-4-amine (2.322g, 10 mmol), and potassium carbonate (4.15 g, 30.00 mmol) in DMF (25.00 ml) were heated at 80° C. overnight. The solvent was removed by concentration in vacuo. The residue was partitioned between water and CH$_2$Cl$_2$. The concentrated organic phase was loaded onto a silica gel column and purified. Two regioisomers were obtained.

The first regioisomer to elude was the title compound, trans-(±)-3-fluoro-1-(3-methoxy-4-nitrophenyl)piperidin-4-amine (621 mg, 46% yield, INTERMEDIATE 63A)

$^1$H NMR (400 MHz, CHLOROFORM-d) δ ppm 7.95-8.18 (m, 1H), 6.47 (d, 1H), 6.38 (br. s., 1H), 4.28 (m, 1H), 4.08 (m, 1H) 3.98 (s, 3H), 3.83 (m, 1H) 3.06 (m, 2H), 2.09 (m, 1H), 1.55 (m, 2H). m/z 270.

The second regioisomer to elude was cis-3-fluoro-1-(3-methoxy-4-nitrophenyl)piperidin-4-amine (346 mg, 26% yield, INTERMEDIATE 63B).

$^1$H NMR (400 MHz, CHLOROFORM-d) δ ppm 8.02 (d, 1H), 6.47 (m, 1H), 6.38 (d, 1H), 4.75 (m, 1H), 4.16 (m, 1H), 3.98 (s, 3H), 3.89 (m, 1H), 3.26 (m, 1H), 2.94-3.17 (m, 2H) 1.78-1.96 (m, 2H). m/z 270.

Intermediate 64

(trans)-(±)-1-(4-amino-3-methoxyphenyl)-3-fluoropiperidin-4-amine

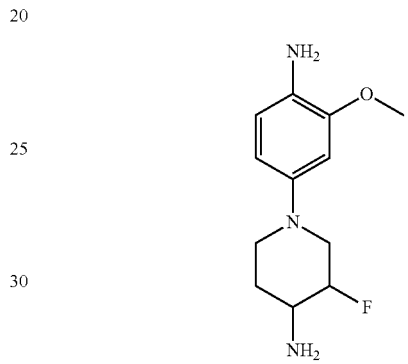

INTERMEDIATE 64 was prepared from the indicated starting material using a method similar to the one described for the synthesis of INTERMEDIATE 26.

Starting material: (trans)-(±)-3-fluoro-1-(3-methoxy-4-nitrophenyl)piperidin-4-amine (INTERMEDIATE 63A). m/z 240.

Intermediate 65

(cis)-(±)-1-(4-amino-3-methoxyphenyl)-3-fluoropiperidin-4-amine

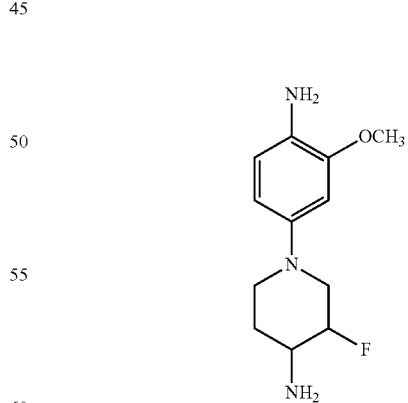

INTERMEDIATE 65 was prepared from the indicated starting material using a method similar to the one described for the synthesis of INTERMEDIATE 26.

Starting material: (cis)-(±)-3-fluoro-1-(3-methoxy-4-nitrophenyl)piperidin-4-amine (INTERMEDIATE 63B). m/z 240.

EXAMPLE 1

N-(4-(4-Aminopiperidin-1-yl)-2-methoxyphenyl)-5-chloro-4-(1H-indol-3-yl)pyrimidin-2-amine as the trifluoroacetic acid salt

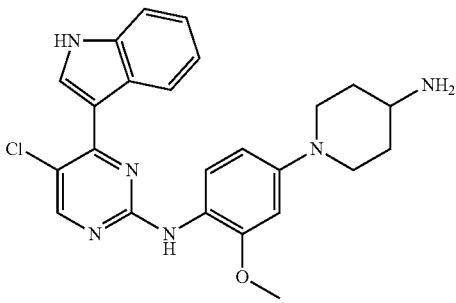 [SMILES: COc1cc(N2CCC(N)CC2)ccc1Nc1ncc(Cl)c(-c2c[nH]c3ccccc23)n1]

Pd/C (10% Degussa Type) (0.083 g) was added to tert-butyl 1-(3-methoxy-4-nitrophenyl)piperidin-4-ylcarbamate (INTERMEDIATE 9, 0.83 g, 2.36 mmol) in (10 mL MeOH/5 mL EtOAc) and the reaction mixture was stirred at RT for 1 h under 1 atm $H_2$. The reaction mixture was filtered through Celite® and concentrated in vacuo. The crude tert-butyl 1-(4-amino-3-methoxyphenyl)piperidin-4-ylcarbamate was taken up in n-pentanol (4.0 mL) then 3-(2,5-dichloropyrimidin-4-yl)-1H-indole (INTERMEDIATE 2, 0.624 g, 2.36 mmol) and PTSA monohydrate (0.90 g, 4.72 mmol) were added. The resultant mixture was heated in a microwave at 160° C. for 1 h. The reaction mixture was concentrated in vacuo and the crude residue was purified by reverse phase HPLC using an Atlantis Prep T3 OBD column to give the title product (0.40 g, 30%).

$^1$H NMR (400 MHz, DMSO-$d_6$) δ ppm 11.85 (d, 1H), 8.44 (s, 1H), 8.35 (br. s., 1H), 8.27 (1H, s), 8.24 (1H, d), 7.96 (3H, m), 7.51 (s, 1H), 7.39 (s, 1H), 7.18-7.06 (m, 1H), 6.95 (t, 1H), 6.75 (br. s., 1H), 6.58 (d, 1H), 3.72 (s, 3H), 3.76-3.65 (m, 2H), 3.20 (d, 1H), 2.89 (t, 2H), 2.02-1.90 (m, 2H), 1.80-1.53 (m, 2H). m/z 449.

EXAMPLES 2 TO 6 were prepared from the indicated starting materials using a method similar to the one described for the synthesis of EXAMPLE 1:

EXAMPLE 2

5-Chloro-4-(1H-indol-3-yl)-N-(2-methoxy-4-(4-(methylamino)piperidin-1-yl)phenyl)pyrimidin-2-amine as the trifluoroacetic acid salt

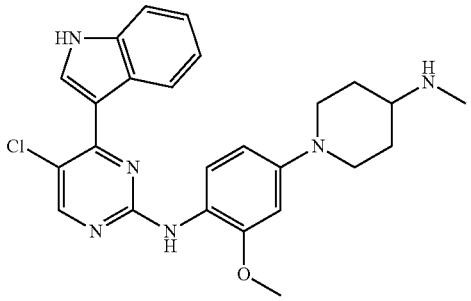 [SMILES: CNC1CCN(c2ccc(Nc3ncc(Cl)c(-c4c[nH]c5ccccc45)n3)c(OC)c2)CC1]

Starting materials: 3-(2,5-dichloropyrimidin-4-yl)-1H-indole (INTERMEDIATE 2) and tert-butyl 1-(3-methoxy-4-nitrophenyl)piperidin-4-yl(methyl)carbamate (INTERMEDIATE 10).

$^1$H NMR (400 MHz, DMSO-$d_6$) δ ppm 11.87 (br. s., 1H), 8.60 (br. s., 2H), 8.49 (d, 1H), 8.35 (br. s., 1H), 8.32 (s, 1H), 8.29 (d, 1H), 7.48 (dd, 2H), 7.24-7.10 (m, 1H), 7.00 (t, 1H), 6.75 (d, 1H), 6.59 (dd, 1H), 3.82 (d, 2H), 3.78 (s, 3H), 3.28-3.07 (m, 1H), 2.82 (t, 2H), 2.62 (t, 3H), 2.10 (d, 2H), 1.66 (m, 2H). m/z 463.

EXAMPLE 3

5-Chloro-4-(1H-indol-3-yl)-N-(2-methoxy-4-(4-(piperazin-1-yl)piperidin-1-yl)phenyl)pyrimidin-2-amine

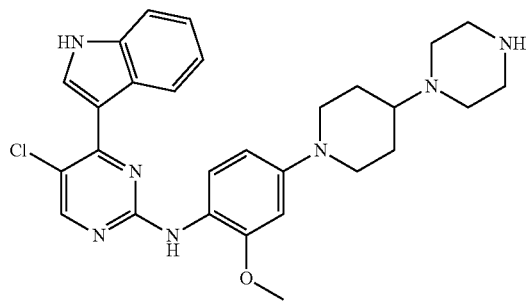 [SMILES: COc1cc(N2CCC(N3CCNCC3)CC2)ccc1Nc1ncc(Cl)c(-c2c[nH]c3ccccc23)n1]

Starting materials: 3-(2,5-dichloropyrimidin-4-yl)-1H-indole (INTERMEDIATE 2) and tert-butyl 4-(1-(3-methoxy-4-nitrophenyl)piperidin-4-yl)piperazine-1-carboxylate (INTERMEDIATE 8).

$^1$H NMR (400 MHz, DMSO-$d_6$) δ ppm 11.82 (br. s., 1H), 8.46 (s, 1H), 8.30 (s, 1H), 8.25 (s, 2H), 7.43 (dd, 2H), 7.19-7.12 (m, 1H), 6.97 (s, 1H), 6.66 (d, 1H), 6.50 (dd, 1H), 3.75 (s, 3H), 3.75-3.72 (m, 2H), 2.79-2.62 (m, 7H), 2.46 (d, 4H), 2.36-2.22 (m, 1H), 1.85 (d, 2H), 1.65-1.42 (m, 2H). m/z 519.

EXAMPLE 4

4-(1H-Indol-3-yl)-N-(2-methoxy-4-(4-(methylamino)piperidin-1-yl)phenyl)-5-methylpyrimidin-2-amine

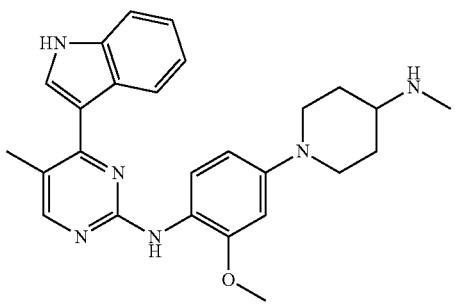

Starting materials: 3-(2-chloro-5-methylpyrimidin-4-yl)-1H-indole (INTERMEDIATE 1) and tert-butyl 1-(3-methoxy-4-nitrophenyl)piperidin-4-yl(methyl)carbamate (INTERMEDIATE 10).

¹H NMR (400 MHz, DMSO-d₆) δ ppm 12.36 (br. s., 1H), 9.98-9.55 (1H, m), 8.71 (br. s., 2H.), 8.40 (m, 2H), 8.08 (br. s., 1H), 7.51 (d, 1H), 7.36 (d, 1H), 7.24 (t, 1H), 7.06 (br. s., 1H), 6.78 (d, 1H), 6.64 (dd, 1H), 3.90 (d, 2H), 3.78 (s, 3H), 3.32-3.06 (m, 1H), 2.82 (t, 2H), 2.63 (t, 3H), 2.11 (d, 2H), 1.73-1.54 (m, 2H). m/z 443.

EXAMPLE 5

N-(4-(4-Aminopiperidin-1-yl)-2-methoxyphenyl)-4-(1H-indol-3-yl)-5-methylpyrimidin-2-amine as the trifluoroacetic acid salt

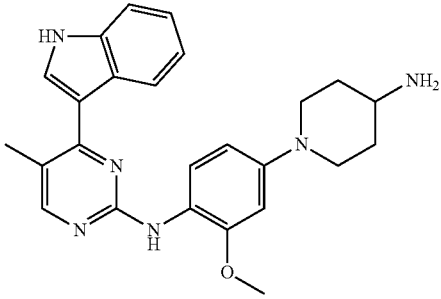 [SMILES: COc1cc(N2CCC(N)CC2)ccc1Nc1ncc(C)c(-c2c[nH]c3ccccc23)n1]

Starting materials: 3-(2-chloro-5-methylpyrimidin-4-yl)-1H-indole (INTERMEDIATE 1) and tert-butyl 1-(3-methoxy-4-nitrophenyl)piperidin-4-ylcarbamate (INTERMEDIATE 9).

¹H NMR (400 MHz, DMSO-d₆) δ ppm 8.31 (s, 1H), 8.09-7.96 (m, 1H), 7.88 (s, 1H), 7.51-7.46 (m, 1H), 7.43 (d, 1H), 7.23 (t, 1H), 6.99 (t, 1H), 6.93 (d, 1H), 6.83 (dd, 1H), 3.79-3.74 (m, 2H), 3.73 (s, 3H), 3.43-3.24 (m, 1H), 3.20-3.04 (m, 2H), 2.35 (s, 3H), 2.18-2.04 (m, 2H), 1.87-1.70 (m, 2H). m/z 429.

EXAMPLE 6

5-Chloro-N-(4-(4-(cyclopropylamino)piperidin-1-yl)-2-methoxyphenyl)-4-(1H-indol-3-yl)pyrimidin-2-amine as the trifluoroacetic acid salt

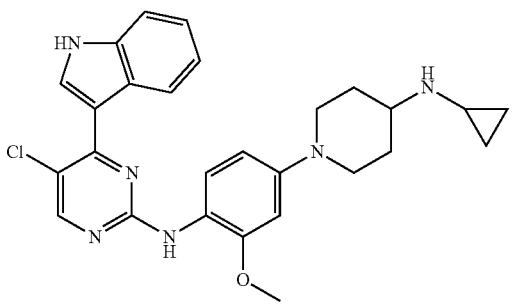 [SMILES: COc1cc(N2CCC(NC3CC3)CC2)ccc1Nc1ncc(Cl)c(-c2c[nH]c3ccccc23)n1]

Starting materials: 3-(2,5-dichloropyrimidin-4-yl)-1H-indole (INTERMEDIATE 2) and N-cyclopropyl-1-(3-methoxy-4-nitrophenyl)piperidin-4-amine (INTERMEDIATE 19).

¹H NMR (400 MHz, DMSO-d₆) δ ppm 11.85 (d, 1H), 8.73 (br. s., 2H), 8.48 (d, 1H), 8.36-8.21 (m, 3H), 7.47 (dd, 2H), 7.22-7.09 (m, 1H), 6.99 (t, 1H), 6.73 (d, 1H), 6.64-6.47 (m, 1H), 3.84 (d, 2H), 3.78 (s, 3H), 3.38 (m, 1H), 2.94-2.70 (m, 3H), 2.14 (d, 2H), 1.83-1.54 (m, 2H), 0.89-0.67 (m, 4H). m/z 490.

EXAMPLE 7

5-Fluoro-4-(1H-Indol-3-yl)-N-(2-methoxy-4-(4-(4-methylpiperazin-1-yl)piperidin-1-yl)phenyl)pyrimidin-2-amine as the trifluoroacetic acid salt

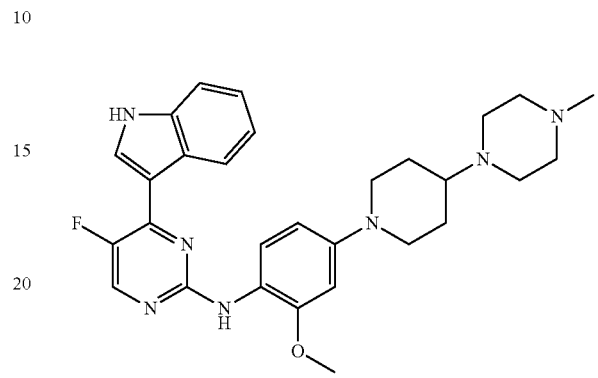

3-(2-Chloro-5-fluoropyrimidin-4-yl)-1H-indole (INTERMEDIATE 3, 0.164 g, 0.66 mmol), 2-methoxy-4-(4-(4-methylpiperazin-1-yl)piperidin-1-yl)aniline (INTERMEDIATE 27, 0.25 g, 0.66 mmol) and PTSA monohydrate (0.252 g, 1.33 mmol) in n-pentanol (4 mL) were heated in a microwave at 160° C. for 1 h. The reaction mixture was concentrated in vacuo and the crude residue was purified by reverse phase HPLC using an Atlantis Prep T3 OBD column to give the title product (31 mg, 9.1%).

¹H NMR (400 MHz, METHANOL-d₄) δ ppm 8.55 (d, 1H), 8.35-8.20 (m, 3H), 7.53 (d, 1H), 7.29 (m, 1H), 7.18-7.24 (m, 1H), 7.17 (br. s., 1H), 7.09 (d, 1H), 4.01 (s, 3H), 3.87 (d, 2H), 3.43-3.57 (m, 3H), 3.26-3.40 (m, 4H), 3.01-3.13 (m, 4H), 2.92 (s, 3H), 2.24 (d, 2H), 1.94-2.11 (m, 2H). m/z 516.

EXAMPLES 8 to 32 were prepared from the indicated starting materials using a method similar to the one described for the synthesis of EXAMPLE 7:

EXAMPLE 8

4-(1H-Indol-3-yl)-N-(2-methoxy-4-(4-(4-methylpiperazin-1-yl)piperidin-1-yl)phenyl)-5-(trifluoromethyl)pyrimidin-2-amine

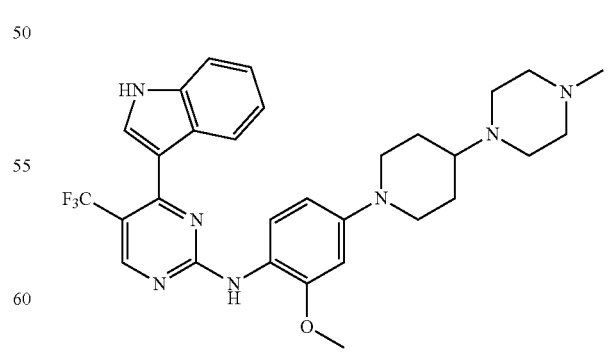

Starting materials: 3-(2-chloro-5-(trifluoromethyl)pyrimidin-4-yl)-1H-indole (INTERMEDIATE 4) and 2-methoxy-4-(4-(4-methylpiperazin-1-yl)piperidin-1-yl)aniline (INTERMEDIATE 27).

¹H NMR (300 MHz, CD₃OD) δ ppm 8.57 (s, 1H), 8.31 (d, 1H), 8.08 (d, 1H), 7.79 (s, 1H), 7.38 (d, 1H), 7.13 (t, 1H), 7.04-6.99 (m, 2H), 6.87 (br. s., 1H), 3.89 (s, 3H), 3.72-3.68 (m, 2H), 3.33-3.25 (m, 4H), 2.97-2.79 (m, 9H), 2.11-2.07 (m, 2H), 1.90-1.87 (m, 2H). m/z 566.

EXAMPLE 9

4-(1H-Indol-3-yl)-N-(2-methoxy-4-(4-(4-methylpiperazin-1-yl)piperidin-1-yl)phenyl)-5-methylpyrimidin-2-amine

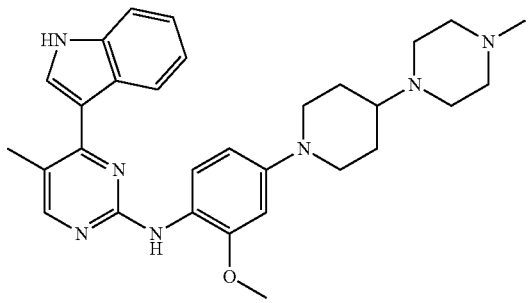

Starting materials: 3-(2-chloro-5-methylpyrimidin-4-yl)-1H-indole (INTERMEDIATE 1) and 2-methoxy-4-(4-(4-methylpiperazin-1-yl)piperidin-1-yl)aniline (INTERMEDIATE 27).

¹H NMR (400 MHz, METHANOL-d₄) δ ppm 8.32 (d, 1H), 8.18 (s, 1H), 8.13 (d, 1H), 7.86 (s, 1H), 7.47 (d, 1H), 7.22 (td, 1H), 7.04-7.14 (m, 1H), 6.73 (d, 1H), 6.58 (dd, 1H), 3.92 (s, 3H), 3.71 (d, 2H), 2.66-2.80 (m, 5H), 2.57 (m, 4H), 2.41 (s, 3H), 2.35-2.40 (m, 2H), 2.33 (s, 3H), 2.03 (d, 2H), 1.69 (m, 2H). m/z 512.

EXAMPLE 10

5-Chloro-4-(1H-indol-3-yl)-N-(2-methoxy-4-(4-(4-methylpiperazin-1-yl)piperidin-1-yl)phenyl)pyrimidin-2-amine

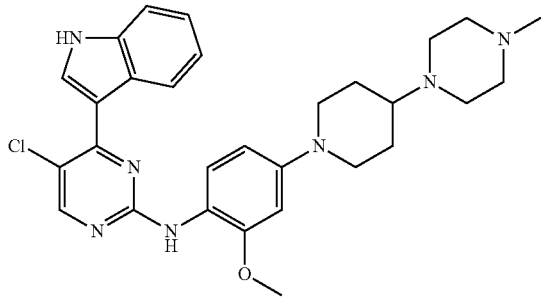 [SMILES: COc1cc(N2CCC(N3CCN(C)CC3)CC2)ccc1Nc1ncc(Cl)c(-c2c[nH]c3ccccc23)n1]

Starting materials: 3-(2,5-dichloropyrimidin-4-yl)-1H-indole (INTERMEDIATE 2) and 2-methoxy-4-(4-(4-methylpiperazin-1-yl)piperidin-1-yl)aniline (INTERMEDIATE 27).

¹H NMR (400 MHz, DICHLOROMETHANE-d₂) δ ppm 8.79 (br. s., 1H), 8.50 (d, 1H), 8.38 (d, 1H), 8.33 (s, 1H), 8.14 (d, 1H), 7.48 (d, 1H), 7.38 (s, 1H), 7.35-727 (m, 1H), 7.26-7.15 (m, 1H), 6.59 (d, 1H), 6.52 (dd, 1H), 3.90 (s, 3H), 3.67 (d, 2H), 2.79-2.67 (m, 2H), 2.60 (br. s., 4H), 2.51-2.28 (m, 5H), 2.23 (s, 3H), 1.93 (d, 2H), 1.66 (m, 2H). m/z 533.

EXAMPLE 11

N-(4-(4-(Dimethylamino)piperidin-1-yl)-2-methoxyphenyl)-4-(1H-indol-3-yl)-5-methylpyrimidin-2-amine

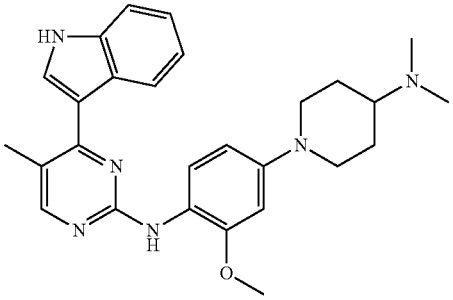

Starting materials: 3-(2-chloro-5-methylpyrimidin-4-yl)-1H-indole (INTERMEDIATE 1) and 1-(4-amino-3-methoxyphenyl)-N,N-dimethylpiperidin-4-amine (INTERMEDIATE 28).

¹H NMR (400 MHz, DMSO-d₆) δ ppm 8.27 (d, 1H), 8.11 (s, 1H), 7.89 (s, 1H), 7.73 (d, 1H), 7.57 (s, 1H), 7.38 (d, 1H), 7.03-7.14 (m, 1H), 6.86-7.00 (m, 1H), 6.57-6.57 (m, 1H), 6.62-6.55 (m, 1H), 6.40 (dd, 1H), 3.74 (s, 3H), 3.65-3.55 (m, 2H), 2.65-2.51 (m, 2H), 2.27 (s, 3H), 2.18-2.07 (m, 7H), 1.78 (d, 2H), 1.44 (m, 2H). m/z 457.

EXAMPLE 12

5-Chloro-N-(4-(4-(dimethylamino)piperidin-1-yl)-2-methoxyphenyl)-4-(1H-indol-3-yl)pyrimidin-2-amine

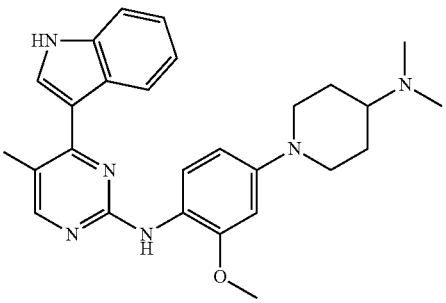

Starting materials: 3-(2,5-dichloropyrimidin-4-yl)-1H-indole (INTERMEDIATE 2) and 1-(4-amino-3-methoxyphenyl)-N,N-dimethylpiperidin-4-amine (INTERMEDIATE 28).

¹H NMR (300 MHz, DMSO-d₆) δ ppm 11.81 (s, 1H), 8.46 (d, 1H), 8.31-8.24 (m, 3H), 7.46-7.42 (m, 2H), 7.16 (t, 1H), 6.98 (t, 1H), 6.66 (d, 1H), 6.51 (1H, dd), 3.76 (s, 3H), 3.71(br. s., 1H), 2.70 (t, 2H), 2.22 (s, 8H), 1.88-1.84 (m, 2H), 1.57-1.46 (m, 2H). m/z 477.

EXAMPLE 13

N-(4-(4-(Dimethylamino)piperidin-1-yl)-2-methoxyphenyl)-5-fluoro-4-(1H-indol-3-yl)pyrimidin-2-amine

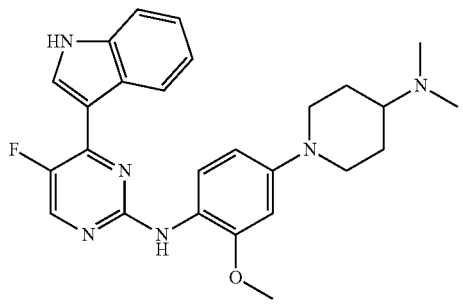 [SMILES: COc1cc(N2CCC(N(C)C)CC2)ccc1Nc1ncc(F)c(-c2c[nH]c3ccccc23)n1]

Starting materials: 3-(2-chloro-5-fluoropyrimidin-4-yl)-1H-indole (INTERMEDIATE 3) and 1-(4-amino-3-methoxyphenyl)-N,N-dimethylpiperidin-4-amine (INTERMEDIATE 28).

$^1$H NMR (300 MHz, DMSO-$d_6$) 11.81 (s, 1H), 9.40 (br. s., 1H), 8.35 (d, 1H), 8.22 (d, 1H), 8.03 (d, 2H), 7.52 (d, 1H), 7.41 (d, 1H), 7.13 (t, 1H), 6.98 (t, 1H), 6.64 (s, 1H), 6.51 (dd, 1H), 3.82-3.78 (m, 2H), 3.72 (s, 3H), 2.73-2.63 (m, 8H), 2.20 (br. s., 1H), 2.05-2.01 (m, 2H), 1.69-1.66 (m, 2H). m/z 461.

EXAMPLE 14

5-Chloro-4-(1H-indol-3-yl)-N-(2-methoxy-5-methyl-4-(4-(4-methylpiperazin-1-yl)piperidin-1-yl)phenyl)pyrimidin-2-amine

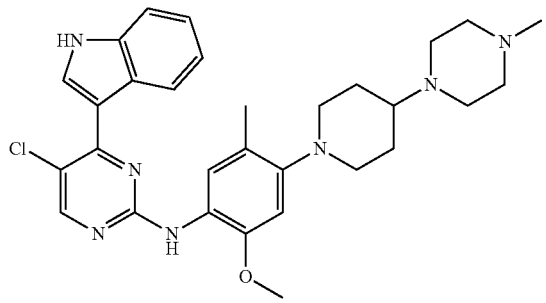 [SMILES: COc1cc(N2CCC(N3CCN(C)CC3)CC2)c(C)cc1Nc1ncc(Cl)c(-c2c[nH]c3ccccc23)n1]

Starting materials: 3-(2,5-dichloropyrimidin-4-yl)-1H-indole (INTERMEDIATE 2) and 2-methoxy-5-methyl-4-(4-(4-methylpiperazin-1-yl)piperidin-1-yl)aniline (INTERMEDIATE 26).

$^1$H NMR (300 MHz, DMSO-$d_6$) δ ppm 11.91 (s, 1H), 8.53 (d, 1H), 8.41 (s, 1H), 8.35 (d, 1H), 8.27 (s, 1H), 8.22 (s, 1H), 7.63 (s, 1H), 7.56-7.50 (m, 1H), 7.28-7.14 (m, 1H), 7.05 (t, 1H), 6.80 (s, 1H), 3.83 (s, 3H), 3.19 (d, 2H), 2.78-2.62 (m, 6H), 2.54-2.38 (m, 5H), 2.35 (s, 1H), 2.30 (s, 3H), 2.22 (s, 3H), 1.95 (d, 2H), 1.75-1.58 (m, 2H). m/z 547.

EXAMPLE 15

4-(1H-Indol-3-yl)-N-(2-methoxy-5-methyl-4-(4-(4-methylpiperazin-1-yl)piperidin-1-yl)phenyl)-5-methylpyrimidin-2-amine

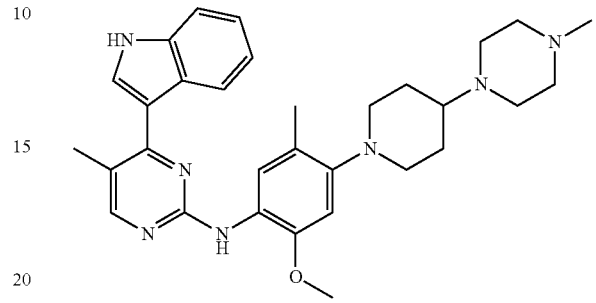

Starting materials: 3-(2-chloro-5-methylpyrimidin-4-yl)-1H-indole (INTERMEDIATE 1) and 2-methoxy-5-methyl-4-(4-(4-methylpiperazin-1-yl)piperidin-1-yl)aniline (INTERMEDIATE 26).

$^1$H NMR (400 MHz, DMSO-$d_6$) δ ppm 11.72 (br. s., 1H), 8.39 (d, 1H), 8.23 (s, 1H), 8.07-7.90 (m, 2H), 7.64 (s, 1H), 7.47 (d, 1H), 7.25-7.13 (m, 1H), 7.05 (t, 1H), 6.74 (s, 1H), 3.83 (s, 3H), 3.09 (d, 2H), 2.64 (t, 2H), 2.53 (m, 2H), 2.42 (m, 2H), 2.43-2.24 (m, 8H), 2.15 (d, 6H), 1.86 (d, 2H), 1.70-1.46 (m, 2H). m/z 526.

EXAMPLE 16

5-Chloro-N-(4-(4-(dimethylamino)piperidin-1-yl)-2-methoxy-5-methylphenyl)-4-(1H-indol-3-yl)pyrimidin-2-amine

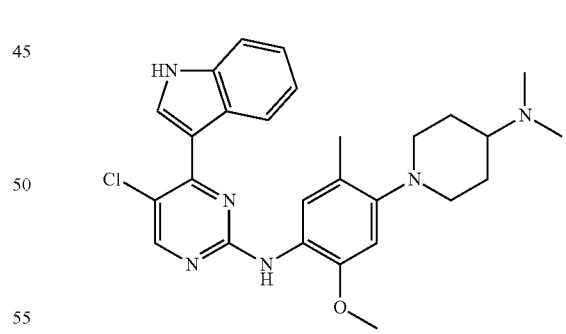

Starting materials: 3-(2,5-dichloropyrimidin-4-yl)-1H-indole (INTERMEDIATE 2) and 1-(4-amino-5-methoxy-2-methylphenyl)-N,N-dimethylpiperidin-4-amine (INTERMEDIATE 30).

$^1$H NMR (300 MHz, DMSO-$d_6$) δ ppm 11.85 (s, 1H), 8.48 (s, 1H), 8.35 (s, 1H), 8.30 (d, 1H), 8.21 (s, 1H), 7.57 (s, 1H), 7.47 (d, 1H), 7.19 (t, 1H), 7.04-6.95 (m, 1H), 6.75 (s, 1H), 3.77 (s, 3H), 3.31 (s, 6H), 3.13 (d, 2H), 2.67 (t, 2H), 2.23 (s, 6H), 2.17 (s, 3H), 1.87 (d, 2H), 1.57 (dd, 2H). m/z 491.

EXAMPLE 17

N-(4-(4-(Dimethylamino)piperidin-1-yl)-2-methoxy-5-methylphenyl)-4-(1H-indol-3-yl)-5-methylpyrimidin-2-amine

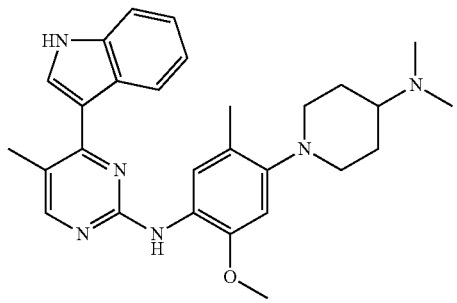

Starting materials: 3-(2-chloro-5-methylpyrimidin-4-yl)-1H-indole (INTERMEDIATE 1) and 1-(4-amino-5-methoxy-2-methylphenyl)-N,N-dimethylpiperidin-4-amine (INTERMEDIATE 30).

$^1$H NMR (400 MHz, DMSO-d$_6$) δ ppm 11.74 (br. s., 1H), 8.42 (d, 1H), 8.26 (s, 1H), 8.07 (s, 1H), 8.00 (d, 1H), 7.68 (s, 1H), 7.48 (d, 1H), 7.13-7.33 (m, 1H), 7.13-6.97 (m, 1H) 6.86 (s, 1H) 3.86 (s, 3H) 2.94 (br. s., 2H) 2.76 (br. s., 1H) 2.72-2.59 (m, 1H), 2.38 (s, 3H), 2.37-2.24 (m, 1H), 2.23-2.14 (m, 3H), 1.71 (br. s., 4H), 1.04 (d, 6H). m/z 471.

EXAMPLE 18

N-(4-(4-Aminopiperidin-1-yl)-2-methoxy-5-methylphenyl)-5-chloro-4-(1H-indol-3-yl)pyrimidin-2-amine

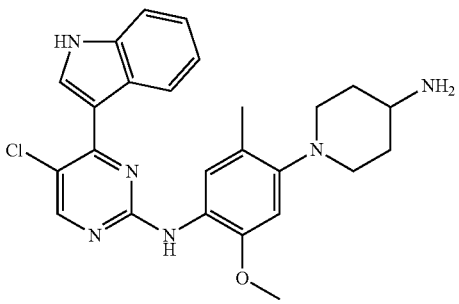 [SMILES: COc1cc(N2CCC(N)CC2)c(C)cc1Nc1ncc(Cl)c(-c2c[nH]c3ccccc23)n1]

Starting materials: 3-(2,5-dichloropyrimidin-4-yl)-1H-indole (INTERMEDIATE 2) tert-butyl 1-(4-amino-5-methoxy-2-methylphenyl)piperidin-4-ylcarbamate (INTERMEDIATE 29).

$^1$H NMR (400 MHz, DMSO-d$_6$) δ ppm 11.86 (br. s., 1H), 8.56-8.42 (m, 1H), 8.39-8.34 (m, 1H), 8.30 (d, 1H), 8.22 (s, 1H), 7.52-7.63 (m, 1H), 7.47 (d, 1H), 7.26-7.09 (m, 1H), 7.00 (t, 1H), 6.76 (s, 1H), 3.11-2.99 (m, 2H), 2.78-2.62 (m, 3H), 2.22-2.13 (m, 3H), 1.84 (d, 2H), 1.60 (br. s., 2H), 1.52-1.32 (m, 2H). m/z 463.

EXAMPLE 19

N-(4-(4-aminopiperidin-1-yl)-2-methoxy-5-methylphenyl)-4-(1H-indol-3-yl)-5-methylpyrimidin-2-amine

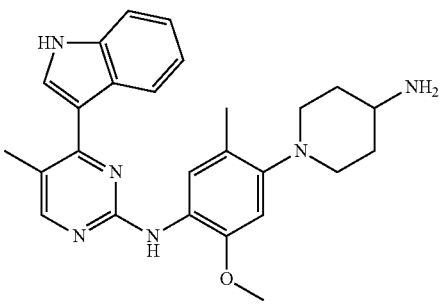 [SMILES: COc1cc(N2CCC(N)CC2)c(C)cc1Nc1ncc(C)c(-c2c[nH]c3ccccc23)n1]

Starting materials: 3-(2-chloro-5-methylpyrimidin-4-yl)-1H-indole (INTERMEDIATE 1) tert-butyl 1-(4-amino-5-methoxy-2-methylphenyl)piperidin-4-ylcarbamate (INTERMEDIATE 29).

$^1$H NMR (400 MHz, DMSO-d$_6$) δ ppm 11.72 (br. s., 1H), 8.40 (d, 1H), 8.23 (s, 1H), 7.99 (d, 2H), 7.64 (s, 1H), 7.47 (d, 1H), 7.19 (td, 1H), 7.13-6.99 (m, 1H), 6.75 (s, 1H), 3.83 (s, 3H), 3.01 (d, 2H), 2.76-2.55 (m, 3H), 2.43-2.26 (m, 3H), 2.15 (s, 3H), 1.82 (d, 2H), 1.70 (br. s., 2H), 1.54-1.26 (m, 2H). m/z 443.

EXAMPLE 20

2-(1-(4-(5-Chloro-4-(1H-indol-3-yl)pyrimidin-2-ylamino)-3-methoxyphenyl)piperidin-4-ylamino)ethanol

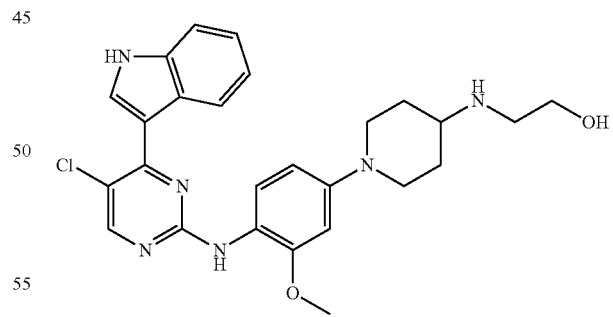

Starting materials: 3-(2,5-dichloropyrimidin-4-yl)-1H-indole (INTERMEDIATE 2) 2-(1-(4-amino-3-methoxyphenyl)piperidin-4-ylamino)ethanol (INTERMEDIATE 31).

$^1$H NMR (300 MHz, DMSO-d$_6$) δ ppm 11.71 (br. s., 1H), 8.45-8.41 (m, 2H), 8.25-8.21 (m, 2H), 7.41 (dd, 2H), 7.10 (t, 1H), 6.93 (t, 1H), 6.66 (s, 1H), 6.50 (dd, 1H), 3.74-3.60 (m, 9H), 3.19 (br. s., 1H), 3.00 (br. s., 2H), 2.70 (t, 2H), 2.07-2.04 (m, 2H), 1.66-1.63 (m, 2H). m/z 493.

EXAMPLE 21

5-Chloro-4-(1H-indol-3-yl)-N-(2-methoxy-4-{4-[4-(methylsulfonyl)piperazin-1-yl]piperidin-1-yl}phenyl)pyrimidin-2-amine as the trifluoroacetic acid salt

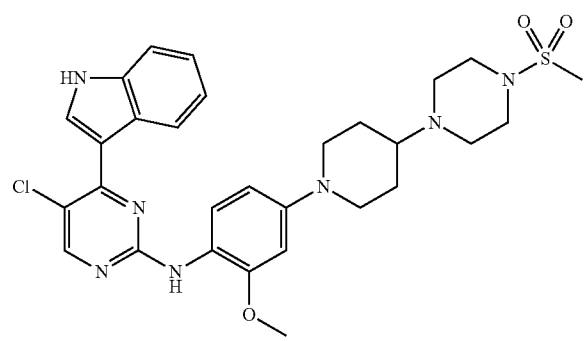 [SMILES: COc1cc(N2CCC(N3CCN(S(C)(=O)=O)CC3)CC2)ccc1Nc1ncc(Cl)c(-c2c[nH]c3ccccc23)n1]

Starting materials: 3-(2,5-dichloropyrimidin-4-yl)-1H-indole (INTERMEDIATE 2) and 2-methoxy-4-(4-(4-(methylsulfonyl)piperazin-1-yl)piperidin-1-yl)aniline (INTERMEDIATE 32).

$^1$H NMR (300 MHz, DMSO-$d_6$) δ ppm 11.87 (s, 1H), 9.79 (s, 1H), 8.49 (d, 1H), 8.39-8.17 (m, 3H), 7.54-7.42 (m, 2H), 7.24-7.05 (m, 2H), 7.00 (t, 1H), 6.74 (s, 1H), 6.59 (d, 1H), 3.79 (s, 3H), 3.74-3.60 (m, 3H), 3.50 (t, 2H), 3.34-3.11 (m, 4H), 3.05 (s, 3H), 2.78 (t, 2H), 2.16 (d, 2H), 1.79 (m, 2H). m/z 596.

EXAMPLE 22

5-Chloro-N-(4-{4-[(3R)-3-fluoropyrrolidin-1-yl]piperidin-1-yl}-2-methoxyphenyl)-4-(1H-indol-3-yl)pyrimidin-2-amine as the trifluoroacetic acid salt

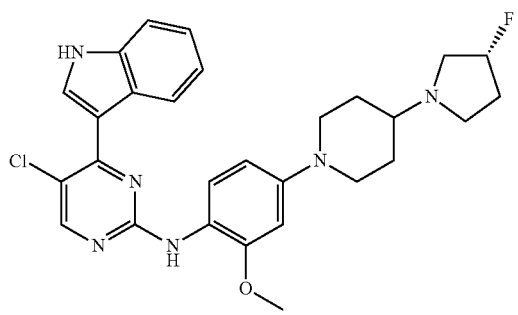 [SMILES: COc1cc(N2CCC(N3CC[C@@H](F)C3)CC2)ccc1Nc1ncc(Cl)c(-c2c[nH]c3ccccc23)n1]

Starting materials: 3-(2,5-dichloropyrimidin-4-yl)-1H-indole (INTERMEDIATE 2) and (R)-4-(4-(3-fluoropyrrolidin-1-yl)piperidin-1-yl)-2-methoxyaniline (INTERMEDIATE 33).

$^1$H NMR (300 MHz, DMSO-$d_6$) δ ppm 11.87 (s, 1H), 10.28 (s, 1H), 8.49 (d, 1H), 8.43-8.23 (m, 3H), 7.48 (t, 2H), 7.17 (t, 1H), 7.05-6.93 (m, 1H), 6.75 (br. s., 1H), 6.59 (d,1H), 5.67-5.51 (m, 1H), 3.94-3.58 (m, 8H), 3.37 (s, 2H), 2.87-2.67 (m, 2H), 2.40 (d, 1H), 2.17 (s, 3H),1.92-1.59 (m, 2H). m/z 521.

EXAMPLE 23

5-Chloro-4-(1H-indol-3-yl)-N-(4-(4-(4-isopropylpiperazin-1-yl)piperidin-1-yl)-2-methoxyphenyl)pyrimidin-2-amine as the trifluoroacetic acid salt

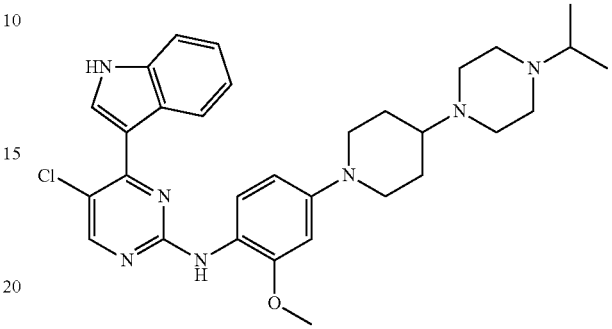

Starting materials: 3-(2,5-dichloropyrimidin-4-yl)-1H-indole (INTERMEDIATE 2) and 4-(4-(4-isopropylpiperazin-1-yl)piperidin-1-yl)-2-methoxyaniline (INTERMEDIATE 34).

$^1$H NMR (300 MHz, DMSO-$d_6$) δ ppm 11.88 (s, 1H), 8.50 (d, 1H), 8.44-8.20 (m, 3H), 7.64-7.37 (m, 3H), 7.24-7.07 (m, 2H), 7.01 (t, 1H), 6.82 (s, 1H), 6.66 (d, 1H), 3.88 (d, 2H), 3.80 (s, 3H), 3.74-3.45 (m, 5H), 3.41-3.01 (m, 5H), 2.97-2.76 (m, 2H), 2.13 (m, 2H), 1.78 (m, 2H), 1.27 (d, 6H). m/z 560.

EXAMPLE 24

5-Chloro-N-(4-(4-((2S,6R)-2,6-dimethylmorpholino)piperidin-1-yl)-2-methoxyphenyl)-4-(1H-indol-3-yl)pyrimidin-2-amine as the trifluoroacetic acid salt

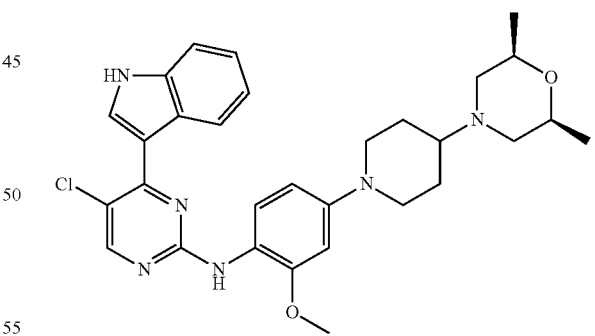

Starting materials: 3-(2,5-dichloropyrimidin-4-yl)-1H-indole (INTERMEDIATE 2) and 4-(4-((2S,6R)-2,6-dimethylmorpholino)piperidin-1-yl)-2-methoxyaniline (INTERMEDIATE 35).

$^1$H NMR (300 MHz, DMSO-$d_6$) δ ppm 11.85 (br. s., 1H), 8.48 (d, 1H), 8.36 (s, 1H), 8.30 (d, 1H), 8.22 (s, 1H), 7.58 (s, 1H), 7.47 (d, 1H), 7.12-7.23 (m, 1H), 7.00 (t, 1H), 6.75 (s, 1H), 5.07-5.37 (m, 1H), 3.78 (s, 3H), 3.09 (d, 2H), 2.80-2.98 (m, 2H), 2.61-2.78 (m, 3H), 2.42 (m, 1H), 2.14-2.20 (m, 4H), 2.02-2.13 (m, 1H), 1.89-2.01 (m, 3H), 1.59 (d, 2H). m/z 547.

EXAMPLE 25

(R)-5-Chloro-N-(4-(4-(3-fluoropyrrolidin-1-yl)piperidin-1-yl)-2-methoxy-5-methylphenyl)-4-(1H-indol-3-yl)pyrimidin-2-amine

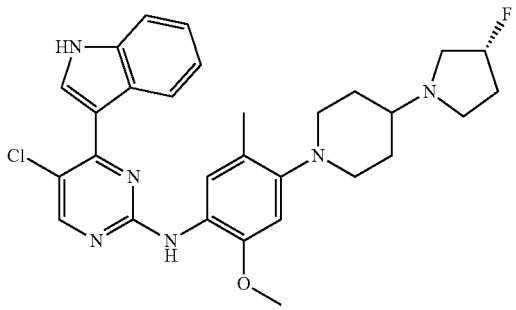 [SMILES: COc1cc(N2CCC(N3CC[C@@H](F)C3)CC2)c(C)cc1Nc1ncc(Cl)c(-c2c[nH]c3ccccc23)n1]

Starting materials: 3-(2,5-dichloropyrimidin-4-yl)-1H-indole (INTERMEDIATE 2) and (R)-4-(4-(3-fluoropyrrolidin-1-yl)piperidin-1-yl)-2-methoxy-5-methylaniline (INTERMEDIATE 36).

$^1$H NMR (300 MHz, DMSO-$d_6$) δ ppm 11.85 (s, 1H), 8.48 (d, 1H), 8.36 (s, 1H), 8.30 (d, 1H), 8.22 (s, 1H), 7.58 (s, 1H), 7.47 (d, 1H), 7.23-7.14 (m, 1H), 7.00 (t, 1H), 6.75 (s, 1H), 3.78 (s, 3H), 3.31 (s, 5H), 3.09 (d, 2H), 2.98-2.61 (m, 5H), 2.42 (d, 1H), 2.24-2.13 (m, 5H), 1.89-2.03 (m, 3H), 1.59 (d, 2H). m/z 535.

EXAMPLE 26

5-Chloro-4-(1H-indol-3-yl)-N-(2-methoxy-4-(4-(oxetan-3-ylamino)piperidin-1-yl)phenyl)pyrimidin-2-amine as the trifluoroacetic acid salt

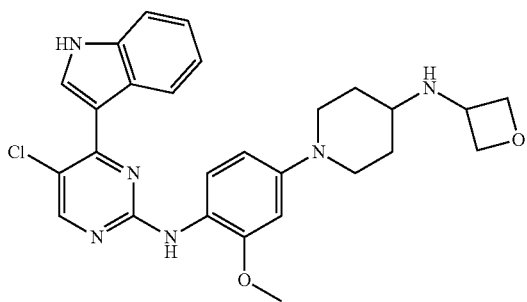 [SMILES: COc1cc(N2CCC(NC3COC3)CC2)ccc1Nc1ncc(Cl)c(-c2c[nH]c3ccccc23)n1]

N-(4-(4-aminopiperidin-1-yl)-2-methoxyphenyl)-5-chloro-4-(1H-indol-3-yl)pyrimidin-2-amine (EXAMPLE 1, 0.13 g, 0.29 mmol), oxetan-3-one (0.042 g, 0.58 mmol) and sodium triacetoxyborohydride (0.123 g, 0.58 mmol) were stirred at 40° C. for 4 h. The reaction mixture was concentrated in vacuo and the crude residue was purified by reverse phase HPLC using an Atlantis Prep T3 OBD column to give the title product (26 mg, 17.8%).

$^1$H NMR (400 MHz, DMSO-$d_6$) δ ppm 11.88 (br. s., 1H), 9.45 (br. s., 1H), 8.49 (d, 1H), 8.36 (br. s., 1H), 8.32 (s, 1H), 8.29 (d, 1H), 7.48 (dd, 2H), 7.23-7.11 (m, 1H), 6.99 (t, 1H), 6.74 (d, 1H), 6.57 (dd, 1H), 4.84-4.74 (m, 2H), 4.70-4.62 (m, 2H), 4.58 (m, 1H), 3.78 (s, 3H), 3.89-3.66 (m, 2H), 3.28 (br. s., 1H), 2.79 (t, 2H), 1.99 (m, 2H), 1.52-1.73 (m, 2H). m/z 506.

EXAMPLE 27

(5-Bromo-4-(1H-indol-3-yl)-N-(2-methoxy-4-(4-(4-methylpiperazin-1-yl)piperidin-1-yl)phenyl)pyrimidin-2-amine

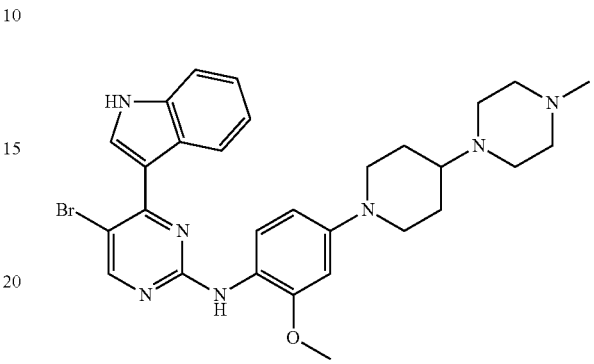

5-Bromo-N-(2-methoxy-4-(4-(4-methylpiperazin-1-yl)piperidin-1-yl)phenyl)-4-(1-tosyl-1H-indol-3-yl)pyrimidin-2-amine (INTERMEDIATE 37, 150 mg, 0.21 mmol) and Cs$_2$CO$_3$ (134 mg, 0.41 mmol) in 1:1 MeOH/THF (2.0 mL) was stirred at reflux for 2 h. The reaction mixture was filtered and concentrated in vacuo. The crude residue was purified by chromatography on silica gel (MeOH/1% NH$_4$OH in DCM) to give the title product (131 mg, 69.5%).

$^1$H NMR (400 MHz, METHANOL-$d_4$) δ ppm 8.62 (s, 1H), 8.54 (s, 1H), 8.43 (s, 1H), 8.34 (d, 1H), 7.51 (d, 1H), 7.30-7.23 (m, 1H), 7.21 (d, 1H), 7.19-7.11 (m, 1H), 7.09 (d, 1H), 4.04 (s, 3H), 3.85 (d, 3H), 3.56 (d, 3H), 3.47-3.35 (m, 4H), 2.93 (s, 6H), 2.24 (br. s., 2H), 2.07 (m, 2H). m/z 578.

EXAMPLE 28

4-(1H-Indol-3-yl)-2-(2-methoxy-4-(4-(4-methylpiperazin-1-yl)piperidin-1-yl)phenylamino)pyrimidine-5-carbonitrile

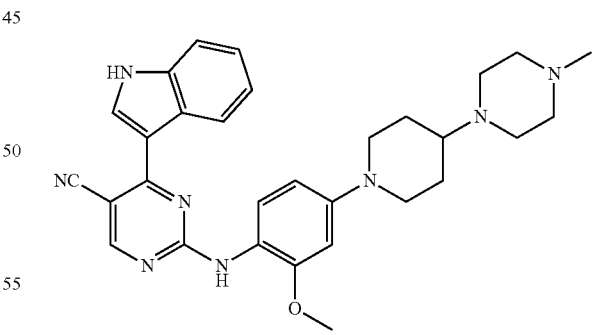

5-Bromo-4-(1H-indol-3-yl)-N-(2-methoxy-4-(4-(4-methylpiperazin-1-yl)piperidin-1-yl)phenyl)pyrimidin-2-amine (Example 27, 155 mg, 0.27 mmol), zinc powder (0.176 mg, 2.69 μmol), dicyanozinc (47.4 mg, 0.40 mmol), Pd$_2$dba$_3$ (12.31 mg, 0.01 mmol), and xantphos (15.56 mg, 0.03 mmol) in DMA (1.5 mL) were heated at 130° C. for 2 h. The reaction mixture was purified by chromatography on silica gel (10% MeOH/1% NH$_4$OH in DCM) to give the title product (73.0 mg, 52.0%).

¹H NMR (400 MHz, DMSO-d₆) δ ppm 11.95 (br. s., 1H), 9.17 (s, 1H), 8.62 (s, 1H), 8.50 (s, 1H), 7.46 (br. s., 1H), 7.25 (d, 1H), 7.17 (br. s., 1H), 6.67 (br. s., 1H), 6.54 (d, 1H), 3.89-3.63 (m, 5H), 2.73 (br. s., 2H), 2.67 (s, 1H), 2.55 (d, 2H), 2.33 (br. s., 6H), 2.15 (s, 4H), 1.87 (d, 2H), 1.54 (d, 2H). m/z 523.

EXAMPLE 29

N-(4-(4-(dimethylamino)piperidin-1-yl)-2-methoxyphenyl)-4-(1H-indol-3-yl)-5-(trifluoromethyl)pyrimidin-2-amine as the trifluoroacetic acid salt

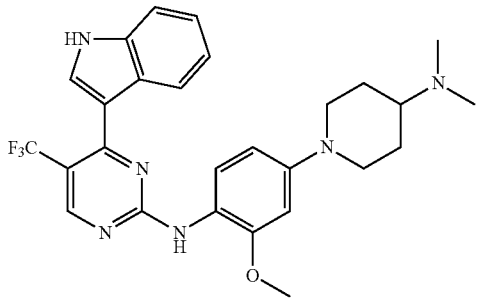 [SMILES: COc1cc(N2CCC(N(C)C)CC2)ccc1Nc1ncc(C(F)(F)F)c(-c2c[nH]c3ccccc23)n1]

Starting materials: 3-(2-chloro-5-(trifluoromethyl)pyrimidin-4-yl)-1H-indole (INTERMEDIATE 4) and 1-(4-amino-3-methoxyphenyl)-N,N-dimethylpiperidin-4-amine (INTERMEDIATE 28).

¹H NMR (300 MHz, DMSO-d₆) δ ppm 11.77 (s, 1H), 9.47 (br. s, 1H), 8.86 (s, 1H), 8.59 (s, 1H), 7.85 (s, 1H), 7.42 (dd, 2H), 7.16 (t, 1H), 7.13 (br. s, 1H), 6.70 (s, 1H), 6.53 (d, 1H), 3.90 (d, 2H), 3.79 (s, 3H), 2.80-2.69 (m, 8H), 2.10-2.07 (m, 2H), 1.78-1.70 (m, 2H). m/z 511.0

EXAMPLE 30

N-(4-(4-amino-3,3-dimethylpiperidin-1-yl)-2-methoxyphenyl)-5-chloro-4-(1H-indol-3-yl)pyrimidin-2-amine

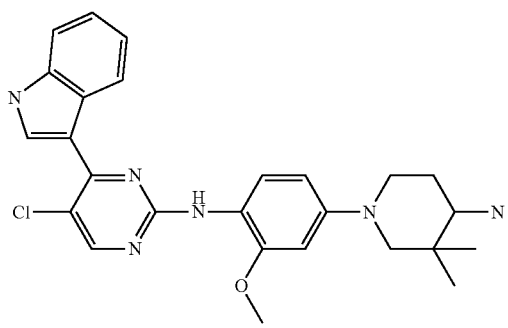 [SMILES: COc1cc(N2CCC(N)C(C)(C)C2)ccc1Nc1ncc(Cl)c(-c2c[nH]c3ccccc23)n1]

Starting materials: 3-(2,5-dichloropyrimidin-4-yl)-1H-indole (Intermediate 2) and 1-(4-amino-3-methoxyphenyl)-3,3-dimethylpiperidin-4-amine (180 mg, 0.72 mmol) (Intermediate 43).

¹H NMR (400 MHz, DMSO-d₆) δ ppm 11.82 (br. s., 1H), 8.47 (s, 1H), 8.13-8.40 (m, 3H), 7.45 (d, 1H), 7.39 (d, 1H), 7.16 (t, 1H), 6.97 (t, 1H), 6.61 (d, 1H), 6.49 (m, 1H), 3.67-3.78 (m, 3H), 3.61 (d, 1H), 2.71 (m, 1H), 2.34-2.47 (m, 2H), 1.63-1.76 (m, 1H), 1.46-1.59 (m, 2H), 0.85-1.02 (m, 6H). m/z 478.

EXAMPLE 31

5-chloro-N-(4-(3,3-dimethyl-4-(methylamino)piperidin-1-yl)-2-methoxyphenyl)-4-(1H-indol-3-yl)pyrimidin-2-amine

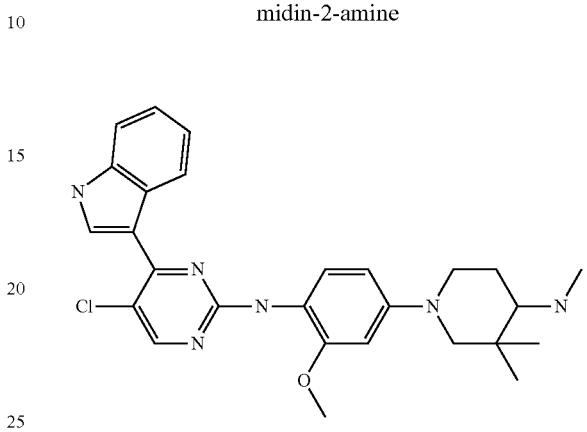

Starting materials: 3-(2,5-dichloropyrimidm-4-yl)-1H-indole (INTERMEDIATE 2) and), 1-(4-amino-3-methoxyphenyl)-N,3,3-trimethylpiperidin-4-amine (INTERMEDIATE 44).

¹H NMR (400 MHz, DMSO-d₆) δ ppm 11.81 (br. s., 1H), 8.47 (d, 1H), 8.17-8.39 (m, 3H), 7.45 (d, 1H), 7.39 (d, 1H), 7.16 (t, 1H), 6.97 (t, 1H), 6.62 (d, 1H), 6.49 (dd, 1H), 3.76 (s, 3H), 3.66 (d, 1H), 3.27 (d, 1H), 2.63-2.74 (m, 1H), 2.26-2.41 (m, 3H), 2.07 (d, 1H), 1.93 (dd, 1H), 1.42 (d, 1H), 1.25 (br. s., 1H), 0.91-1.07 (m, 6H). m/z 492.

EXAMPLE 32

5-chloro-N-(4-(4-(dimethylamino)-3,3-dimethylpiperidin-1-yl)-2-methoxyphenyl)-4-(1H-indol-3-yl)pyrimidin-2-amine

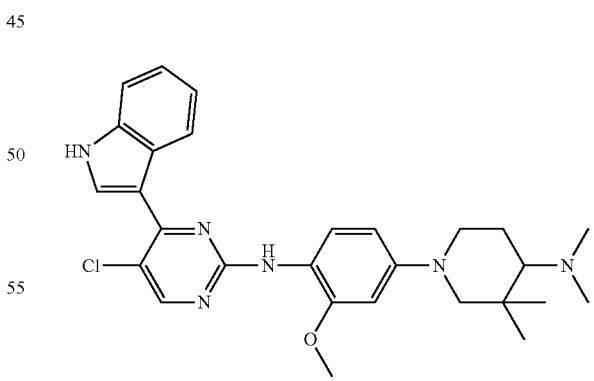

Starting materials: 3-(2,5-dichloropyrimidin-4-yl)-1H-indole (INTERMEDIATE 2) and 1-(4-amino-3-methoxyphenyl)-N,N,3,3-tetramethylpiperidin-4-amine (INTERMEDIATE 45).

¹H NMR (400 MHz, DMSO-d₆) δ ppm 11.82 (br. s., 1H) 8.47 (d, 1H) 8.10-8.38 (m, 3H) 7.26-7.53 (m, 2H) 7.16 (t, 1H) 6.97 (t, 1H) 6.62 (d, 1H) 6.49 (dd, 1H) 3.82 (d, 1H) 3.76 (s, 3H) 2.56-2.72 (m, 1H) 2.43 (d, 2H) 2.28 (s, 6H) 2.15 (dd, 1H) 1.69-1.85 (m, 2H) 0.99 (s, 3H) 1.03 (s, 3H). m/z 506.

EXAMPLE 33

N-(4-((3R,4S)-4-amino-3-fluoropiperidin-1-yl)-2-methoxyphenyl)-5-chloro-4-(1H-indol-3-yl)pyrimidin-2-amine

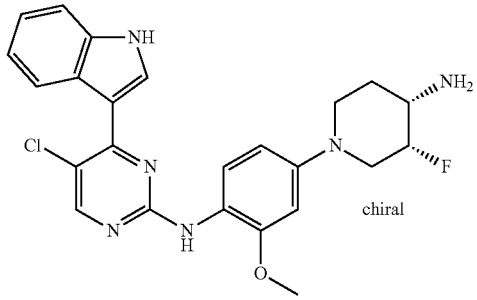 [SMILES: COc1cc(N2CC[C@H](N)[C@H](F)C2)ccc1Nc1ncc(Cl)c(-c2c[nH]c3ccccc23)n1]

1-Pentanol (2 mL) was injected into a microwave vial charged with p-toluenesulfonic acid (0.180 g, 0.95 mmol), (3R,4S)-1-(4-amino-3-methoxyphenyl)-3-fluoropiperidin-4-amine (Intermediate 48) (0.091 g, 0.38 mmol), and 3-(2,5-dichloropyrimidin-4-yl)-1H-indole (Intermediate 2) (0.1 g, 0.38 mmol). The reaction was microwaved at 140° C. for 1 h. The solution was concentrated under reduced pressure. The crude residue was dissolved in DCM (15 mL) and washed with a sat. Na$_2$CO$_3$ solution. The organic layer was dried over Na$_2$SO$_4$, filtered, and the filtrate was concentrated to give a crude liquid. The crude material was purified using silica gel chromatography (2-10% MeOH and 1% NH$_4$OH in DCM) to give the title product (0.062 g, 35.1%).

$^1$H NMR (300 MHz, DMSO-d$_6$) δ ppm 11.81 (br. s, 1H), 8.47 (s, 1H), 8.27 (d, 2H), 7.45 (m, 1H), 7.14 (t, 1H), 6.99 (t, 1H), 6.66 (s, 1H), 6.51 (m, 1H), 4.70 (d, 1H), 3.83-3.59 (m, 5H), 2.94-2.86 (m, 3H), 1.76-1.64 (m, 4H). m/z 467.

EXAMPLE 34

5-Chloro-N-(2-methoxy-4-(4-(4-methylpiperazin-1-yl)piperidin-1-yl)phenyl)-4-(1-methyl-1H-indol-3-yl)pyrimidin-2-amine HCl salt

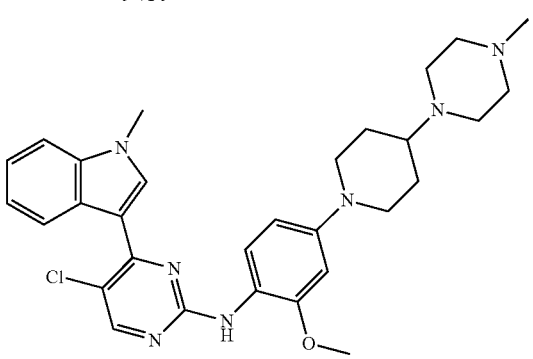

2,2,2-Trifluoroethanol (1.5 ml) was added to a 10 mL vial charged with 4 N HCl in dioxane (0.135 ml, 0.54 mmol), 2-methoxy-4-(4-(4-methylpiperazin-1-yl)piperidin-1-yl)aniline (0.082 g, 0.27 mmol), and 3-(2,5-dichloropyrimidin-4-yl)-1-methyl-1H-indole (INTERMEDIATE 49, 0.075 g, 0.27 mmol). The reaction was stirred at RT for 5 min and then microwaved at 150° C. for 50 min. Concentration in vacuo gave a crude residue, and it was purified by silica gel chromatography (10% methanol and 1% ammonium hydroxide in DCM) to give the product (0.105 g, 66.8%). The product was stirred in 20 mL of 0.5 N HCl in methanol for 1 min and then concentrated under reduced pressure to give the title product. (yellow solid).

$^1$H NMR (300 MHz, DMSO-d$_6$) δ ppm 8.61 (s, 1H), 8.38-8.33 (m, 2H), 7.65 (br. s., 1H), 7.53 (d, 1H), 7.28 (t, 1H), 7.09 (t, 1H), 6.88 (br. s., 1H), 3.92-3.75 (m, 14H), 3.50 (br. s., 5H), 3.11 (br. s., 2H), 2.86 (s, 3H), 2.33-2.29 (m, 2H), 2.10 (br. s., 2H). m/z 546.

EXAMPLE 35

N-(4-(4-aminopiperidin-1-yl)-2-methoxyphenyl)-5-chloro-4-(1-methyl-1H-indol-3-yl)pyrimidin-2-amine TFA salt

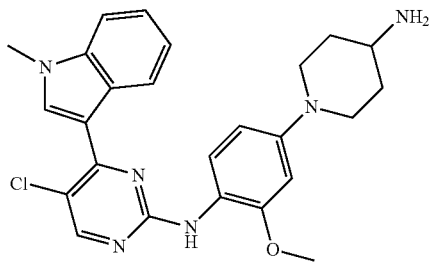 [SMILES: COc1cc(N2CCC(N)CC2)ccc1Nc1ncc(Cl)c(-c2cn(C)c3ccccc23)n1]

Example 35 was prepared from the indicated starting materials using a method similar to the one described for the preparation of Example 34.

Starting materials: 3-(2,5-dichloropyrimidin-4-yl)-1-methyl-1H-indole (INTERMEDIATE 49) and tert-butyl 1-(4-amino-3-methoxyphenyl)piperidin-4-ylcarbamate (INTERMEDIATE 56).

$^1$H NMR (300 MHz, DMSO-d$_6$) δ ppm 8.55 (s, 1H), 8.37-8.32 (m, 2H), 8.00 (br. s., 2H), 7.54-7.50 (m, 2H), 7.25 (t, 1H), 7.05 (t, 1H), 6.80 (br. s., 1H), 6.63 (d, 1H), 3.90 (s, 3H), 3.78 (s, 5H), 3.25 (br. s., 1H), 2.92 (t, 2H), 2.04-2.00 (m, 2H), 1.78-1.67 (m, 2H). m/z 463.

EXAMPLE 36

5-fluoro-N-(2-methoxy-4-(4-(4-methylpiperazin-1-yl)piperidin-1-yl)phenyl)-4-(1-methyl-1H-indol-3-yl)pyrimidin-2-amine

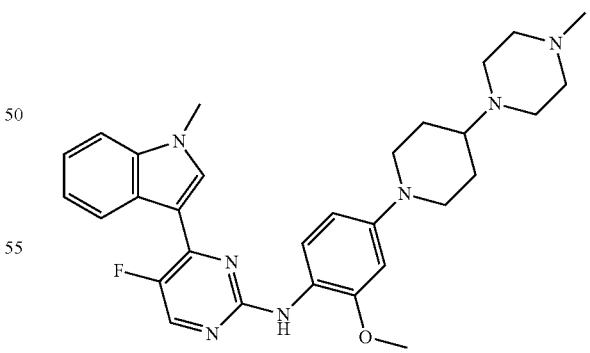

Example 36 was prepared from the indicated starting materials using a method similar to the one described for the preparation of Example 34.

Starting materials: 3-(2-chloro-5-fluoropyrimidin-4-yl)-1-methyl-1H-indole (INTERMEDIATE 50) and 2-methoxy-4-(4-(4-methylpiperazin-1-yl)piperidin-1-yl)aniline (INTERMEDIATE 27).

¹H NMR (300 MHz, DMSO-d₆) δ ppm 8.43 (d, 1H), 8.28 (d, 1H), 8.16 (s, 1H), 8.04 (s, 1H), 7.54-7.50 (m, 2H), 7.27 (t, 1H), 7.09 (t, 1H), 6.66 (s, 1H), 6.53 (dd, 1H), 3.90 (s, 3H), 3.77 (s, 3H), 3.72 (s, 2H), 2.70 (t, 2H), 2.32 (br. s., 5H), 2.15 (s, 3H), 1.89-1.85 (m, 2H), 1.61-1.53 (m, 2H). m/z 530.

EXAMPLE 37

5-Fluoro-N-[5-fluoro-2-methoxy-4-[4-(4-methylpiperazin-1-yl)-1-piperidyl]phenyl]-4-(1H-indol-3-yl)pyrimidin-2-amine trifluoroacetic acid salt

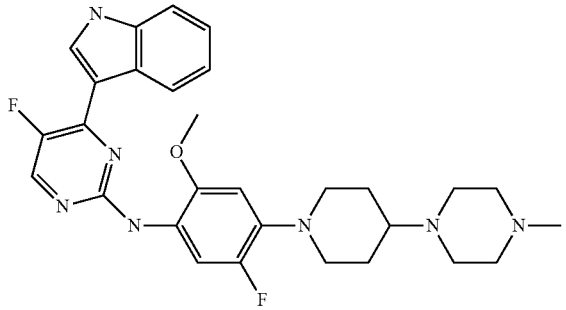 [SMILES: COc1cc(N2CCC(N3CCN(C)CC3)CC2)c(F)cc1Nc1ncc(F)c(-c2c[nH]c3ccccc23)n1]

5-Fluoro-2-methoxy-4-(4-(4-methylpiperazin-1-yl)piperidin-1-yl)aniline (INTERMEDIATE 54) (0.234 g, 0.73 mmol) and 3-(2-chloro-5-fluoropyrimidin-4-yl)-1H-indole (INTERMEDIATE 3) (0.18 g, 0.73 mmol) were placed in a 10 mL vial. 1-Pentanol (5 mL) was added to the mixture to give a brown suspension. Tosic acid (0.277 g, 1.45 mmol) was added. The reaction was microwaved at 160° C. for 1 h. After it was cooled to RT, the solution was concentrated in vacuo to give a syrup. Concentrated HCl (1 mL) and water (4 mL) were added to the residue syrup. The suspension was filtered and the filtrate was loaded to a Prep HPLC column (Atlantis T3, 19×100 mm, 5 um) and eluted with acetonitrile (0.1% TFA)/water (0.1% TFA) (5-55%, 10 min). Collected fractions were concentrated to give the title product.

¹H NMR (300 MHz, DMSO-d6) δ ppm 11.98 (br. s., 1H), 8.49 (d, 1H), 8.40 (d, 1H), 8.18 (br. s., 2H), 7.84 (d, 1H), 7.44-7.54 (m, 1H), 7.23 (t, 1H), 7.04-7.16 (m, 1H), 6.75 (d, 1H), 3.85 (s, 3H), 3.49 (s, 6H), 3.13 (br. s., 5H), 2.67-2.89 (m, 5H), 1.98-2.15 (m, 2H), 1.76 (m, 2H). m/z 534.

EXAMPLES 38-40 were prepared from the indicated starting materials using a method similar to the one described in the preparation of EXAMPLE 37.

EXAMPLE 38

N-[5-fluoro-2-methoxy-4-[4-(4-methylpiperazin-1-yl)-1-piperidyl]phenyl]-4-(1H-indol-3-yl)-5-methyl-pyrimidin-2-amine

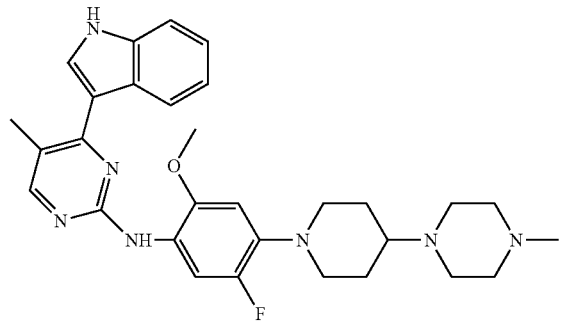

Starting materials: 3-(2,5-dichloropyrimidin-4-yl)-1H-indole (INTERMEDIATE 1) and 5-Fluoro-2-methoxy-4-(4-(4-methylpiperazin-1-yl)piperidin-1-yl)aniline (INTERMEDIATE 54).

¹H NMR (300 MHz, DMSO-d6) δ ppm 12.05 (br. s., 1H), 8.34 (d, 1H), 8.11-8.27 (m, 2H), 7.85 (d, 1H), 7.43-7.58 (m, 1H), 7.22 (t, 1H), 6.99-7.16 (m, 2H), 6.77 (d, 1H), 3.85 (s, 3H), 3.28-3.51 (m, 4H), 3.51-3.67 (m, 3H), 2.90-3.28 (m, 5H), 2.70-2.85 (m, 5H), 2.42 (s, 3H), 2.04 (br. s., 2H), 1.73 (d, 2H). m/z 528.

EXAMPLE 39

5-chloro-N-[5-fluoro-2-methoxy-4-[4-(4-methylpiperazin-1-yl)-1-piperidyl]phenyl]-4-(1H-indol-3-yl)pyrimidin-2-amine

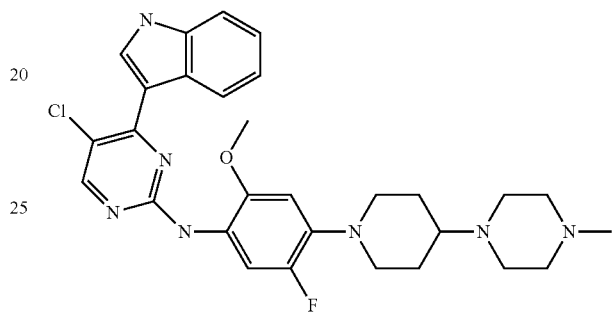

Starting materials: 3-(2,5-dichloropyrimidin-4-yl)-1H-indole (INTERMEDIATE 2) and 5-Fluoro-2-methoxy-4-(4-(4-methylpiperazin-1-yl)piperidin-1-yl)aniline (INTERMEDIATE 54).

¹H NMR (300 MHz, DMSO-d6) δ ppm 11.91 (br. s., 1H), 8.50 (d, 1H), 8.42 (s, 1H), 8.33 (br. s., 2H), 7.73 (d, 1H), 7.49 (d, 1H), 7.20 (t, 1H), 7.04 (t, 1H), 6.75 (d, 1H), 3.83 (s, 3H), 3.50 (d, 6H), 2.87-3.26 (m, 4H), 2.67-2.85 (m, 6H), 1.94-2.14 (m, 2H), 1.63-1.85 (m, 2H). m/z 550.

EXAMPLE 40

5-chloro-N-[5-chloro-2-methoxy-4-[4-(4-methylpiperazin-1-yl)-1-piperidyl]phenyl]-4-(1H-indol-3-yl)pyrimidin-2-amine

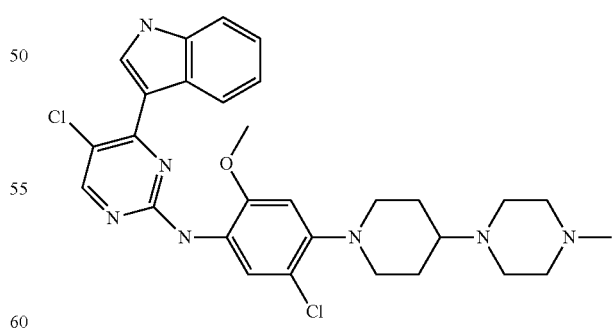

Starting materials: 3-(2,5-dichloropyrimidin-4-yl)-1H-indole (INTERMEDIATE 2) and 5-chloro-2-methoxy-4-(4-(4-methylpiperazin-1-yl)piperidin-1-yl)aniline (INTERMEDIATE 55).

¹H NMR (300 MHz, DMSO-d6) δ ppm 11.90 (br. s., 1H), 8.51 (d, 1H), 8.40 (d, 2H), 8.31 (d, 1H), 7.89 (s, 1H), 7.48 (d, 1H), 7.20 (t, 1H), 7.04 (t, 1H), 6.85 (s, 1H), 3.84 (s, 3H), 3.40 (s, 3H), 3.44 (s, 3H), 2.89-3.14 (m, 3H), 2.67-2.88 (m, 7H), 1.94-2.16 (m, 2H), 1.61-1.81 (m, 2H). m/z 566.

EXAMPLE 41

N-[4-(4-Amino-1-piperidyl)-2-methoxy-phenyl]-5-fluoro-4-(1H-indol-3-yl)pyrimidin-2-amine trifluoroacetic acid salt

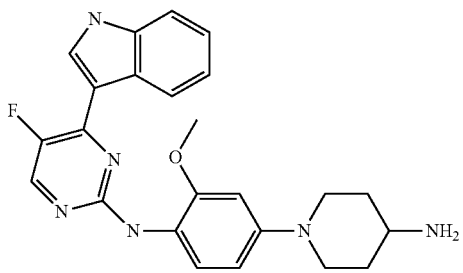 [SMILES: COc1cc(N2CCC(N)CC2)ccc1Nc1ncc(F)c(-c2c[nH]c3ccccc23)n1]

tert-Butyl 1-(4-amino-3-methoxyphenyl)piperidin-4-yl-carbamate (INTERMEDIATE 56) (0.286 g, 0.89 mmol) and 3-(2-chloro-5-fluoropyrimidin-4-yl)-1H-indole (0.20 g, 0.81 mmol) were added into a 10 mL vial. 1-Pentanol (5 mL) was added to give a brown suspension. Tosic acid (0.307 g, 1.62 mmol) was added. The reaction was microwaved at 140° C. for 2 h. After it was cooled to RT, the solution was concentrated in vacuo. Concentrated HCl (1 mL) and water (4 mL) were added to the residue. The suspension was filtered and the filtrate was loaded to a Prep HPLC column (Atlantis T3, 19×100 mm, 5 um) and eluted with 0.1% TFA in acetonitrile/water (0.1% TFA) (5-55%, 7 min). Collected fractions were concentrated to give the title product.

$^1$H NMR (300 MHz, DMSO-d$_6$) δ ppm 11.95 (br. s., 1H), 8.44 (d, 1H), 8.32 (d, 1H), 8.17 (br. s., 1H), 7.90 (br. s., 3H), 7.62 (d, 1H), 7.49 (dd, 2H), 7.21 (t, 1H), 7.10 (t, 2H), 6.77 (br. s., 1H), 6.63 (d, 1H), 3.70-3.87 (m, 5H), 3.14-3.38 (m, 1H), 2.76-3.03 (m, 2H), 2.01 (m, 2H), 1.69 (m, 2H). m/z 433.

EXAMPLE 42

N-[4-(4-amino-1-oxidophosphinan-1-yl)-2-methoxyphenyl]-5-chloro-4-(1H-indol-3-yl)pyrimidin-2-amine trifluoroacetic acid salt, isomer 1

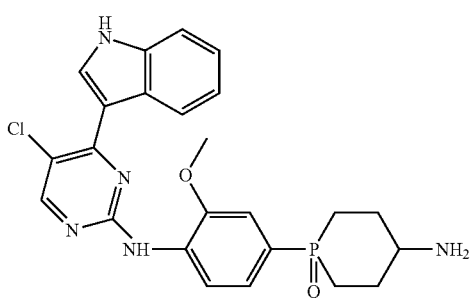 [SMILES: COc1cc(P2(=O)CCC(N)CC2)ccc1Nc1ncc(Cl)c(-c2c[nH]c3ccccc23)n1]

The title compound was synthesized using a method similar to the one described for the preparation of EXAMPLE 37.

Starting materials: 3-(2,5-dichloropyrimidin-4-yl)-1H-indole (INTERMEDIATE 2) and propan-2-yl[1-(4-amino-3-methoxyphenyl)-1-oxidophosphinan-4-yl]carbamate (INTERMEDIATE 62).

$^1$H NMR (300 MHz, DMSO-d6) δ ppm 11.96 (br. s., 1H), 8.45-8.62 (m, 2H), 8.44 (d, 1H), 8.25-8.35 (m, 1H), 7.80 (br. s., 3H), 7.33-7.59 (m, 3H), 7.03-7.29 (m, 3H), 3.97 (s, 3H), 3.27-3.47 (m, 1H), 1.39-2.70 (m, 8H). m/z 482.

EXAMPLE 43

N-[4-(4-amino-1-oxidophosphinan-1-yl)-2-methoxyphenyl]-4-(1H-indol-3-yl)-5-methylpyrimidin-2-amine formic acid salt, isomer 1

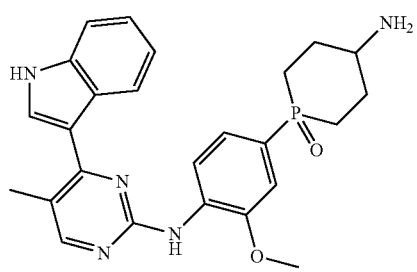 [SMILES: COc1cc(P2(=O)CCC(N)CC2)ccc1Nc1ncc(C)c(-c2c[nH]c3ccccc23)n1]

The title compound was synthesized using a method similar to the one described for the preparation of EXAMPLE 37.

Starting materials: 3-(2,5-dichloropyrimidin-4-yl)-1H-indole (INTERMEDIATE 1) and propan-2-yl[1-(4-amino-3-methoxyphenyl)-1-oxidophosphinan-4-yl]carbamate (INTERMEDIATE 62). The resulted mixture was loaded onto a Prep HPLC column (XSelect CSH Fluoro Phenyl 4.6 mm×50 mm 5 μm) and eluted in acetonitrile/water (0.1% formic acid) (5-20%, 5 min). Collected fractions of the first peak to elute were concentrated to give the title compound.

$^1$H NMR (300 MHz, DMSO-d6) δ ppm 11.86 (br. s., 1H), 8.62 (m, 1H), 8.20-8.46 (m, 5H), 8.02 (d, 2H), 7.32-7.56 (m, 3H), 7.21 (m, 1H), 7.06-7.17 (m, 1H), 4.00 (s, 3H), 3.20-3.36 (m, 1H), 1.58-2.46 (m, 11H). m/z 462.

EXAMPLE 44

N-[4-(4-amino-1-oxidophosphinan-1-yl)-2-methoxyphenyl]-4-(1H-indol-3-yl)-5-methylpyrimidin-2-amine formic acid salt, isomer 2

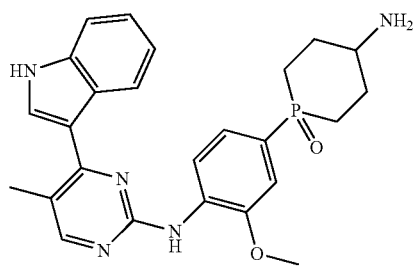 [SMILES: COc1cc(P2(=O)CCC(N)CC2)ccc1Nc1ncc(C)c(-c2c[nH]c3ccccc23)n1]

In the preparation of EXAMPLE 43, collected fractions of the second peak to elute were concentrated to give the title compound.

$^1$H NMR (300 MHz, DMSO-d6) δ ppm 11.85 (br. s., 1H), 8.60 (m, 1H), 8.25-8.48 (m, 4H), 8.01 (d, 2H), 7.44-7.56 (m, 1H), 7.28-7.44 (m, 2H), 7.21 (m, 1H), 7.11 (m, 1H), 3.98 (s, 3H), 3.20-3.31 (m, 1H), 2.41 (s, 3H), 2.04-2.24 (m, 4H), 1.93 (m, 4H). m/z 462.

EXAMPLE 45

(trans)-N-(4-(4-amino-3-fluoropiperidin-1-yl)-2-methoxyphenyl)-5-chloro-4-(1H-indol-3-yl)pyrimidin-2-amine, isomer 1

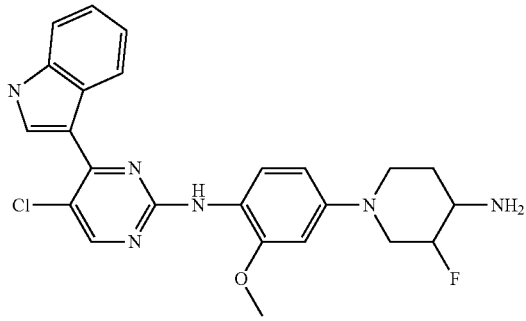 [SMILES: COc1cc(N2CCC(N)C(F)C2)ccc1Nc1ncc(Cl)c(-c2c[nH]c3ccccc23)n1]

A solution of 3-(2,5-dichloropyrimidin-4-yl)-1H-indole (INTERMEDIATE 2) (610 mg, 2.31 mmol), (trans)-(±)-1-(4-amino-3-methoxyphenyl)-3-fluoropiperidin-4-amine (INTERMEDIATE 64) (553 mg, 2.31 mmol), and 4-methylbenzenesulfonic acid hydrate (659 mg, 3.47 mmol) in butanol (12 mL) was heated at 120° C. over night. Solvent was removed by concentration in vacuo, and the residue was partitioned between $CH_2Cl_2$ and $NaHCO_3$ solution. The organic phase was concentrated and purified on silica gel column (10% MeOH in DCM) to give a racemic mixture (300 mg). The racemic mixture was separated using a Chiralpak AD HPLC column (4.6×50 mm, 3μ), with mobile phase: 70% hexane, 30% isopropanol, and 0.1% diethylamine. The first peak to elute was collected and concentrated in vacuo to give the title compound (90 mg, 8.34% yield).

$^1$H NMR (400 MHz, DMSO-$d_6$) δ ppm 11.83 (br. s., 1H), 8.47 (d, 1H), 8.14-8.41 (m, 3H), 7.29-7.59 (m, 2H), 7.03-7.29 (m, 1H), 7.00 (t, 1H), 6.72 (d, 1H), 6.55 (m, 1H), 4.43 (m, 1H), 4.31 (m, 1H), 3.85-4.00 (m, 1H), 3.59 (d, 1H), 3.32 (s, 2H), 2.72-2.98 (m, 4H), 1.94 (m, 1H), 1.38-1.60 (m, 1H). m/z 468.

EXAMPLE 46

(trans)-N-(4-(4-amino-3-fluoropiperidin-1-yl)-2-methoxyphenyl)-5-chloro-4-(1H-indol-3-yl)pyrimidin-2-amine, isomer 2

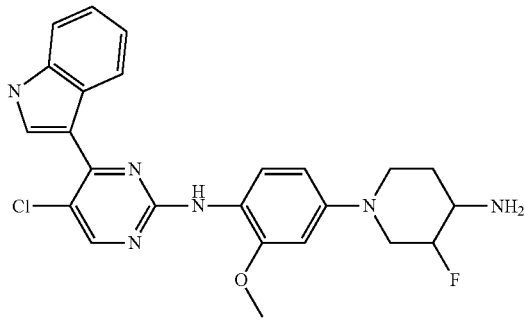 [SMILES: COc1cc(N2CCC(N)C(F)C2)ccc1Nc1ncc(Cl)c(-c2c[nH]c3ccccc23)n1]

In the preparation of EXAMPLE 45, the second peak to elute was collected and concentrated in vacuo to give the title compound (87 mg, 8.07% yield).

$^1$H NMR (400 MHz, DMSO-$d_6$) δ ppm 11.83 (br. s., 1H) 8.47 (d, 1H) 8.14-8.41 (m, 3H) 7.29-7.59 (m, 2H) 7.03-7.29 (m, 1H) 7.00 (t, 1H) 6.72 (d, 1H) 6.55 (m, 1H) 4.43 (m, 1H) 4.31 (m, 1H) 3.85-4.00 (m, 1H) 3.59 (d, 1H) 3.32 (s, 2H) 2.72-2.98 (m, 4H) 1.94 (m, 1H) 1.38-1.60 (m, 1H). m/z 468.

EXAMPLE 47

N-(4-(4-Aminopiperidin-1-yl)-2-methoxyphenyl)-5-chloro-4-(1H-indol-3-yl)pyrimidin-2-amine

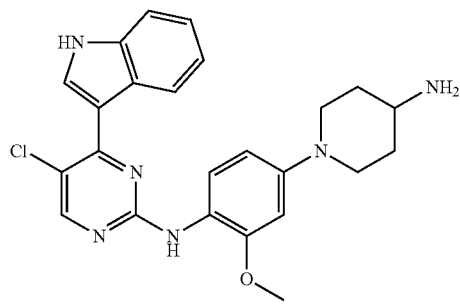 [SMILES: COc1cc(N2CCC(N)CC2)ccc1Nc1ncc(Cl)c(-c2c[nH]c3ccccc23)n1]

A solution of 3-(2,5-dichloropyrimidin-4-yl)-1H-indole (5.28 g, 20 mmol), 1-(4-amino-3-methoxyphenyl)piperidin-4-amine (4.43 g, 20.00 mmol), and tosic acid (5.71 g, 30.00 mmol) in n-pentanol (40.0 ml) was placed in a round-bottomed flask. The solution was heated at 140° C., and stirred at that temperature for three days. The solvent was removed by concentration in vacuo, and to the residue was added sat. $NaHCO_3$ solution and dichloromethane. The mixture was filtered and the obtained solid was dissolved in a mixture of THF and methanol and pre-absorbed on silica gel (120 g). The mixture was loaded onto silica gel column and eluted with 10% MeOH, 1% $NH_4OH$ in DCM. The collected fractions were concentrated, and the residue was triturated in diethyl ether. The collected solid after filtration was triturated in ethanol. Filtration afforded the title compound (3.25 g, 36.2% yield).

$^1$H NMR (400 MHz, DMSO-$d_6$) δ ppm 11.80 (br. s, 1H), 8.47 (s, 1H), 8.17-8.35 (m, 3H), 7.45 (d, 1H), 7.42 (d, 1H), 7.12-7.21 (m, 1H), 6.99 (t, 1H), 6.66 (d, 1H), 6.51 (m, 1H), 3.76 (s, 3H), 3.64 (m, 2H), 2.66-2.81 (m, 3H), 1.75-1.89 (m, 2H), 1.61 (br. s, 2H), 1.31-1.44 (m, 2H). m/z 449.

EXAMPLE 48

4-(1H-Indol-3-yl)-N-(2-methoxy-4-(4-(4-methylpiperazin-1-yl)piperidin-1-yl)phenyl)-5-methylpyrimidin-2-amine

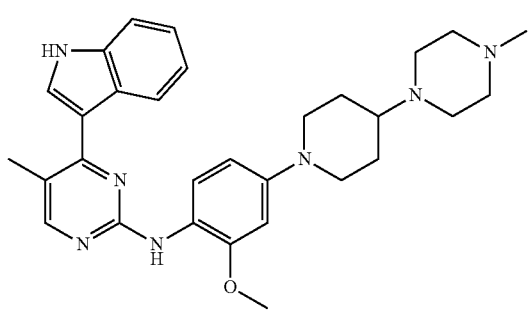

As an alternate procedure to the compound described in Example 9, a solution of 3-(2-chloro-5-methylpyrimidin-4-yl)-1H-indole (INTERMEDIATE 1, 3.39 g, 13.9 mmol), 2-methoxy-4-(4-(4-methylpiperazin-1-yl)piperidin-1-yl)

aniline (INTERMEDIATE 27, 4.23 g, 13.89 mmol), and PTSA monohydrate (6.61 g, 34.74 mmol) in n-pentanol (56 mL) was heated in an oil bath at 140° C. overnight. The reaction mixture was allowed to cool to RT. Hunig's base (10 mL) was added. Solvent was removed in vacuo and to the residue was added methanol (500 mL). Silica gel (120 g) was added to the mixture. Concentration in vacuo removed the solvent, and the residue was loaded to silica gel column and eluted with 10% MeOH, 1% NH$_4$OH in CH$_2$Cl$_2$. The collected fractions were concentrated and the residue was triturated with diethyl ether. Filtration afforded the solid and it was dissolved in a mixture of CH$_2$Cl$_2$ (100 mL) and MeOH (500 mL). Concentration in vacuo reduced the solvent volume to 70 mL and filtration yielded the solid as the title compound (3.8 g, 54% yield).

$^1$H NMR (300 MHz, CHLOROFORM-d) δ ppm 8.56 (br. s., 1H), 8.37-8.47 (m, 2H), 8.27 (s, 1H), 7.66 (d, 1H), 7.41-7.52 (m, 2H), 7.18-7.37 (m, 2H), 6.51-6.65 (m, 2H), 3.90 (s, 3H), 3.66 (d, 2H), 2.62-2.79 (m, 6H), 2.53 (br. s., 4H), 2.40-2.47 (m, 1H), 2.33 (s, 3H), 2.38 (s, 3H), 1.97 (m, 2H) 1.74 (m, 2H). m/z 512.

EXAMPLE 49

5-Chloro-4-(1H-indol-3-yl)-N-(2-methoxy-4-(4-(4-methylpiperazin-1-yl)piperidin-1-yl)phenyl)pyrimidin-2-amine

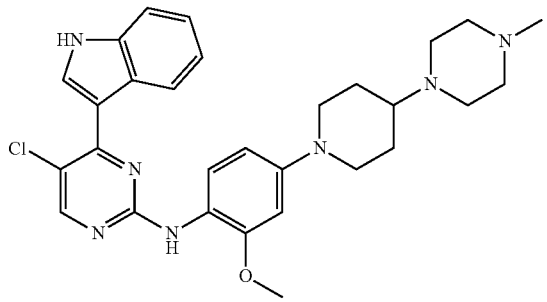 [SMILES: COc1cc(N2CCC(N3CCN(C)CC3)CC2)ccc1Nc1ncc(Cl)c(-c2c[nH]c3ccccc23)n1]

As an alternate procedure to the compound described in Example 10, a solution of 3-(2,5-dichloropyrimidin-4-yl)-1H-indole (INTERMEDIATE 2) (3.67 g, 13.89 mmol), 2-methoxy-4-(4-(4-methylpiperazin-1-yl)piperidin-1-yl) aniline (INTERMEDIATE 27) (4.23 g, 13.89 mmol), and PTSA monohydrate (6.6 g, 34.7 mmol) in n-pentanol (56 mL) was heated in an oil bath at 140° C. overnight. The reaction mixture was cooled to RT. Hunig's base (10 mL) was added. Concentration in vacuo removed the solvent, and the residue was loaded to silica gel column and eluted with 10% MeOH, 1% NH$_4$OH in CH$_2$Cl$_2$. The collected fractions were concentrated and the residue was triturated with diethyl ether. Filtration afforded the solid and it was dissolved in a mixture of CH$_2$Cl$_2$ (100 mL) and MeOH (500 mL). Concentration in vacuo reduced the solvent volume to 70 mL and filtration yielded the solid as the title compound (3.9 g, 53% yield).

$^1$H NMR (400 MHz, DMSO-d6) d ppm 11.82 (br. s., 1H), 8.47 (d, 1H), 8.30 (s, 1H), 8.25 (s, 2H), 7.36-7.53 (m, 2H), 7.16 (t, 1H), 6.97 (t, 1H), 6.66 (d, 1H), 6.51 (m, 1H), 3.76 (s, 5H), 2.65-2.86 (m, 3H), 2.55 (d, 3H), 2.18-2.41 (m, 5H), 1.85 (br. s., 2H), 1.55 (d, 2H). m/z 533.

EXAMPLE 50

(cis)-N-(4-(4-amino-3-fluoropiperidin-1-yl)-2-methoxyphenyl)-5-chloro-4-(1H-indol-3-yl)pyrimidin-2-amine, isomer 1

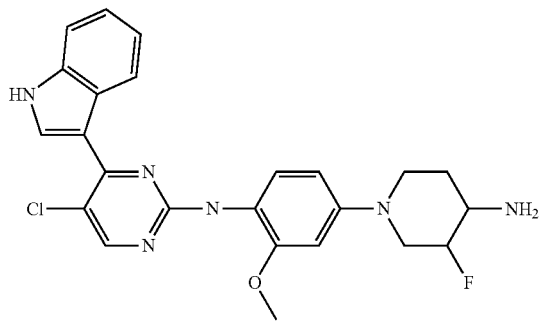 [SMILES: COc1cc(N2CCC(N)C(F)C2)ccc1Nc1ncc(Cl)c(-c2c[nH]c3ccccc23)n1]

The title compound was prepared from the indicated starting materials using a method similar to that described for the preparation of Example 45. Similar to Example 45, the racemic mixture was separated using a Chiralpak AD HPLC column, and the first peak to elute gave isomer 1 of the title compound (0.042 g, 7.0% yield).

Starting material: (cis)-(±)-1-(4-amino-3-methoxyphenyl)-3-fluoropiperidin-4-amine (INTERMEDIATE 65) and 3-(2,5-dichloropyrimidin-4-yl)-1H-indole (INTERMEDIATE 2). The NMR spectra of the title compound was identical to Example 33.

EXAMPLE 51

(cis)-N-(4-(4-amino-3-fluoropiperidin-1-yl)-2-methoxyphenyl)-5-chloro-4-(1H-indol-3-yl)pyrimidin-2-amine, isomer 2

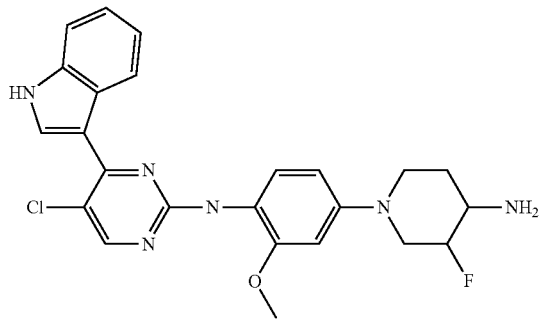 [SMILES: COc1cc(N2CCC(N)C(F)C2)ccc1Nc1ncc(Cl)c(-c2c[nH]c3ccccc23)n1]

In the preparation of EXAMPLE 50, the second peak to elude was collected and concentrated in vacuo to give the title compound (0.038 g, 6.4% yield). The NMR spectra of the title compound was identical to Example 33.

Those skilled in the art will recognize, or be able to ascertain using no more than routine experimentation, that while the invention herein has been described with reference to particular embodiments, it is to be understood that these embodiments are merely illustrative of the principles and applications of the present invention and other embodiments may achieve the same results. It is therefore to be understood that numerous modifications may be made to the illustrative embodiments and that other arrangements may be devised without departing from the spirit and scope of the present invention as defined by the appended claims. The preceding examples may be repeated with similar success by substituting the generically or specifically described reactants and/or operating conditions used.

What is claimed is:

1. A compound, wherein the compound is N-(4-(4-aminopiperidin-1-yl)-2-methoxyphenyl)-5-chloro-4-(1H-indol-3-yl) pyrimidin-2-amine as the trifluoroacetic acid salt.

2. A pharmaceutical composition comprising a compound of claim 1, and a pharmaceutically acceptable carrier, diluent, or excipient.

* * * * *